United States Patent
Cirillo et al.

(10) Patent No.: US 6,825,184 B2
(45) Date of Patent: Nov. 30, 2004

(54) 1,4-DISUBSTITUTED BENZO-FUSED UREA COMPOUNDS

(75) Inventors: Pier Francesco Cirillo, Woodbury, CT (US); Abdelhakim Hammach, Danbury, CT (US); John R. Regan, Larchmont, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 161 days.

(21) Appl. No.: 10/269,173

(22) Filed: Oct. 11, 2002

(65) Prior Publication Data

US 2003/0162968 A1 Aug. 28, 2003

Related U.S. Application Data

(60) Provisional application No. 60/330,254, filed on Oct. 18, 2001.

(51) Int. Cl.$^7$ ............... A61K 31/33; A61K 31/52; C07D 471/00; C07D 241/36; C07D 239/00
(52) U.S. Cl. ............ 514/183; 514/163; 514/224.2; 514/229.5; 514/257; 514/230.5; 514/264.1; 514/265.1; 514/259.1; 544/338; 544/349; 544/253; 544/159; 544/47; 544/99; 544/264; 548/377.1; 548/452; 548/302.7; 546/113; 546/118
(58) Field of Search ............... 514/183, 224.2, 514/229.5, 257, 230.5, 230, 264.1, 265.1, 263, 259.1; 544/338, 349, 253, 159, 47, 99, 264, 105; 548/377.1, 452, 302.7; 546/113, 118

(56) References Cited

U.S. PATENT DOCUMENTS

| | | |
|---|---|---|
| 6,297,381 B1 | 10/2001 | Cirillo et al. |
| 6,319,921 B1 | 11/2001 | Cirillo et al. |
| 6,358,945 B1 | 3/2002 | Breitfelder et al. |

FOREIGN PATENT DOCUMENTS

| | | |
|---|---|---|
| WO | 9847885 * | 10/1998 |
| WO | WO 98/52558 | 11/1998 |
| WO | WO 99/07700 | 2/1999 |
| WO | WO 99/23091 | 5/1999 |
| WO | WO 99/32110 A1 | 7/1999 |
| WO | WO 99/32111 A1 | 7/1999 |
| WO | WO 99/32463 A1 | 7/1999 |
| WO | WO 99/62885 | 12/1999 |
| WO | WO 00/26203 | 5/2000 |
| WO | WO 00/35454 | 6/2000 |
| WO | WO 00/43384 | 7/2000 |
| WO | WO 00/55139 | 9/2000 |
| WO | WO 00/55152 | 9/2000 |
| WO | WO 00/62778 | 10/2000 |
| WO | WO 01/36403 A1 | 11/2000 |

OTHER PUBLICATIONS

PubMed Abstract12082286, also cited as Biorheology, 39/1–2,237–46(2002).*
PubMed Abstract 15130663, also cited as Exp. Gerontol. 39/5,687–99(2004).*
PubMed Abstract 15120851, also cited as Neuroscience, 125/4,903–20(2004).*
PubMed Abstract 15106838, also cited as Neuroreport. 15/1,95–8(2004).*

* cited by examiner

*Primary Examiner*—Richard L. Raymond
*Assistant Examiner*—Sudhakr B. Patel
(74) *Attorney, Agent, or Firm*—Robert P. Raymond; Anthony P. Bottino; Timothy X. Witkowski

(57) ABSTRACT

Disclosed are compounds of the formulas (I) & (II) shown below which are active as anti-inflammatory agents. Also disclosed are methods of using and making such compounds.

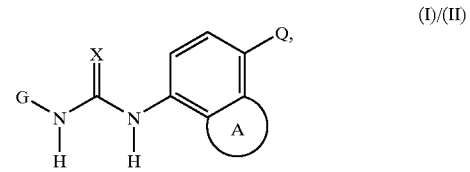

(I)/(II)

wherein G, X, A and Q are described herein.

20 Claims, No Drawings

1,4-DISUBSTITUTED BENZO-FUSED UREA COMPOUNDS

APPLICATION DATA

This application claims benefit to U.S. provisional application Ser. No. 60/330,254 filed Oct. 18, 2001.

TECHNICAL FIELD OF THE INVENTION

This invention relates to 1,4-disubstituted benzo-fused urea compounds of formulas (I) & (II):

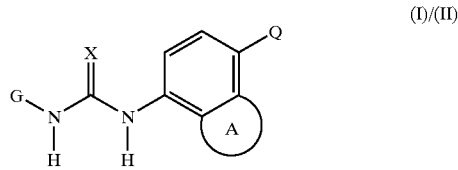

wherein G, X, A and Q of formulas (I)/(II) are defined below. The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, Rev. Infect. Disease 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, J. Invest. Med. 43: 28–38). Studies suggest that inflammatory changes mediated by cytokines may be involved in the pathogenesis of restenosis after percutaneous transluminal coronary angioplasty (PTCA) (Tashiro, H., et al., 2001 March, Coron. Artery Dis. 12(2): 107–13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, British J. Rheum. 35: 334–342 and Stack, W. A., et al., 1997, Lancet 349: 521–524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, Nature Biotechnology 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, Inflamm. Res. 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, Nutrition 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, Biomed Pharmacother. 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, J Bone Miner. Res. 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, Proc. Soc. Exp. Biol. Med. 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., Proc. Natl. Acad. Sci. U.S.A, 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, Aliment. Pharmacol. Ther. 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, Med. Hypotheses, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, Clin. Exp. Immunol. 109, 54). IL-1 and TNF are both involved in periodontal disease. The destructive process associated with periodontal disease may be due to a disregulation of both IL-1 and TNF (Howells, 1995, Oral Dis. 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, Ann. Emerg. Med. 35, 26). TNFα has also been implicated in cachexia and muscle degradation, associated with HIV infection (Lahdiverta et al., 1988, Amer. J. Med., 85, 289). Obesity is associated with an increase incidence of infection, diabetes and cardiovascular disease. Abnormalities in TNFα expression have been noted for each of the above conditions (Loffreda, et al., 1998, FASEB J. 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, Med. Hypotheses 47, 423). An inhibitor of TNFα production, HU-211, was shown to improve the outcome of closed brain injury in an experimental model (Shohami, et al., 1997, J. Neuroimmunol. 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, Circulation, 97, 242).

TNFα levels are elevated in airways of patients with chronic obstructive pulmonary disease and it may contribute to the pathogenesis of this disease (M. A. Higham et al., 2000, Eur. Respiratory J., 15, 281). Circulating TNFα may also contribute to weight loss associated with this disease (N. Takabatake et al., 2000, Amer. J. Resp. & Crit. Care Med., 161 (4 Pt 1), 1179). Elevated TNFα levels have also been found to be associated with congestive heart failure and the level has been correlated with severity of the disease (A. M. Feldman et al., 2000, J. Amer. College of Cardiology, 35, 537). In addition, TNFα has been implicated in reperfusion injury in lung (Borjesson et al., 2000, Amer. J. Physiol., 278, L3–12), kidney (Lemay et al., 2000, Transplantation, 69, 959), and the nervous system (Mitsui et al., 1999, Brain Res., 844, 192).

TNFα is also a potent osteoclastogenic agent and is involved in bone resorption and diseases involving bone resorption (Abu-Amer et al., 2000, J. Biol. Chem., 275, 27307). It has also been found highly expressed in chondrocytes of patients with traumatic arthritis (Melchiorri et al., 2000, Arthritis and Rheumatism, 41, 2165). TNFα has also been shown to play a key role in the development of glomerulonephritis (Le Hir et al., 1998, Laboratory Investigation, 78, 1625).

The abnormal expression of inducible nitric oxide synthetase (iNOS) has been associated with hypertension in the spontaneously hypertensive rat (Chou et al., 1998, Hypertension, 31, 643). IL-1 has a role in the expression of iNOS and therefore may also have a role in the pathogenesis of hypertension (Singh et al., 1996, Amer. J. Hypertension, 9, 867).

IL-1 has also been shown to induce uveitis in rats which could be inhibited with IL-1 blockers. (Xuan et al., 1998, J. Ocular Pharmacol. and Ther., 14, 31). Cytokines including IL-1, TNF and GM-CSF have been shown to stimulate proliferation of acute myelogenous leukemia blasts (Bruserud, 1996, Leukemia Res. 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, Am. J. Contact Dermat. 7, 177). Data obtained from IL-1 knock out mice indicates the critical involvement in fever for this cytokine (Kluger et al., 1998, Clin. Exp. Pharmacol. Physiol. 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, Am. J. Clin. Nutr. 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, Molecular Medicine Today 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopheresis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, Am. J. Rhinol. 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, Current Opinion in Hematology 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, Molecular Neurobiology 15: 307). IL-6 also plays a significant role in osteoporosis. In murine models it has been shown to effect bone resorption and to induce osteoclast activity (Ershler et al., 1997, Development and Comparative Immunol. 21: 487). Marked cytokine differences, such as IL-6 levels, exist in vivo between osteoclasts of normal bone and bone from patients with Paget's disease (Mills, et al., 1997, Calcif. Tissue Int. 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, Cytokines Mol. Ther. 1, 107). Several infectious diseases, such as influenza, indicate IL-6 and IFN alpha as key factors in both symptom formation and in host defense (Hayden, et al., 1998, *J. Clin. Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J. R. Coll. Physicians Lond* 32, 56).

Interferon γ (IFN γ) has been implicated in a number of diseases. It has been associated with increased collagen deposition that is a central histopathological feature of graft-versus-host disease (Parkman, 1998, *Curr. Opin. Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk. Lymphoma.* 19, 173). The development of insulin-dependent diabetes (Type 1) can be correlated with the accumulation in pancreatic islet cells of T-cells producing IFN γ (Ablumunits, et al., 1998, *J. Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann. Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl.* 12, 76). Allergic subjects produce mRNA specific for IFN γ following challenge with Vespula venom (Bonay, et al., 1997, *Clin. Exp. Immunol.* 109, 342). The expression of a number of cytokines, including IFN γ has been shown to increase following a delayed type hypersensitivity reaction thus indicating a role for IFN γ in atopic dermatitis (Szepietowski, et al., 1997, *Br. J. Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am. J. Trop. Med. Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc. Soc. Exp. Biol. Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin. Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al., 1996, *J.+ Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 *Suppl* 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. The specific inhibitors disclosed are structurally distinct from the novel compounds disclosed in the present application disclosed hereinbelow. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalophaty, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFα are allegedly useful for treating acute and chronic inflammation in the lung caused by inhalation of smoke such as cigarette smoke. TNF anatagonists are apparently also useful for the treatment of endometriosis, see EP 1022027 A1. Infliximab, in clinical trials for RA, has also been indicated to be useful for treating various inflammatory diseases including Behcet's disease, uveitis and ankylosing spondylitis. Pancreatitis may also be regulated by inflammatory mediator production, see J Surg Res 2000 May 15, 90(2)95–101; Shock 1998 Sep. 10(3)

:160–75. p38MAP kinase pathway plays an role in *B.burgdorferi*-elicited infammation and may be useful in treating inflammation induced by the Lyme disease agent. Anguita, J. et. al., *The Journal of Immunology*, 2002, 168:6352–6357.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atheroclerosis.

The work cited above supports the principle that inhibition of cytokine production will be beneficial in the treatment of various disease states. Some protein therapeutics are in late development or have been approved for use in particular diseases. Protein therapeutics are costly to produce and have bioavailability and stability problems. Therefore a need exists for new small molecule inhibitors of cytokine production with optimized efficacy, pharmacokinetic and safety profiles.

All references cited in this application are incorporated herein in their entirety.

BRIEF SUMMARY OF THE INVENTION

The work cited above supports the principle that inhibition of cytokine production will be beneficial in the treatment of various disease states.

It is therefore an object of the invention to provide compounds which inhibit the release of inflammatory cytokines such as interleukin-1 and tumor necrosis factor.

It is a further object of the invention to provide methods for treating diseases and pathological conditions involving inflammation such as chronic inflammatory disease, using the novel compounds of the invention.

It is yet a further object of the invention to provide processes of preparation of the above-mentioned novel compounds.

DETAILED DESCRIPTION OF THE INVENTION

In a first broad generic aspect of the invention, there are provided compounds of the formula (I):

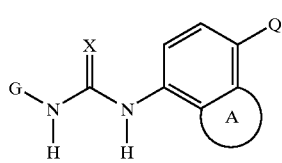

(I)

ring A is:
fused saturated or unsaturated ring containing 3–5 carbon atoms wherein ring A or the phenyl ring to which it is fused is optionally substituted by one or more $C_{1-6}$ branched or unbranched alkyl, acetyl, aroyl, $C_{1-6}$ branched or unbranched alkoxy, halogen, methoxycarbonyl, phenylsulfonyl, hydroxy, amino, mono- or di-($C_{1-4}$ alkyl)amino, mono- or di-($C_{1-4}$ alkyl)amino-S(O)$_m$, cyano, nitro or $H_2NSO_2$;

Preferred formula (I) compounds are those where ring A and the phenyl ring to which it is fused form:

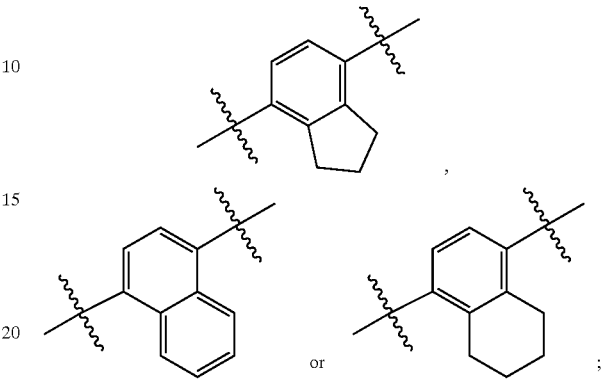

G is a 5-membered heteroaryl ring;
wherein G is optionally substituted by one or more $R_1$, $R_2$ or $R_3$;
Q is
 a carbocyclic ring chosen from naphthyl, benzocyclobutanyl, dihydronaphthyl, tetrahydronaphthyl, benzocycloheptanyl, benzocycloheptenyl, indanyl and indenyl;
a ring system chosen from benzoxazinyl, benzimidazolyl, benzothiazolyl, benzooxazolyl, benzofuranyl, benzopyranyl, benzodioxolyl, quinaldinyl, quinazolinyl, quinoxalinyl, isoquinolinyl, quinolinyl, indolyl, isoindolyl, indolinyl, purinyl, tetrahydroquinolinyl, indazolyl, imidazo-pyridinyl, pyrazolo-pyridinyl, pyrazolo-pyrimidinyl, pyrrolo-pyrimidinyl, pyrrolo-pyridinyl, pyrido-pyrazinyl, pyrido-pyrimidinyl, pyrido-oxazinyl, pyrido-thiazinyl, pyrido-oxazolyl, pyrido-thioxazolyl, pyrimido-pyrimidine, pteridinyl, cinnolinyl and naphthyridinyl;
wherein each Q is optionally substituted with one to three Y, each Y is independently chosen from
L-NR$_5$R$_6$ wherein L is a bond, —(CH$_2$)$_{1-5}$— or >C(O),
hydrogen, oxo, $C_{1-5}$ alkyl branched or unbranched, $C_{1-3}$ alkyl(OH), $C_{2-5}$ alkenyl, $C_{1-3}$ acyl, heterocyclyl$C_{0-3}$ alkyl wherein the heterocyclyl is chosen from morpholinyl, piperazinyl, piperidinyl, pyrrolidinyl, tetrahydropyranyl and tetrahydrofuryl, heteroaryl$C_{0-3}$ alkyl wherein the heteroaryl is chosen from pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl and indazolyl and aryl$C_{0-3}$ alkyl,
wherein each Y is optionally substituted by one to three hydroxy, oxo, $C_{1-4}$ alkyl, $C_{1-3}$ alkoxy, $C_{1-4}$ acyl, $C_{1-5}$ alkoxycarbonyl, —NR$_5$R$_6$ or NR$_5$R$_6$—C(O)—;
each R$_5$ or R$_6$ is independently:
hydrogen, aryl$C_{0-3}$ alkyl, $C_{3-7}$ cycloalkyl$C_{0-3}$ alkyl, heterocyclyl$C_{0-3}$ alkyl or heterocyclylcarbonyl wherein the heterocyclyl is as hereinabove described for Y, heteroaryl$C_{0-3}$ alkyl or heteroarylcarbonyl wherein the heteroaryl is as hereinabove described for Y, $C_{1-3}$ acyl, aroyl or $C_{1-6}$ branched or unbranched alkyl, each $R_5$ or $R_6$ is optionally substituted by $C_{1-5}$ alkoxy, hydroxy, mono- or di-$C_{1-3}$alkylaminocarbonyl, mono or di$C_{1-3}$ alkyl amino, mono or di$C_{1-3}$ alkylsulfonylamino or $C_{1-3}$ alkylsulfonyl;

each $R_1$ is independently:

$C_{1-10}$ alkyl branched or unbranched, wherein one or more C atoms are optionally independently replaced by O, N or $S(O)_m$, and wherein said $C_{1-10}$ alkyl is optionally substituted with one to three $C_{3-10}$ cycloalkyl, hydroxy, oxo, phenyl, naphthyl or halogen;

or $R_1$ is cyclopropyloxy, cyclobutyloxy, cyclopentyloxy, cyclohexyloxy or cycloheptyloxy each optionally substituted with one to three $C_{1-3}$ alkyl groups, nitrile, hydroxy$C_{1-3}$alkyl or aryl;

phenyloxy or benzyloxy each optionally substituted with one to three $C_{1-3}$ alkyl groups, nitrile, hydroxy$C_{1-3}$alkyl or aryl;

cyclopropyl, cyclobutyl, cyclopentyl, cyclohexyl, cycloheptyl, bicyclopentanyl, bicyclohexanyl or bicycloheptanyl, each being optionally substituted with one to three $C_{1-3}$ alkyl, nitrile, hydroxy$C_{1-3}$alkyl or aryl;

$C_{3-10}$ branched or unbranced alkenyl each being optionally substituted with one to three $C_{1-5}$ branched or unbranched alkyl, phenyl or naphthyl;

cyclopentenyl, cyclohexenyl, cyclohexadienyl, cycloheptenyl, cycloheptadienyl, bicyclohexenyl or bicycloheptenyl, wherein each optionally substituted with one to three $C_{1-3}$ alkyl groups;

oxo, nitrile, halogen; or $C_{3-6}$ alkynyl branched or unbranched carbon chain wherein one or more methylene groups are optionally replaced by O, N or $S(O)_m$ and wherein said alkynyl group is optionally independently substituted with one to two oxo groups, hydroxy, pyrrolidinyl, pyrrolyl, tetrahydropyranyl, $C_{1-4}$ alkyl optionally substituted by one or more halogen atoms, nitrile, morpholino, piperidinyl, piperazinyl, imidazolyl, phenyl, pyridinyl, tetrazolyl or mono- or di($C_{1-3}$alkyl)amino;

each $R_2$ is independently:

a $C_{1-6}$ branched or unbranched alkyl optionally halogenated, $C_{1-6}$acyl, aroyl, $C_{1-4}$ branched or unbranched alkoxy optionally halogenated, halogen, methoxycarbonyl, $C_{1-4}$ alkyl-$S(O)_m$ branched or unbranched or phenyl-$S(O)_m$;

each $R_3$ is independently $C_{1-6}$ branched or unbranched alkyl, aryl$C_{0-6}$ alkyl, heteroaryl$C_{0-6}$ alkyl or heterocyclyl $C_{0-6}$ alkyl each optionally substituted with one to three $C_{1-3}$ alkyl groups, nitrile, hydroxy$C_{1-3}$alkyl or aryl;

each m is independently 0, 1 or 2;

and X is O or S;

or the pharmaceutically acceptable derivatives thereof;

with the proviso that the following compounds are excluded:

1-[5-tert-butyl-2-p-tolyl-2H-pyrazol-3-yl]-3-[4-(1-morpholin-4-yl-indan-5-yl)-naphthalen-1-yl]-urea and 1-[5-tert-butyl-2-p-tolyl-2H-pyrazol-3-yl]-3-[4-(3-benzyl-3H-imidazo[4,5]pyridin-6-yl)naphthalen-1-yl]-urea.

In one embodiment of the invention there are provided compounds of the formula (I) as described in the first generic embodiment immediately above and wherein:

G is pyrrolyl, imidazolyl, pyrazolyl, thienyl, furyl, thiazolyl or oxazolyl;

wherein G is optionally substituted by one to three $R_1$, $R_2$ or $R_3$;

ring A and the phenyl ring to which it is fused form:

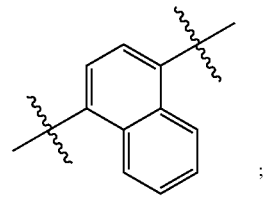

Q is a ring system chosen from benzimidazolyl, benzothiazolyl, benzooxazolyl, benzisoxazolyl, benzofuranyl, benzodioxolyl, indolyl, isoindolyl, imidazo[4,5-b]pyridinyl, imidazo[4,5-c]pyridinyl, purinyl, indazolyl, quinolinyl, isoquinolinyl, quinazolinyl, benzopyranyl, benzoxazinyl, pyrido[2,3-b]oxazinyl, pyrido[2,3-b]pyrazinyl, pyrido[2,3-b]thiazinyl, pyrrolo[3,2-c]pyridinyl and pyrazolo[3,4-d]pyrimidinyl;

wherein each Q is optionally substituted with one to three Y, $R_1$ is $C_{1-10}$ alkyl, $C_{1-10}$ alkoxy each branched or unbranched and optionally substituted with one to three $C_{3-10}$ cycloalkyl, hydroxy, oxo, phenyl, naphthyl or halogen, or $R_1$ is cyclopropyl, cyclobutyl, cyclopentyl, cyclohexyl, cycloheptyl, bicyclopentanyl, bicyclohexanyl or bicycloheptanyl, each optionally substituted with one to three $C_{1-3}$ alkyl, nitrile, hydroxy$C_{1-3}$alkyl or aryl;

$R_3$ is $C_{1-6}$ branched or unbranched alkyl, phenyl, naphthyl, benzyl, phenethyl, heteroaryl$C_{0-6}$ alkyl wherein the heteroaryl is chosen from pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl and indazolyl or heterocyclyl$C_{0-6}$ alkyl wherein the heterocyclyl is chosen from morpholinyl, piperazinyl, piperidinyl, pyrrolidinyl and tetrahydrofuryl, each optionally substituted with one to three $C_{1-3}$ alkyl; and X is O.

In another embodiment of the invention there are provided compounds of the formula (I) as described in the embodiment immediately above and wherein:

G is pyrrolyl, imidazolyl or pyrazolyl, wherein G is optionally substituted by one to three $R_1$, $R_2$ or $R_3$;

each Y is independently chosen from

L-$NR_5R_6$ wherein L is a bond, —$(CH_2)_{1-5}$— or >C(O), hydrogen, oxo, $C_{1-5}$ alkyl branched or unbranched, $C_{1-3}$ alkyl(OH), $C_{2-5}$ alkenyl, $C_{1-3}$ acyl, heterocyclyl$C_{0-3}$ alkyl wherein the heterocyclyl is chosen from morpholinyl, piperazinyl, and pyrrolidinyl, heteroaryl$C_{0-3}$ alkyl wherein the heteroaryl is chosen from pyridinyl, pyrimidinyl, pyrazinyl, pyridazinyl, pyrrolyl, imidazolyl, pyrazolyl, isoxazolyl, thiazolyl, and oxazolyl, phenyl, naphthyl, benzyl and phenethyl, wherein each Y is optionally substituted by one to three hydroxy, oxo, $C_{1-4}$ alkyl, $C_{1-3}$ alkoxy, $C_{1-4}$ acyl, $C_{1-5}$ alkoxycarbonyl or —$NR_5R_6$;

each $R_5$ or $R_6$ is independently:

hydrogen, phenyl, naphthyl, benzyl, phenethyl, $C_{3-7}$ cycloalkyl$C_{0-3}$ alkyl, heterocyclyl$C_{0-3}$ alkyl or heterocyclylcarbonyl wherein the heterocyclyl is chosen from morpholinyl, tetrahydrofuranyl, tetrahydropyranyl, heteroaryl$C_{0-3}$ alkyl or heteroarylcarbonyl wherein the heteroaryl is chosen from pyridinyl, pyrimidinyl, pyrazinyl and pyridazinyl, $C_{1-3}$ acyl, aroyl or $C_{1-6}$ branched or unbranched alkyl, each $R_5$ or $R_6$ is optionally substituted by $C_{1-5}$ alkoxy, mono or di$C_{1-3}$ alkyl amino, mono or di$C_{1-3}$ alkylsulfonylamino or $C_{1-3}$ alkylsulfonyl;

$R_1$ is $C_{1-10}$ alkyl, $C_{1-9}$ alkoxy each branched or unbranched and optionally substituted with one to three $C_{3-10}$ cycloalkyl, hydroxy, oxo, phenyl, naphthyl, fluoro, bromo or chloro; and $R_3$ is $C_{1-6}$ branched or unbranched alkyl, phenyl, naphthyl, benzyl, phenethyl, pyridinyl, morpholinyl, piperazinyl, piperidinyl or pyrrolidinyl each optionally substituted with one to three $C_{1-3}$ alkyl.

In yet another embodiment of the invention there are provided compounds of the formula (I) as described in the embodiment immediately above and wherein:

G is pyrazolyl optionally substituted by one to three $R_1$, $R_2$ or $R_3$;

Q is chosen from imidazo[4,5-b]pyridinyl, imidazo[4,5-c] pyridinyl, pyrido[2,3-b]oxazinyl and pyrrolo[3,2-c] pyridinyl;

wherein each Q is optionally substituted with one to three Y; each Y is independently chosen from L-NR$_5$R$_6$ wherein L is a bond, —(CH$_2$)$_{1-5}$— or >C(O), hydrogen, oxo, $C_{1-5}$ alkyl branched or unbranched, heterocyclyl$C_{0-3}$ alkyl wherein the heterocyclyl is chosen from morpholinyl, piperazinyl, and pyrrolidinyl, pyridinyl$C_{0-3}$ alkyl or benzyl, wherein each Y is optionally substituted by one to three hydroxy, oxo, $C_{1-4}$ alkyl, $C_{1-3}$ alkoxy, $C_{1-4}$ acyl or —NR$_5$R$_6$; and each $R_5$ or $R_6$ is independently:

hydrogen, phenyl, benzyl, $C_{3-6}$ cycloalkyl$C_{0-3}$ alkyl, heterocyclyl$C_{0-3}$ alkyl or heterocyclylcarbonyl wherein the heterocyclyl is chosen from morpholinyl, tetrahydrofuranyl, tetrahydropyranyl, pyridinyl$C_{0-3}$ alkyl, pyridinylcarbonyl, $C_{1-3}$ acyl, benzoyl or $C_{1-6}$ branched or unbranched alkyl, each $R_5$ or $R_6$ is optionally substituted by $C_{1-5}$ alkoxy, mono or di$C_{1-3}$ alkyl amino, mono or di$C_{1-3}$ alkylsulfonylamino or $C_{1-3}$ alkylsulfonyl.

In still another embodiment of the invention there are provided compounds of the formula (I) as described in the embodiment immediately above and wherein:

G is 2H-pyrazol-3-yl optionally substituted by one to three $R_1$, $R_2$ or $R_3$;

Q is chosen from:

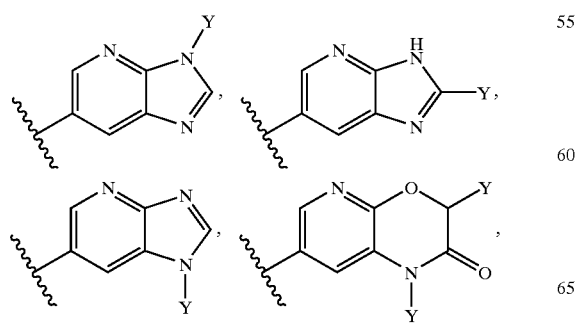

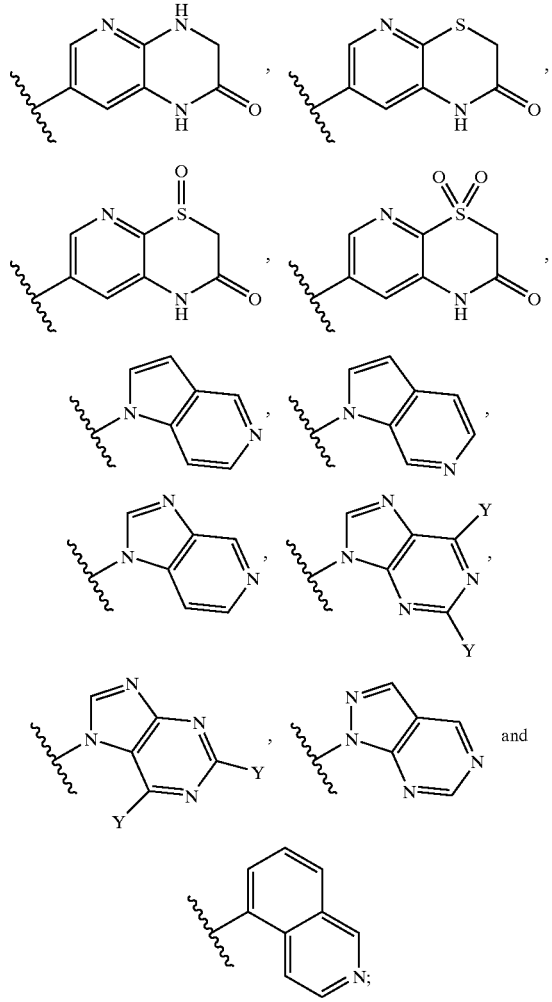

$R_1$ is

CF$_3$, OCF$_3$, —C(CH$_3$)$_3$, —C(CH$_2$F)$_3$ or —CH$_2$C(CH$_3$)$_3$; and $R_3$ is phenyl or benzyl each optionally substituted with one to three $C_{1-3}$ alkyl.

In yet still another embodiment of the invention there are provided compounds of the formula (I) as described in the embodiment immediately above and wherein:

G is:

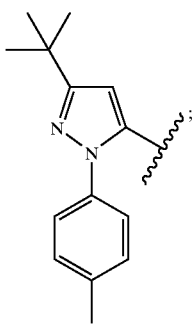

Q is chosen from

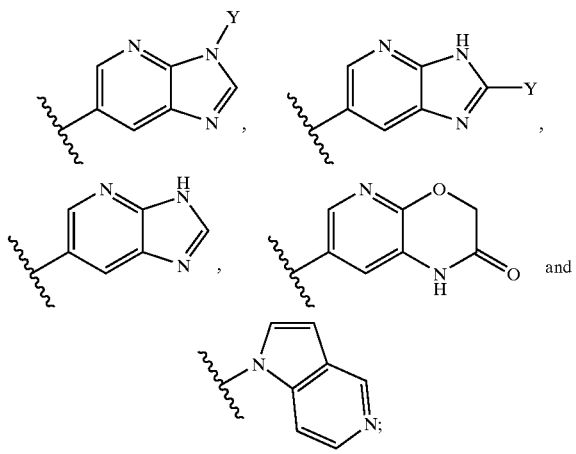

Y is independently chosen from
L-NR$_5$R$_6$ wherein L is a bond or —(CH$_2$)$_{1-3}$—,
C$_{1-5}$ alkyl branched or unbranched, morpholinylC$_{0-3}$ alkyl or benzyl; and
each R$_5$ or R$_6$ is independently:
hydrogen, phenyl, benzyl or C$_{3-6}$ cycloalkylC$_{0-3}$ alkyl.

In a second broad generic aspect of the invention, there are provided compounds of the formula (II):

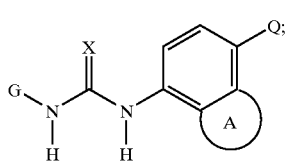

(II)

ring A is:
fused saturated or unsaturated ring containing 3–5 carbon atoms wherein ring A or the phenyl ring to which it is fused is optionally substituted by one or more a C$_{1-6}$ branched or unbranched alkyl, acetyl, aroyl, C$_{1-6}$ branched or unbranched alkoxy, halogen, methoxycarbonyl, phenylsulfonyl, hydroxy, amino, mono- or di-(C$_{1-4}$ alkyl)amino, mono- or di-(C$_{1-4}$ alkyl)amino-S(O)$_m$, cyano, nitro or H$_2$NSO$_2$;

Preferred formula (II) compounds are those where ring A and the phenyl ring to which it is fused form:

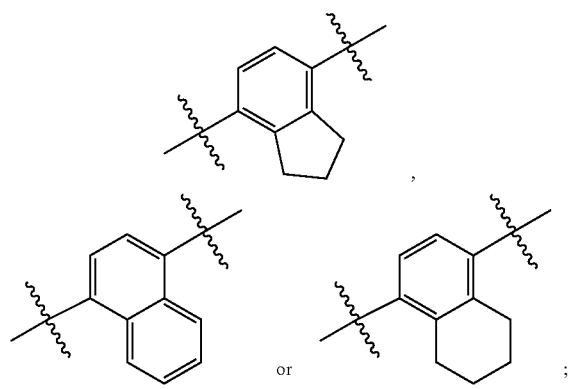

G is
a 6-membered monocyclic heteroaryl ring chosen from pyridinyl, pyrimidinyl, pyrazinyl, and pyridazinyl;
a ring system chosen from benzoxazinyl, benzimidazolyl, benzothiazolyl, benzooxazolyl, benzofuranyl, benzopyranyl, benzodioxolyl, quinaldinyl, quinazolinyl, quinoxalinyl, isoquinolinyl, quinolinyl, indolyl, isoindolyl, indolinyl, purinyl, indazolyl, imidazo-pyridinyl, pyrazolo-pyridinyl, pyrazolo-pyrimidinyl, pyrrolo-pyrimidinyl, pyrrolo-pyridinyl, pyrido-pyrazinyl, pyrido-pyrimidinyl, pyrido-oxazinyl, pyrido-thiazinyl, pyrido-oxazolyl, pyrido-thioxazolyl, pyrimido-pyrimidine, pteridinyl, cinnolinyl and naphthyridinyl;
a 3–7 membered carbocyclic ring aromatic or nonaromatic;
wherein G is optionally substituted by one or more R$_1$, R$_2$ or R$_3$;

Q is
a carbocyclic ring chosen from naphthyl, benzocyclobutanyl, dihydronaphthyl, tetrahydronaphthyl, benzocycloheptanyl, benzocycloheptenyl, indanyl and indenyl;
a ring system chosen from benzoxazinyl, benzimidazolyl, benzothiazolyl, benzooxazolyl, benzofuranyl, benzopyranyl, benzodioxolyl, quinaldinyl, quinazolinyl, quinoxalinyl, isoquinolinyl, quinolinyl, indolyl, isoindolyl, indolinyl, purinyl, tetrahydroquinolinyl, indazolyl, imidazo-pyridinyl, pyrazolo-pyridinyl, pyrazolo-pyrimidinyl, pyrrolo-pyrimidinyl, pyrrolo-pyridinyl, pyrido-pyrazinyl, pyrido-pyrimidinyl, pyrido-oxazinyl, pyrido-thiazinyl, pyrido-oxazolyl, pyrido-thioxazolyl, pyrimido-pyrimidine, pteridinyl, cinnolinyl and naphthyridinyl;
wherein each Q is optionally substituted with one to three Y, each Y is independently chosen from
L-NR$_5$R$_6$ wherein L is a bond, —(CH$_2$)$_{1-5}$— or >C(O),
hydrogen, oxo, C$_{1-5}$ alkyl branched or unbranched, C$_{1-3}$ alkyl(OH), C$_{2-5}$ alkenyl, C$_{1-3}$ acyl, heterocyclylC$_{0-3}$ alkyl wherein the heterocyclyl is chosen from morpholinyl, piperazinyl, piperidinyl, pyrrolidinyl and tetrahydrofuryl, heteroarylC$_{0-3}$ alkyl wherein the heteroaryl is chosen from pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl and indazolyl and arylC$_{0-3}$ alkyl,
wherein each Y is optionally substituted by one to three hydroxy, oxo, C$_{1-4}$ alkyl, C$_{1-3}$ alkoxy, C$_{1-4}$ acyl, C$_{1-5}$ alkoxycarbonyl, —NR$_5$R$_6$ or NR$_5$R$_6$—C(O)—;
each R$_5$ or R$_6$ is independently:
hydrogen, arylC$_{0-3}$ alkyl, C$_{3-7}$ cycloalkylC$_{0-3}$ alkyl, heterocyclylC$_{0-3}$ alkyl or heterocyclylcarbonyl wherein the heterocyclyl is as hereinabove described for Y, heteroarylC$_{0-3}$ alkyl or heteroarylcarbonyl wherein the heteroaryl is as hereinabove described for Y, C$_{1-3}$ acyl, aroyl or C$_{1-6}$ branched or unbranched alkyl, each R$_5$ or R$_6$ is optionally substituted by C$_{1-5}$ alkoxy, hydroxy, mono- or di-C$_{1-3}$alkylaminocarbonyl, mono or diC$_{1-3}$ alkylamino, mono or diC$_{1-3}$ alkylsulfonylamino or C$_{1-3}$ alkylsulfonyl;
each R$_1$ is independently:
C$_{1-10}$ alkyl branched or unbranched, wherein one or more C atoms are optionally independently replaced by O, N or S(O)$_m$, and wherein said C$_{1-10}$ alkyl is optionally substituted with one to three C$_{3-10}$ cycloalkyl, hydroxy, oxo, phenyl, naphthyl or halogen, or R$_1$ is
phenyl, cyclopropyloxy, cyclobutyloxy, cyclopentyloxy, cyclohexyloxy or cycloheptyloxy each optionally substituted with one to three C$_{1-3}$ alkyl groups, nitrile, hydroxyC$_{1-3}$alkyl or aryl;
phenyloxy or benzyloxy each optionally substituted with one to three C$_{1-3}$ alkyl groups, nitrile, hydroxyC$_{1-3}$alkyl or aryl;

cyclopropyl, cyclobutyl, cyclopentyl, cyclohexyl, cycloheptyl, bicyclopentanyl, bicyclohexanyl or bicycloheptanyl, each being optionally substituted with one to three $C_{1-3}$ alkyl, nitrile, hydroxy$C_{1-3}$alkyl or aryl;

$C_{3-10}$ branched or unbranced alkenyl each being optionally substituted with one to three $C_{1-5}$ branched or unbranched alkyl, phenyl or naphthyl, cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

morpholinyl, piperazinyl, piperidinyl, pyrrolidinyl, tetrahydropyranyl or tetrahydrofuryl, oxo, nitrile, halogen; or $C_{3-6}$ alkynyl branched or unbranched carbon chain wherein one or more methylene groups are optionally replaced by O, N or $S(O)_m$ and wherein said alkynyl group is optionally independently substituted with one to two oxo groups, hydroxy, pyrrolidinyl, pyrrolyl, tetrahydropyranyl, one or more $C_{1-4}$ alkyl optionally substituted by one or more halogen atoms, nitrile, morpholino, piperidinyl, piperazinyl, imidazolyl, phenyl, pyridinyl, tetrazolyl or mono- or di($C_{1-3}$alkyl)amino;

each $R_2$ is independently:

a $C_{1-6}$ branched or unbranched alkyl optionally halogenated, $C_{1-6}$acyl, aroyl, $C_{1-4}$ branched or unbranched alkoxy optionally halogenated, halogen, methoxycarbonyl, $C_{1-4}$ alkyl-$S(O)_m$ branched or unbranched or phenyl-$S(O)_m$;

each $R_3$ is independently $C_{1-6}$ branched or unbranched alkyl, aryl$C_{0-6}$ alkyl, heteroaryl$C_{0-6}$ alkyl, heterocyclyl $C_{0-6}$ alkyl each optionally substituted with one to three $C_{1-3}$ alkyl groups, nitrile, hydroxy$C_{1-3}$alkyl or aryl;

amino wherein the nitrogen atom is optionally mono- or di-substituted by $C_{1-6}$ branched or unbranched alkyl, aryl$C_{0-6}$ alkyl, heteroaryl$C_{0-6}$ alkyl and heterocyclyl $C_{0-6}$ alkyl;

J-$S(O)_m$—$NR_7$— wherein the nitrogen atom is covalently attached to G;

or $R_3$ is J-$NR_7$—C(O)—, wherein $R_7$ is hydrogen or $C_{1-3}$ alkyl;

J is chosen from $C_{1-6}$ branched or unbranched alkyl optionally substituted with 1 to 3 halogen atoms, aryl$C_{0-6}$ alkyl, heteroaryl$C_{0-6}$ alkyl and heterocyclyl $C_{0-6}$ alkyl;

each m is independently 0, 1 or 2;

and X is O or S;

or the pharmaceutically acceptable derivatives thereof.

In yet still another embodiment of the invention there are provided compounds of the formula (II) as described in the embodiment immediately above and wherein:

G is a 6-membered monocyclic heteroaryl ring chosen from pyridinyl, pyrimidinyl, pyrazinyl and pyridazinyl;

phenyl, naphthyl, indanyl, indenyl or $C_{3-7}$ cycloalkyl;

wherein G is optionally substituted by one to three $R_1$, $R_2$ or $R_3$;

ring A and the phenyl ring to which it is fused form:

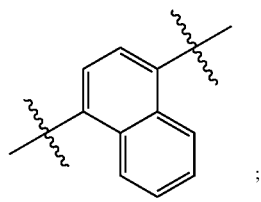

Q is a ring system chosen from benzimidazolyl, benzothiazolyl, benzooxazolyl, benzisoxazolyl, benzofuranyl, benzofuranyl, benzodioxolyl, indolyl, isoindolyl, imidazo[4,5-b]pyridinyl, imidazo[4,5-c]pyridinyl, purinyl, indazolyl, quinolinyl, isoquinolinyl, quinazolinyl, benzopyranyl, benzoxazinyl, pyrido[2,3-b]oxazinyl, pyrido[2,3-b]pyrazinyl, pyrido[2,3-b]thiazinyl, pyrrolo[3,2-c]pyridinyl and pyrazolo[3,4-d]pyrimidinyl;

wherein each Q is optionally substituted with one to three Y, $R_1$ is $C_{1-10}$ alkyl, $C_{1-9}$ alkoxy each branched or unbranched and optionally substituted with one to three $C_{3-10}$ cycloalkyl, hydroxy, oxo, phenyl, naphthyl or halogen, morpholinyl, piperazinyl, piperidinyl, or $R_1$ is phenyl, cyclopropyl, cyclobutyl, cyclopentyl, cyclohexyl, cycloheptyl, bicyclopentanyl, bicyclohexanyl or bicycloheptanyl, each being optionally substituted with one to three $C_{1-3}$ alkyl, nitrile, hydroxy$C_{1-3}$alkyl or aryl;

$R_2$ is halogen, $C_{1-6}$ branched or unbranched alkyl or $C_{1-4}$ branched or unbranched alkoxy each optionally halogenated;

$R_3$ is J-$S(O)_m$—$NR_7$— wherein the nitrogen atom is covalently attached to G and wherein J is chosen from a $C_{1-6}$ branched or unbranched alkyl optionally substituted with 1 to 3 halogen atoms, aryl$C_{0-6}$ alkyl, heteroaryl$C_{0-6}$ alkyl and heterocyclyl $C_{0-6}$ alkyl; and X is O.

In another embodiment of the invention there are provided compounds of the formula (II) as described in the embodiment immediately above and wherein:

G is pyridinyl, phenyl, naphthyl, indanyl, indenyl or $C_{3-7}$ cycloalkyl;

wherein G is optionally substituted by one to three $R_1$, $R_2$ or $R_3$;

wherein each Y is independently chosen from

L-$NR_5R_6$ wherein L is a bond or —$(CH_2)_{1-5}$—;

hydrogen, oxo, $C_{1-5}$ alkyl branched or unbranched, $C_{1-3}$ acyl, heterocyclyl$C_{0-3}$ alkyl wherein the heterocyclyl is chosen from morpholinyl, piperazinyl, and pyrrolidinyl, heteroaryl$C_{0-3}$ alkyl wherein the heteroaryl is chosen from pyridinyl, pyrimidinyl, pyrazinyl, pyridazinyl, pyrrolyl, imidazolyl, pyrazolyl, isoxazolyl, thiazolyl and oxazolyl, phenyl, naphthyl, benzyl and phenethyl, wherein each Y is optionally substituted by one to three hydroxy, oxo, $C_{1-4}$ alkyl, $C_{1-3}$ alkoxy, $C_{1-4}$ acyl, $C_{1-5}$ alkoxycarbonyl or —$NR_5R_6$;

each $R_5$ or $R_6$ is independently:

hydrogen, phenyl, naphthyl, benzyl, phenethyl, $C_{3-7}$ cycloalkyl$C_{0-3}$ alkyl, heterocyclyl$C_{0-3}$ alkyl or heterocyclylcarbonyl wherein the heterocyclyl is chosen from morpholinyl, tetrahydrofuranyl and tetrahydropyranyl, heteroaryl$C_{0-3}$ alkyl or heteroarylcarbonyl wherein the heteroaryl is chosen from pyridinyl, pyridinyl, pyrimidinyl, pyrazinyl and pyridazinyl, $C_{1-3}$ acyl, aroyl or $C_{1-6}$ branched or unbranched alkyl, each $R_5$ or $R_6$ is optionally substituted by $C_{1-5}$ alkoxy, mono or di$C_{1-3}$ alkyl amino, mono or di$C_{1-3}$ alkylsulfonylamino or $C_{1-3}$ alkylsulfonyl;

$R_1$ is $C_{1-10}$ alkyl, $C_{1-9}$ alkoxy each branched or unbranched and optionally substituted with one to three $C_{3-10}$ cycloalkyl, hydroxy, oxo, phenyl, naphthyl, fluoro, bromo or chloro or $R_1$ is morpholinyl or phenyl; and $R_3$ is J-$S(O)_m$—$NR_7$— wherein the nitrogen atom is covalently attached to G and wherein J is chosen from a $C_{1-6}$ branched or unbranched alkyl optionally substituted with 1 to 3 halogen atoms and aryl$C_{0-6}$ alkyl.

In yet another embodiment of the invention there are provided compounds of the formula (II) as described in the embodiment immediately above and wherein:

G is pyridinyl, phenyl, cyclopropyl or naphthyl each optionally substituted by one to three $R_1$, $R_2$ or $R_3$;

Q is chosen from imidazo[4,5-b]pyridinyl, imidazo[4,5-c]pyridinyl, pyrido[2,3-b]oxazinyl, pyrido[2,3-b]pyrazinyl, pyrido[2,3-b]thiazinyl, pyrazolo[3,4-d]pyrimidinyl, isoquinolinyl, purinyl and pyrrolo[3,2-c]pyridinyl;

wherein each Q is optionally substituted with one to three Y, wherein each Y is independently chosen from L-$NR_5R_6$ wherein L is a bond or —$(CH_2)_{1-5}$—, hydrogen, oxo, $C_{1-5}$ alkyl branched or unbranched, heterocyclyl$C_{0-3}$ alkyl wherein the heterocyclyl is chosen from morpholinyl, piperazinyl, and pyrrolidinyl, pyridinyl$C_{0-3}$ alkyl or benzyl, wherein each Y is optionally substituted by one to three hydroxy, oxo, $C_{1-4}$ alkyl, $C_{1-3}$ alkoxy, $C_{1-4}$ acyl or —$NR_5R_6$;

each $R_5$ or $R_6$ is independently:

hydrogen, phenyl, benzyl, $C_{3-6}$ cycloalkyl$C_{0-3}$ alkyl, heterocyclyl$C_{0-3}$ alkyl or heterocyclylcarbonyl wherein the heterocyclyl is chosen from morpholinyl, tetrahydrofuranyl and tetrahydropyranyl, pyridinyl$C_{0-3}$ alkyl, pyridinylcarbonyl, $C_{1-3}$ acyl, benzoyl or $C_{1-6}$ branched or unbranched alkyl optionally substituted by $C_{1-5}$ alkoxy, mono or di$C_{1-3}$ alkyl amino, mono or di$C_{1-3}$ alkylsulfonylamino or $C_{1-3}$ alkylsulfonyl;

$R_7$ is hydrogen; and

J is $C_{1-6}$ branched or unbranched alkyl optionally substituted with 1 to 3 halogen atoms.

In still another embodiment of the invention there are provided compounds of the formula (II) as described in the embodiment immediately above and wherein:

Q is chosen from:

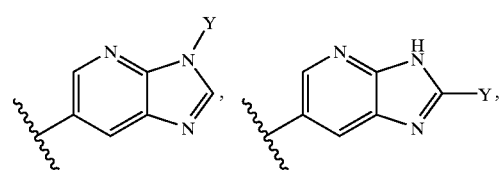

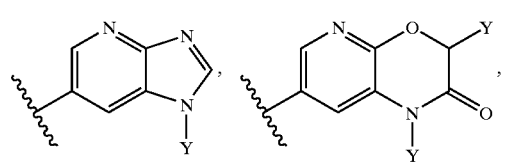

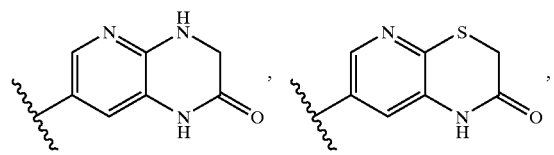

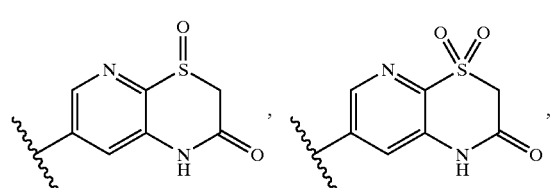

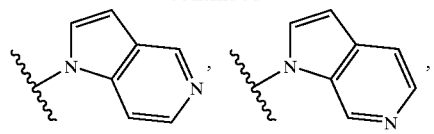

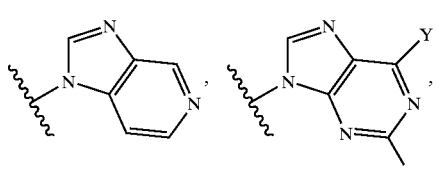

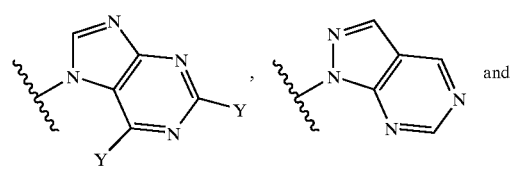

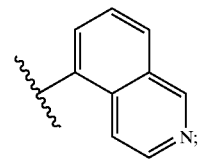

$R_1$ is morpholinyl, phenyl, $CF_3$, $OCF_3$, —$C(CH_3)_3$, —$C(CH_2F)_3$ or —$CH_2C(CH_3)_3$;

$R_2$ is chloro, bromo, fluoro, $C_{1-4}$ branched or unbranched alkoxy, $CF_3$ or $OCF_3$; and J is $C_{1-3}$ alkyl optionally substituted with 1 to 3 halogen atoms.

In yet still another embodiment of the invention there are provided compounds of the formula (II) as described in the embodiment immediately above and wherein:

G is:

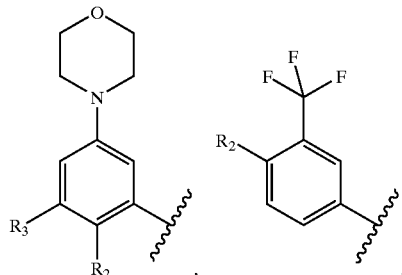

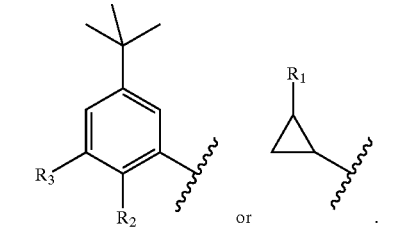

In still another embodiment of the invention there are provided compounds of the formula (II) as described in the embodiment immediately above and wherein:

G is:

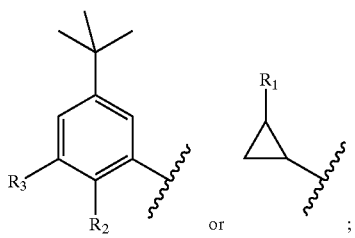

or ;

Y is independently chosen from

L-NR$_5$R$_6$ wherein L is a bond or —(CH$_2$)$_{1-3}$—,

C$_{1-5}$ alkyl branched or unbranched, morpholinylC$_{0-3}$ alkyl or benzyl; and each R$_5$ or R$_6$ is independently:

hydrogen, phenyl, benzyl or C$_{3-6}$ cycloalkylC$_{0-3}$ alkyl.

Table I contains representative compounds of the invention which have been made by according to the general methods and examples in the sections below.

TABLE I

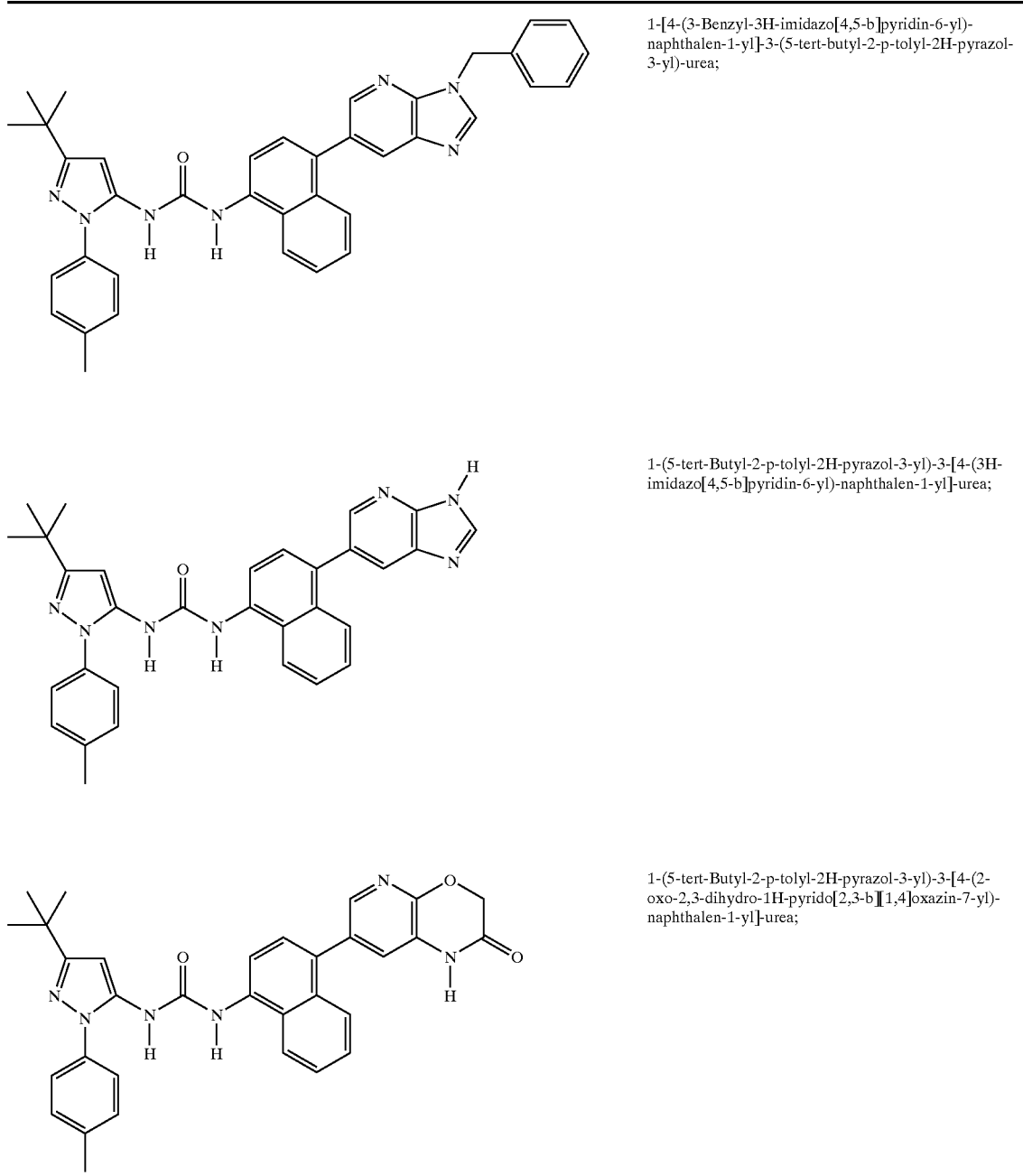

1-[4-(3-Benzyl-3H-imidazo[4,5-b]pyridin-6-yl)-naphthalen-1-yl]-3-(5-tert-butyl-2-p-tolyl-2H-pyrazol-3-yl)-urea;

1-(5-tert-Butyl-2-p-tolyl-2H-pyrazol-3-yl)-3-[4-(3H-imidazo[4,5-b]pyridin-6-yl)-naphthalen-1-yl]-urea;

1-(5-tert-Butyl-2-p-tolyl-2H-pyrazol-3-yl)-3-[4-(2-oxo-2,3-dihydro-1H-pyrido[2,3-b][1,4]oxazin-7-yl)-naphthalen-1-yl]-urea;

TABLE I-continued

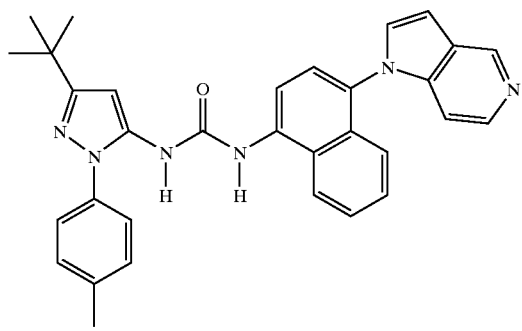

1-(5-tert-Butyl-2-p-tolyl-2H-pyrazol-3-yl)-3-(4-pyrrolo[3,2-c]pyridin-1-yl-naphthalen-1-yl)-urea;

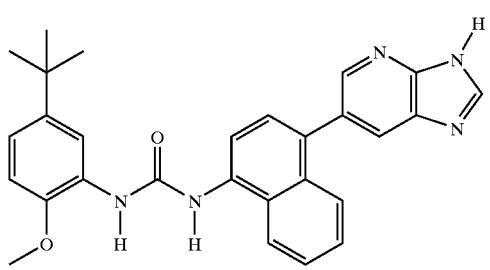

1-(5-tert-Butyl-2-methoxy-phenyl)-3-[4-(3H-imidazo[4,5-b]pyridin-6-yl)-naphthalen-1-yl]-urea;

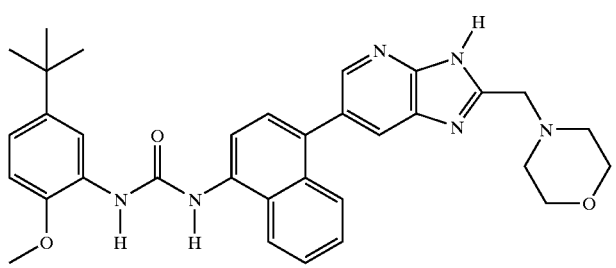

1-(5-tert-Butyl-2-methoxy-phenyl)-3-[4-(2-morpholin-4-ylmethyl-3H-imidazo[4,5-b]pyridin-6-yl)-naphthalen-1-yl]-urea;

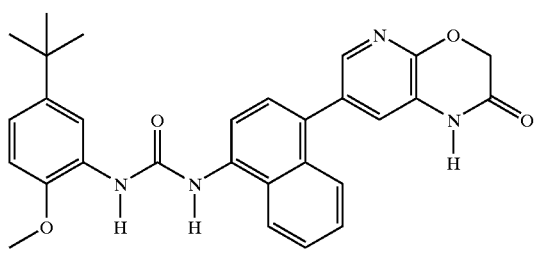

1-(5-tert-Butyl-2-methoxy-phenyl)-3-[4-(2-oxo-2,3-dihydro-1H-pyrido[2,3-b][1,4]oxazin-7-yl)-naphthalen-1-yl]-urea;

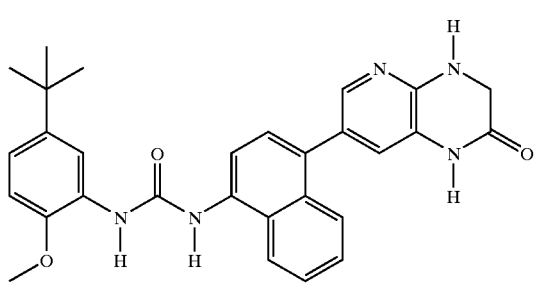

1-(5-tert-Butyl-2-methoxy-phenyl)-3-[4-(2-oxo-1,2,3,4-tetrahydro-pyrido[2,3-b]pyrazin-7-yl)-naphthalen-1-yl]-urea;

TABLE I-continued

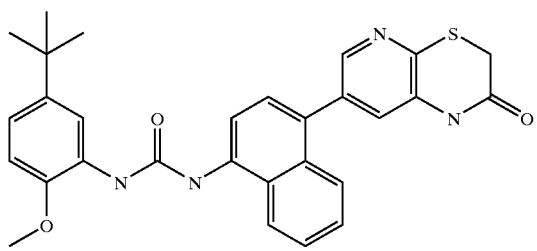

1-(5-tert-Butyl-2-methoxy-phenyl)-3-[4-(2-oxo-2,3-dihydro-1H-pyrido[2,3-b][1,4]thiazin-7-yl)-naphthalen-1-yl]-urea;

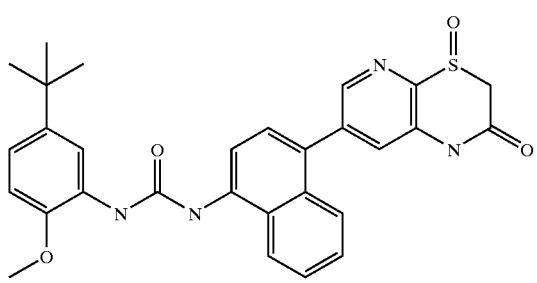

1-(5-tert-Butyl-2-methoxy-phenyl)-3-[4-(2,4-dioxo-1,2,3,4-tetrahydro-4-lambda-4-pyrido[2,3-b][1,4]thiazin-7-yl)-naphthalen-1-yl]-urea;

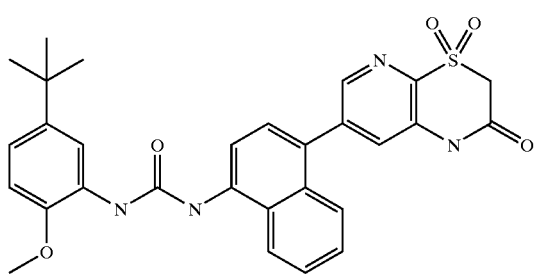

1-(5-tert-Butyl-2-methoxy-phenyl)-3-[4-(2,4,4-trioxo-1,2,3,4-tetrahydro-4-lambda-6-pyrido[2,3-b][1,4]thiazin-7-yl)-naphthalen-1-yl]-urea;

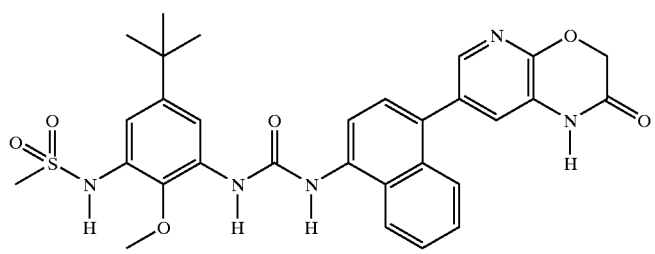

N-(5-tert-Butyl-2-methoxy-3-{3-[4-(2-oxo-2,3-dihydro-1H-pyrido[2,3-b][1,4]oxazin-7-yl)-naphthalen-1-yl]-ureido}-phenyl)-methanesulfonamide;

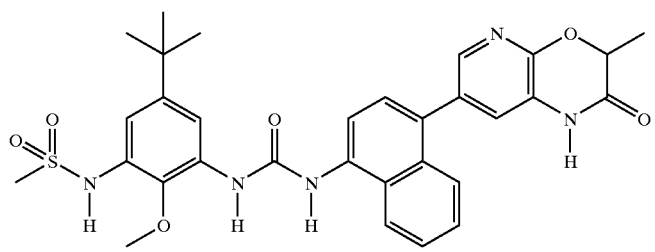

N-(5-tert-Butyl-2-methoxy-3-{3-[4-(3-methyl-2-oxo-2,3-dihydro-1H-pyrido[2,3-b][1,4]oxazin-7-yl)-naphthalen-1-yl]-ureido}-phenyl)-methanesulfonamide;

TABLE I-continued

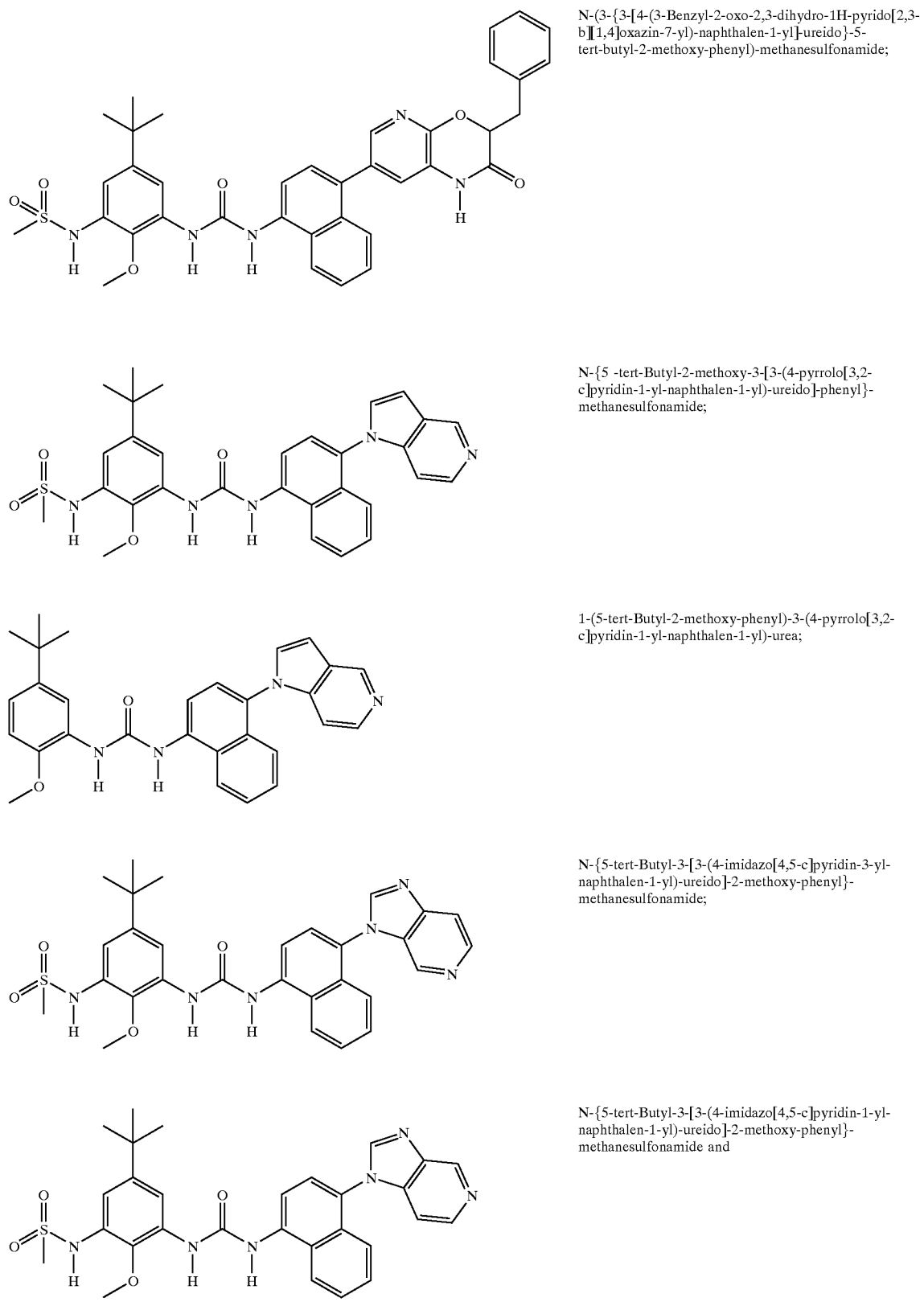

N-(3-{3-[4-(3-Benzyl-2-oxo-2,3-dihydro-1H-pyrido[2,3-b][1,4]oxazin-7-yl)-naphthalen-1-yl]-ureido}-5-tert-butyl-2-methoxy-phenyl)-methanesulfonamide;

N-{5-tert-Butyl-2-methoxy-3-[3-(4-pyrrolo[3,2-c]pyridin-1-yl-naphthalen-1-yl)-ureido]-phenyl}-methanesulfonamide;

1-(5-tert-Butyl-2-methoxy-phenyl)-3-(4-pyrrolo[3,2-c]pyridin-1-yl-naphthalen-1-yl)-urea;

N-{5-tert-Butyl-3-[3-(4-imidazo[4,5-c]pyridin-3-yl-naphthalen-1-yl)-ureido]-2-methoxy-phenyl}-methanesulfonamide;

N-{5-tert-Butyl-3-[3-(4-imidazo[4,5-c]pyridin-1-yl-naphthalen-1-yl)-ureido]-2-methoxy-phenyl}-methanesulfonamide and the pharmaceutically acceptable derivatives thereof.

Table II contains representative compounds of the invention which can be made by according to the general methods and examples in the sections below.

TABLE II

| Structure | Name |
|---|---|
| 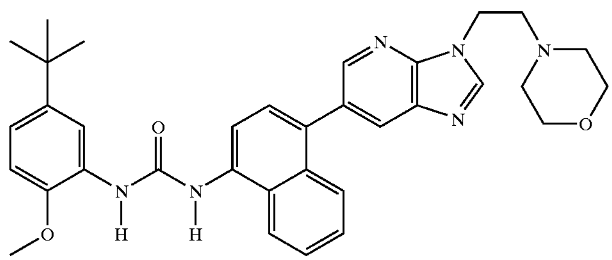 | 1-(5-tert-Butyl-2-methoxy-phenyl)-3-{4-[3-(2-morpholin-4-yl-ethyl)-3H-imidazo[4,5-b]pyridin-6-yl]-naphthalen-1-yl}-urea; |
| 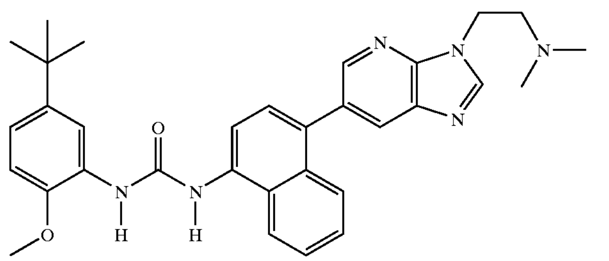 | 1-(5-tert-Butyl-2-methoxy-phenyl)-3-{4-[3-(2-dimethylamino-ethyl)-3H-imidazo[4,5-b]pyridin-6-yl]-naphthalen-1-yl}-urea; |
| 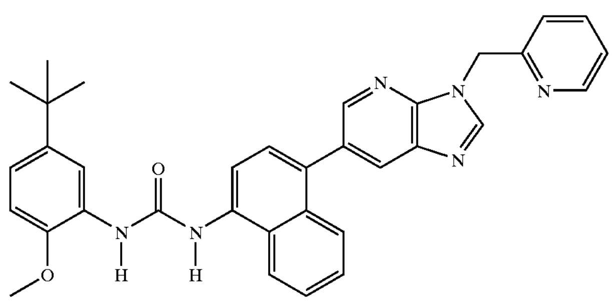 | 1-(5-tert-Butyl-2-methoxy-phenyl)-3-[4-(3-pyridin-2-ylmethyl-3H-imidazo[4,5-b]pyridin-6-yl)-naphthalen-1-yl]-urea; |
| 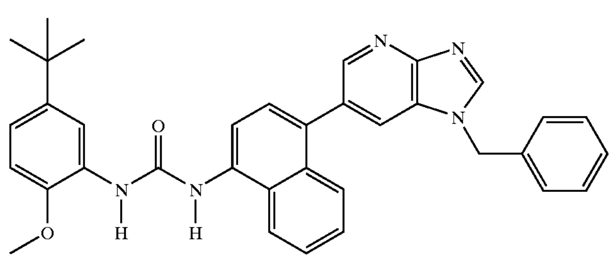 | 1-[4-(1-Benzyl-1H-imidazo[4,5-b]pyridin-6-yl)-naphthalen-1-yl]-3-(5-tert-butyl-2-methoxy-phenyl)-urea; |
| 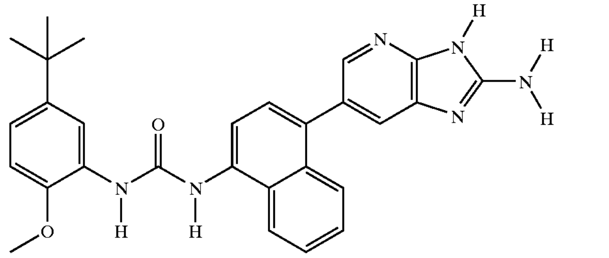 | 1-[4-(2-Amino-3H-imidazo[4,5-b]pyridin-6-yl)-naphthalen-1-yl]-3-(5-tert-butyl-2-methoxy-phenyl)-urea; |

TABLE II-continued

| | |
|---|---|
| 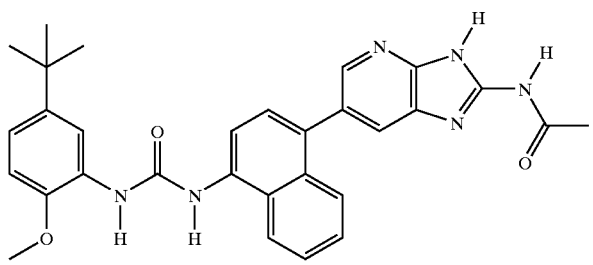 | N-(6-{4-[3-(5-tert-Butyl-2-methoxy-phenyl)-ureido]-naphthalen-1-yl}-3H-imidazo[4,5-b]pyridin-2-yl)-acetamide; |
| 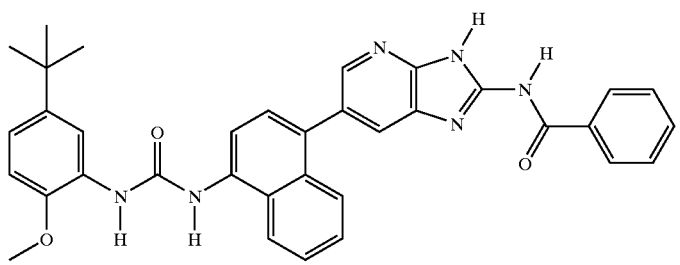 | N-(6-{4-[3-(5-tert-Butyl-2-methoxy-phenyl)-ureido]-naphthalen-1-yl}-3H-imidazo[4,5-b]pyridin-2-yl)-benzamide; |
| 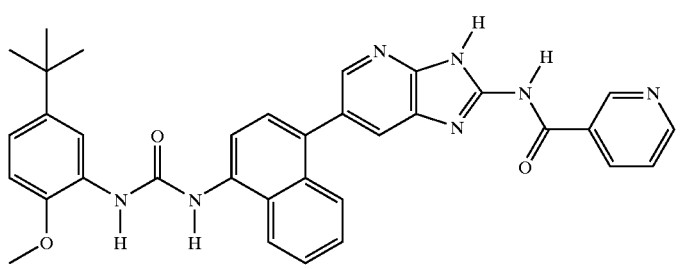 | N-(6-{4-[3-(5-tert-Butyl-2-methoxy-phenyl)-ureido]-naphthalen-1-yl}-3H-imidazo[4,5-b]pyridin-2-yl)-nicotinamide; |
| 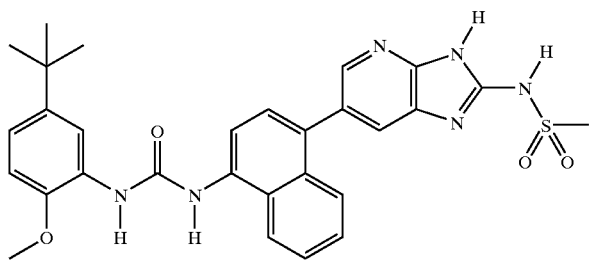 | N-(6-{4-[3-(5-tert-Butyl-2-methoxy-phenyl)-ureido]-naphthalen-1-yl}-3H-imidazo[4,5-b]pyridin-2-yl)-methanesulfonamide; |
| 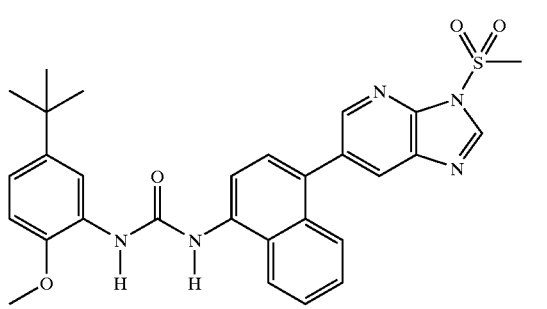 | 1-(5-tert-Butyl-2-methoxy-phenyl)-3-[4-(3-methanesulfonyl-3H-imidazo[4,5-b]pyridin-6-yl)-naphthalen-1-yl]-urea; |

TABLE II-continued

| Structure | Name |
|---|---|
| | 1-(5-tert-Butyl-2-methoxy-phenyl)-3-[4-(2-diethylaminomethyl-3H-imidazo[4,5-b]pyridin-6-yl)-naphthalen-1-yl]-urea; |
| | 1-(5-tert-Butyl-2-methoxy-phenyl)-3-[4-(2-pyrrolidin-1-ylmethyl-3H-imidazo[4,5-b]pyridin-6-yl)-naphthalen-1-yl]-urea; |
| | 1-(5-tert-Butyl-2-methoxy-phenyl)-3-{4-[2-(4-methyl-piperazin-1-ylmethyl)-3H-imidazo[4,5-b]pyridin-6-yl]-naphthalen-1-yl}-urea; |
| | 1-(5-tert-Butyl-2-methoxy-phenyl)-3-[4-(2-oxo-2,3-dihydro-1H-imidazo[4,5-b]pyridin-6-yl)-naphthalen-1-yl]-urea; |
| | 1-(5-tert-Butyl-2-methoxy-phenyl)-3-[4-(2,3-dioxo-1,2,3,4-tetrahydro-pyrido[2,3-b]pyrazin-7-yl)-naphthalen-1-yl]-urea; |
| | 1-[4-(3-Benzyl-2-oxo-2,3-dihydro-1H-pyrido[2,3-b][1,4]oxazin-7-yl)-naphthalen-1-yl]-3-(5-tert-butyl-2-methoxy-phenyl)-urea; |

TABLE II-continued

| | |
|---|---|
| 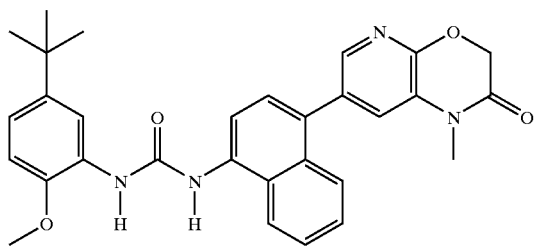 | 1-(5-tert-Butyl-2-methoxy-phenyl)-3-[4-(1-methyl-2-oxo-2,3-dihydro-1H-pyrido[2,3-b][1,4]oxazin-7-yl)-naphthalen-1-yl]-urea; |
| 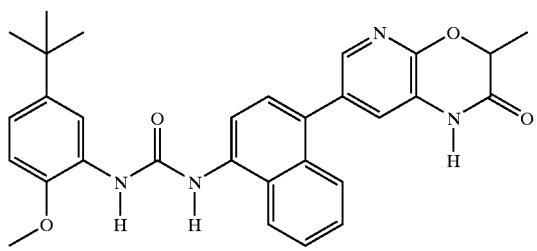 | 1-(5-tert-Butyl-2-methoxy-phenyl)-3-[4-(3-methyl-2-oxo-2,3-dihydro-1H-pyrido[2,3-b][1,4]oxazin-7-yl)-naphthalen-1-yl]-urea; |
| 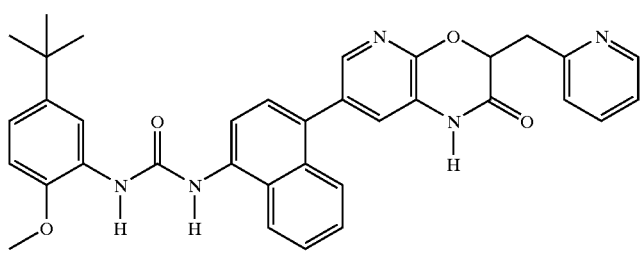 | 1-(5-tert-Butyl-2-methoxy-phenyl)-3-[4-(2-oxo-3-pyridin-2-ylmethyl-2,3-dihydro-1H-pyrido[2,3-b][1,4]oxazin-7-yl)-naphthalen-1-yl]-urea; |
| 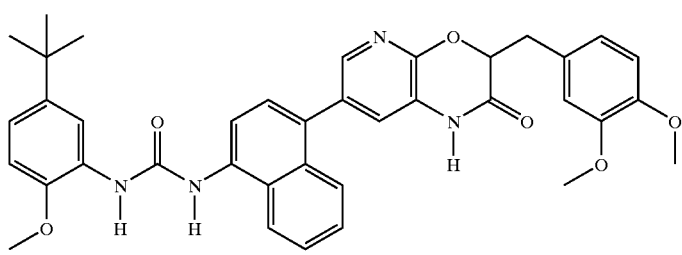 | 1-(5-tert-Butyl-2-methoxy-phenyl)-3-{4-[3-(3,4-dimethoxy-benzyl)-2-oxo-2,3-dihydro-1H-pyrido[2,3-b][1,4]oxazin-7-yl]-naphthalen-1-yl}-urea; |
| 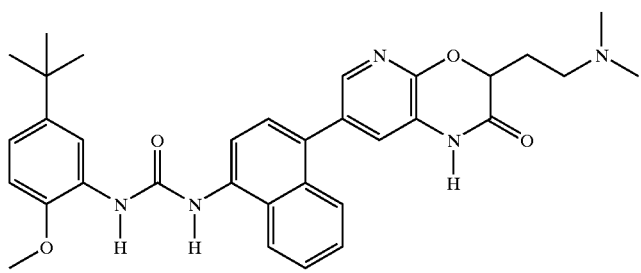 | 1-(5-tert-Butyl-2-methoxy-phenyl)-3-{4-[3-(2-dimethylamino-ethyl)-2-oxo-2,3-dihydro-1H-pyrido[2,3-b][1,4]oxazin-7-yl]-naphthalen-1-yl}-urea; |
| 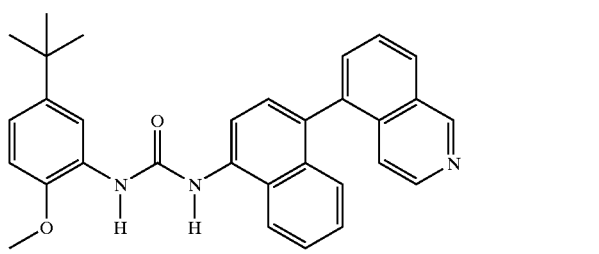 | 1-(5-tert-Butyl-2-methoxy-phenyl)-3-(4-isoquinolin-5-yl-naphthalen-1-yl)-urea; |

TABLE II-continued

| Structure | Name |
|---|---|
| | 1-(5-tert-Butyl-2-methoxy-phenyl)-3-(4-purin-9-yl-naphthalen-1-yl)-urea; |
| | 1-(5-tert-Butyl-2-methoxy-phenyl)-3-(4-purin-7-yl-naphthalen-1-yl)-urea; |
| | 1-[4-(6-Amino-purin-9-yl)-naphthalen-1-yl]-3-(5-tert-butyl-2-methoxy-phenyl)-urea; |
| | 1-(5-tert-Butyl-2-methoxy-phenyl)-3-[4-(6-methylamino-purin-9-yl)-naphthalen-1-yl]-urea; |
| | 1-(5-tert-Butyl-2-methoxy-phenyl)-3-[4-(6-dimethylamino-purin-9-yl)-naphthalen-1-yl]-urea; |
| | 1-(5-tert-Butyl-2-methoxy-phenyl)-3-[4-(6-cyclopropylamino-purin-9-yl)-naphthalen-1-yl]-urea; |

TABLE II-continued

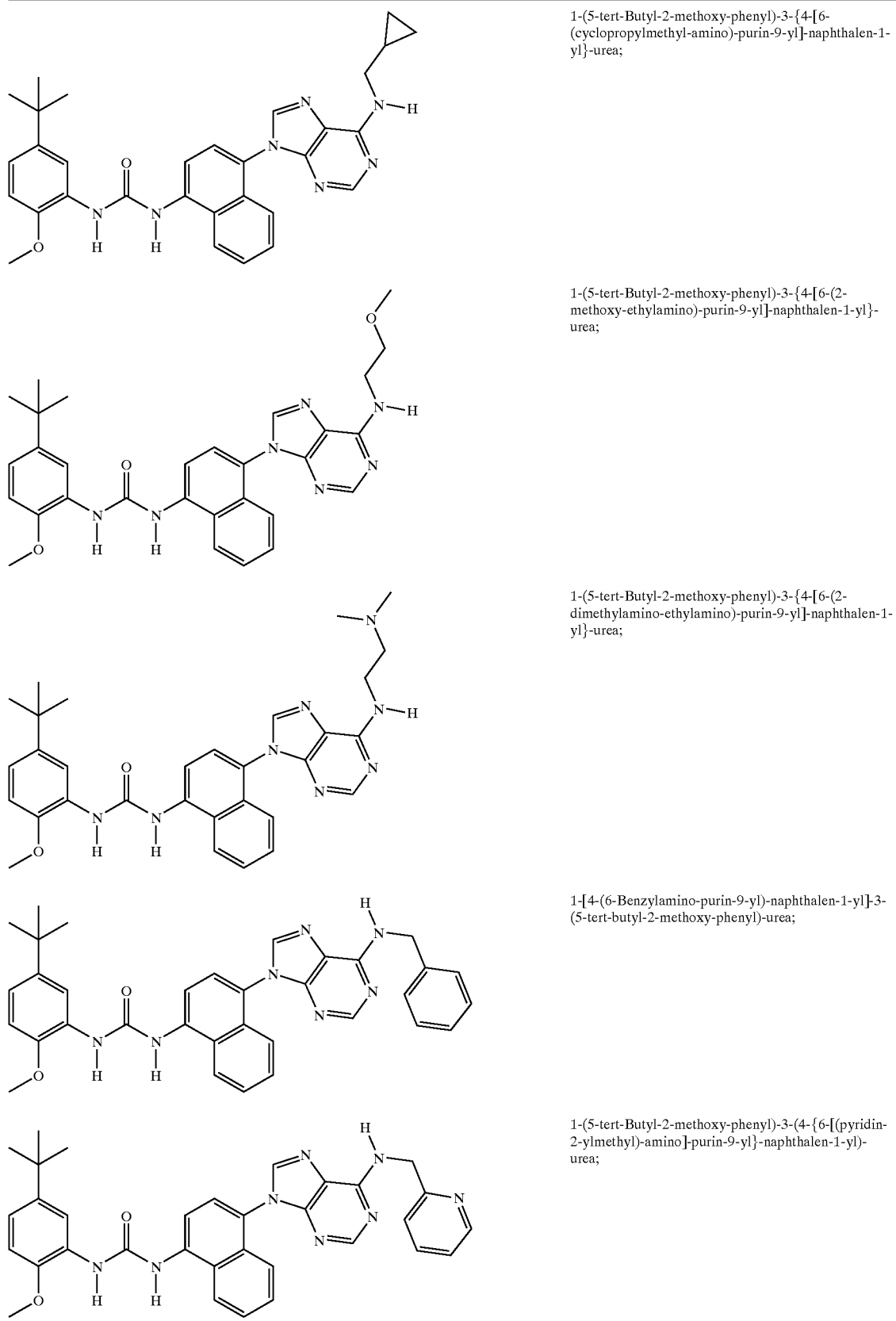

1-(5-tert-Butyl-2-methoxy-phenyl)-3-{4-[6-(cyclopropylmethyl-amino)-purin-9-yl]-naphthalen-1-yl}-urea;

1-(5-tert-Butyl-2-methoxy-phenyl)-3-{4-[6-(2-methoxy-ethylamino)-purin-9-yl]-naphthalen-1-yl}-urea;

1-(5-tert-Butyl-2-methoxy-phenyl)-3-{4-[6-(2-dimethylamino-ethylamino)-purin-9-yl]-naphthalen-1-yl}-urea;

1-[4-(6-Benzylamino-purin-9-yl)-naphthalen-1-yl]-3-(5-tert-butyl-2-methoxy-phenyl)-urea;

1-(5-tert-Butyl-2-methoxy-phenyl)-3-(4-{6-[(pyridin-2-ylmethyl)-amino]-purin-9-yl}-naphthalen-1-yl)-urea;

TABLE II-continued

| Structure | Name |
|---|---|
| 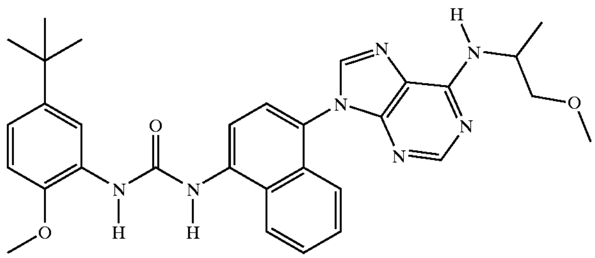 | 1-(5-tert-Butyl-2-methoxy-phenyl)-3-{4-[6-(2-methoxy-1-methyl-ethylamino)-purin-9-yl]-naphthalen-1-yl}-urea; |
| 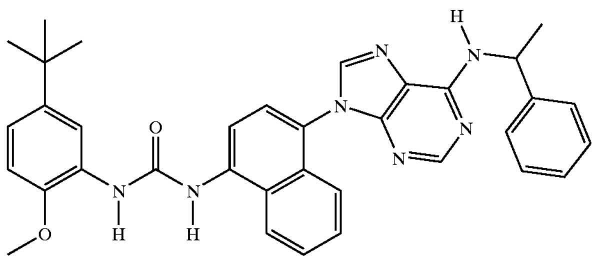 | 1-(5-tert-Butyl-2-methoxy-phenyl)-3-{4-[6-(1-phenyl-ethylamino)-purin-9-yl]-naphthalen-1-yl}-urea; |
| 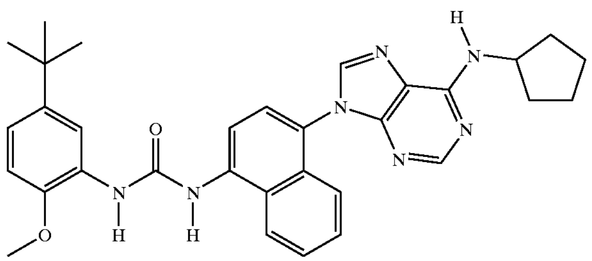 | 1-(5-tert-Butyl-2-methoxy-phenyl)-3-[4-(6-cyclopentylamino-purin-9-yl)-naphthalen-1-yl]-urea; |
| 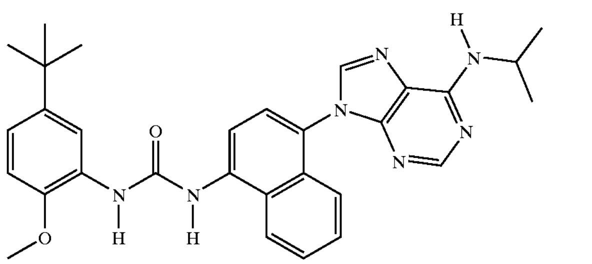 | 1-(5-tert-Butyl-2-methoxy-phenyl)-3-[4-(6-isopropylamino-purin-9-yl)-naphthalen-1-yl]-urea; |
| 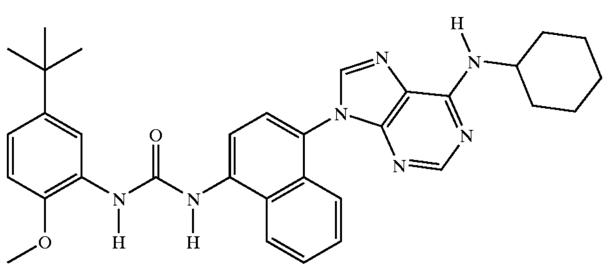 | 1-(5-tert-Butyl-2-methoxy-phenyl)-3-[4-(6-cyclohexylamino-purin-9-yl)-naphthalen-1-yl]-urea; |
| 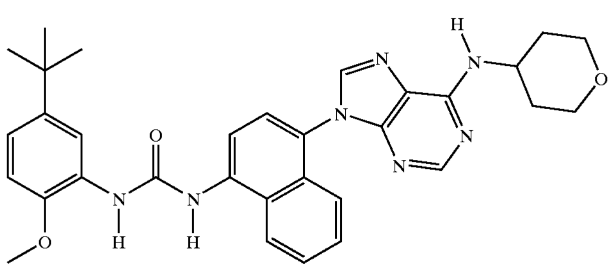 | 1-(5-tert-Butyl-2-methoxy-phenyl)-3-{4-[6-(tetrahydro-pyran-4-ylamino)-purin-9-yl]-naphthalen-1-yl}-urea; |

TABLE II-continued

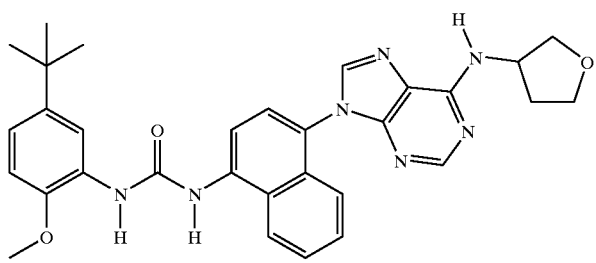

1-(5-tert-Butyl-2-methoxy-phenyl)-3-{4-[6-(tetrahydro-furan-3-ylamino)-purin-9-yl]-naphthalen-1-yl}-urea;

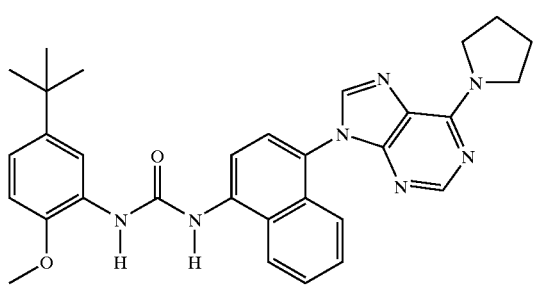

1-(5-tert-Butyl-2-methoxy-phenyl)-3-[4-(6-pyrrolidin-1-yl-purin-9-yl)-naphthalen-1-yl]-urea;

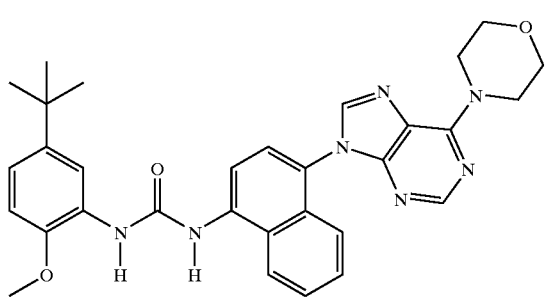

1-(5-tert-Butyl-2-methoxy-phenyl)-3-[4-(6-morpholin-4-yl-purin-9-yl)-naphthalen-1-yl]-urea;

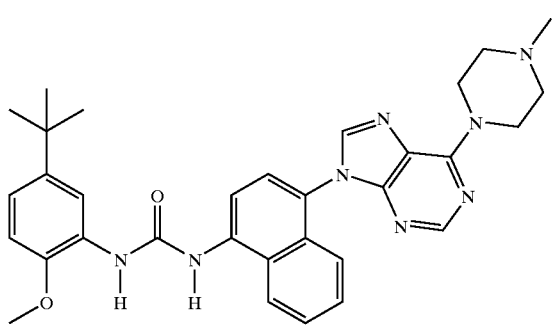

1-(5-tert-Butyl-2-methoxy-phenyl)-3-{4-[6-(4-methyl-piperazin-1-yl)-purin-9-yl]-naphthalen-1-yl}-urea;

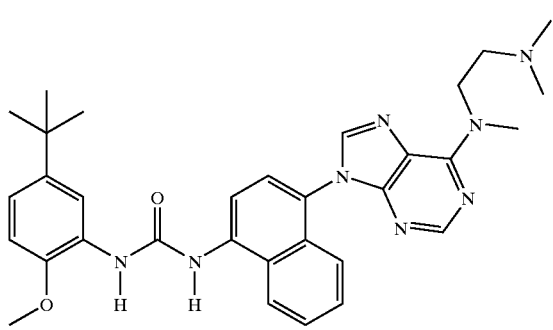

1-(5-tert-Butyl-2-methoxy-phenyl)-3-(4-{6-[(2-dimethylamino-ethyl)-methyl-amino]-purin-9-yl}-naphthalen-1-yl)-urea;

TABLE II-continued

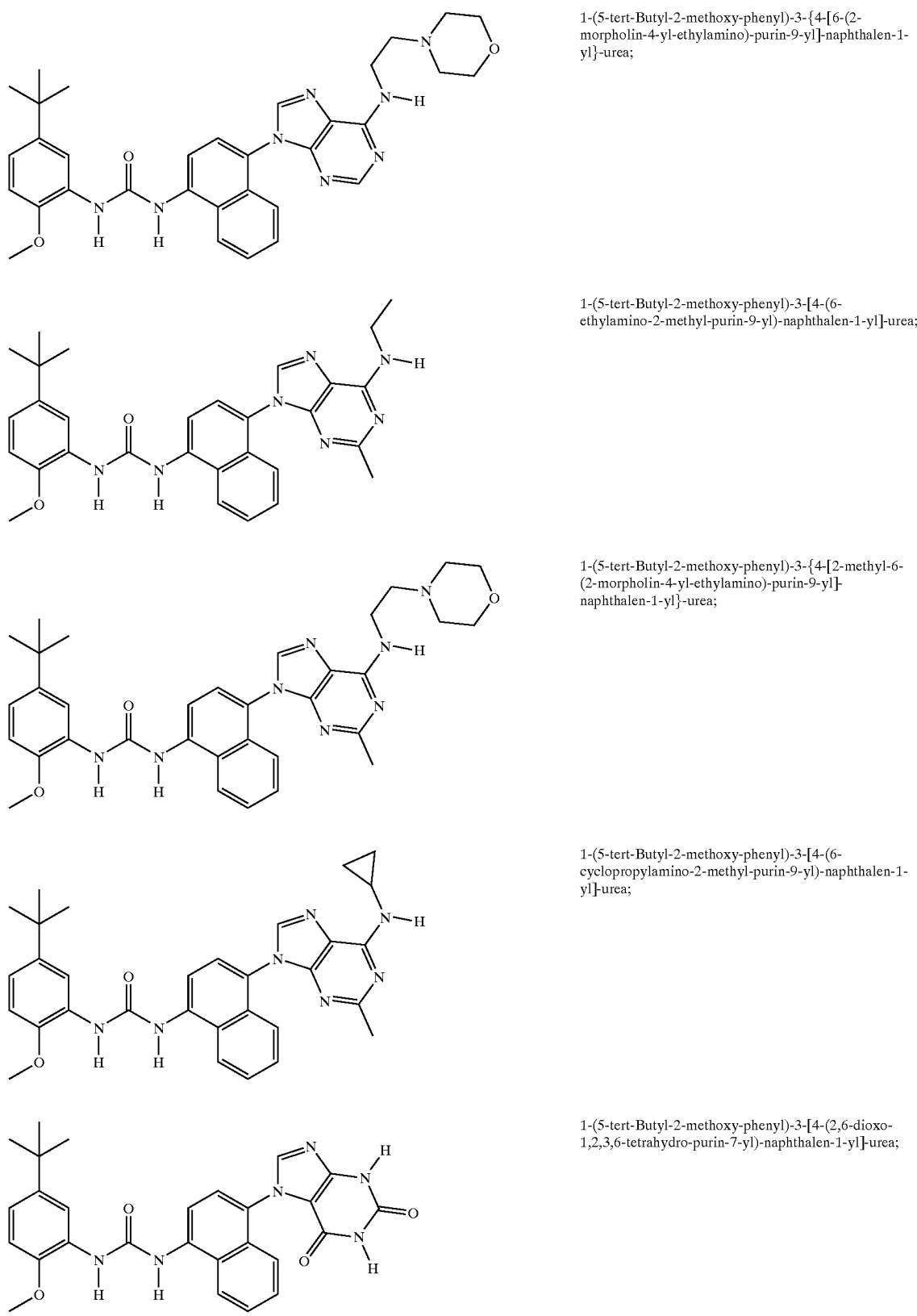

1-(5-tert-Butyl-2-methoxy-phenyl)-3-{4-[6-(2-morpholin-4-yl-ethylamino)-purin-9-yl]-naphthalen-1-yl}-urea;

1-(5-tert-Butyl-2-methoxy-phenyl)-3-[4-(6-ethylamino-2-methyl-purin-9-yl)-naphthalen-1-yl]-urea;

1-(5-tert-Butyl-2-methoxy-phenyl)-3-{4-[2-methyl-6-(2-morpholin-4-yl-ethylamino)-purin-9-yl]-naphthalen-1-yl}-urea;

1-(5-tert-Butyl-2-methoxy-phenyl)-3-[4-(6-cyclopropylamino-2-methyl-purin-9-yl)-naphthalen-1-yl]-urea;

1-(5-tert-Butyl-2-methoxy-phenyl)-3-[4-(2,6-dioxo-1,2,3,6-tetrahydro-purin-7-yl)-naphthalen-1-yl]-urea;

TABLE II-continued

| Structure | Name |
|---|---|
| 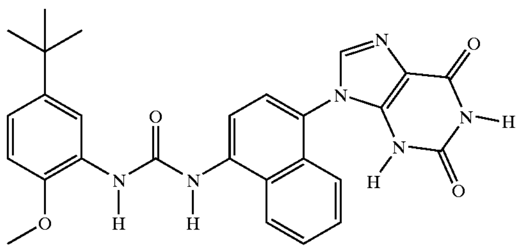 | 1-(5-tert-Butyl-2-methoxy-phenyl)-3-[4-(2,6-dioxo-1,2,3,6-tetrahydro-purin-9-yl)-naphthalen-1-yl]-urea; |
| | 1-(5-tert-Butyl-2-methoxy-phenyl)-3-(4-pyrazolo[3,4-d]pyrimidin-1-yl-naphthalen-1-yl)-urea and | the pharmaceutically acceptable derivatives thereof.

In another distinct embodiment, there is also provided the following compound possessing anticytokine activity:

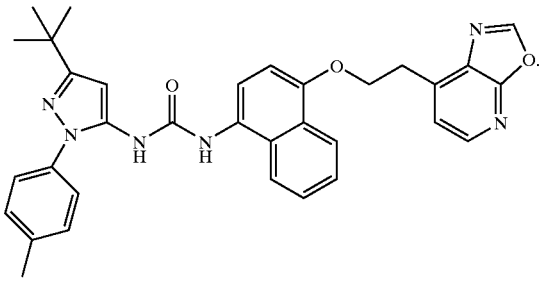

In all the compounds disclosed hereinabove in this application, in the event the nomenclature is in conflict with the structure, it shall be understood that the compound is defined by the structure.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formulas (I) & (II) can exist in more than one tautomeric form. The invention includes all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, and butoxy. All alkyl, alkenyl and alkynyl groups shall be understood as being $C_{1-10}$ branched or unbranched where structurally possible and unless otherwise specified. Other more specific definitions are as follows:

The term "aroyl" as used in the present specification shall be understood to mean "benzoyl" or "naphthoyl".

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic or non-aromatic ring systems. The non-aromatic ring systems may be mono- or polyunsaturated. Preferred carbocycles unless otherwise specified include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl.

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Preferred heterocycles include but are not limited to, for example pyrrolidinyl, tetrahydrofuranyl, tetrahydrothiophenyl, piperidinyl, piperazinyl, morpholinyl, tetrahydropyranyl, dioxanyl, oxazolinyl, thiazolinyl, imidazolinyl, tetrahydropyridinyl, homopiperidinyl, pyrrolinyl, tetrahydropyrimidinyl, decahydroquinolinyl, decahydroisoquinolinyl, thiomorpholinyl, thiazolidinyl.

The term "heteroaryl" shall be understood to mean an aromatic 5–8 membered monocyclic or 8–11 membered bicyclic ring containing 1–4 heteroatoms chosen from N, O and S. Included are the partially or fully saturated derivates thereof. Such heteroaryls unless otherwise specified include: pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl and indazolyl.

The term "heteroatom" as used herein shall be understood to mean atoms other than carbon such as O, N, S and P.

In all alkyl groups or carbon chains where one or more carbon atoms are optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by oxo to result in definitions such as but not limited to: acyl, alkoxycarbonyl, alkylthiosulfone, alkylthiosulfonyl, amido etc.

The term "aryl" as used herein unless otherwise specified shall be understood to mean aromatic carbocycle or heteroaryl as defined herein.

Terms which are analogs of the above cyclic moieties such as aryloxy, heterocyclyloxy or heteroaryl amine shall be understood to mean an aryl, heteroaryl, heterocycle as defined above attached to it's respective group.

As used herein, "nitrogen" and "sulfur" include any oxidized form of nitrogen and sulfur and the quaternized form of any basic nitrogen. For example, if Y is —S—$C_{1-6}$ alkyl, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine.

The compounds of the invention are only those which are contemplated to be 'chemically stable' as will be appreciated by those skilled in the art. For example, a compound which would have a 'dangling valency', or a 'carbanion' are not compounds contemplated by the invention.

The invention includes pharmaceutically acceptable derivatives of compounds of formulas (I) & (II). A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof. A pharmacologically active metabolite shall be understood to mean any compound of the formula(I) capable of being metabolized enzymatically or chemically. This includes, for example, hydroxylated or oxidized derivative compounds of the formulas (I)/(II).

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N-($C_1$–$C_4$ alkyl)$_4^+$ salts.

In addition, the compounds of this invention include prodrugs of compounds of the formulas (I) & (II). Prodrugs include those compounds that, upon simple chemical transformation, are modified to produce compounds of the invention. Simple chemical transformations include hydrolysis, oxidation and reduction. Specifically, when a prodrug of this invention is administered to a patient, the prodrug may be transformed into a compound of formulas (I) & (II), thereby imparting the desired pharmacological effect.

Methods of Use

In accordance with the invention, there are provided methods of using the compounds of the formulas (I) & (II).

The compounds of the invention effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of diseases and conditions as described in the Background section, including the following conditions and diseases: osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, toxic shock syndrome, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entreocolitis, complications including restenosis following percutaneous transluminal coronary angioplasty, traumatic arthritis, sepsis, chronic obstructive pulmonary disease and congestive heart failure.

In addition, the compounds of the invention being inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., Proc. Natl. Acad. Sci. U.S.A, 1992, 89, 4888.) Accordingly, the present novel compounds would be expected to exhibit efficacy against those disorders currently treated with COX inhibitors such as the familiar NSAIDs. These disorders include acute and chronic pain as well as symptoms of inflammation and cardiovascular disease.

As discussed in the Background of the Invention, IL-8 plays a role in the influx of neutrophils into sites of inflammation or injury. Therefore, in a yet further aspect of the invention, the compounds of the invention may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formulas (I) & (II) (w/w) or a combination thereof. The optimum percentage (w/w) of a compound of the invention may vary and is within the purview of those skilled in the art.

Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known. Reference in this regard may be made to H. C. Ansel and N. G. Popovish, *Pharmaceutical Dosage Forms and Drug Delivery Systems*, 5th ed., Lea and Febiger (1990), Cappola et al. U.S. application Ser. No. 09/902,822 and U.S. provisional application ser. No. 60/313, 527. Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. Reference in this regard may also be made to U.S. provisional application No. 60/339,249. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

General Synthetic Methods

The invention additionally provides for methods of making the compounds of the formulas (I) & (II). The compounds of the invention may be prepared by the general methods and examples presented below, and methods known to those of ordinary skill in the art. Further reference in this regard may be made to U.S. Pat. No. 6,297,381, U.S. application Ser. Nos. 09/505,582, 09/484,638, 09/735,160, 09/902,085, 09/698,442, 09/834,797, 09/611,109, U.S. provisional application Nos. 60/206,327, 60/216,283, 60/295, 909, 60/293,600, 60/291,425, 60/283,642 and 60/268,841. Each of the aforementioned are incorporated herein by reference in their entirety.

In all schemes "G" in the formulas shown below shall have the meaning of "G" in the formulas (I) and (II) of the invention described hereinabove. "G'" (G prime) shall have the meaning of

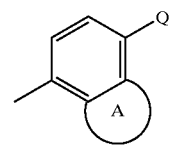

in the formulas (I) and (II) or a precursor of that moiety.

The compounds of the invention may be prepared by Method A, B, C or D as illustrated in Scheme I, preferably Method C.

Scheme I

Method A

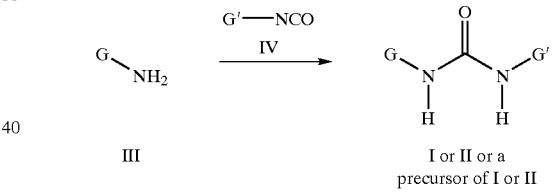

Method B

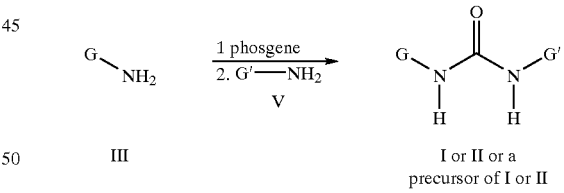

Method C

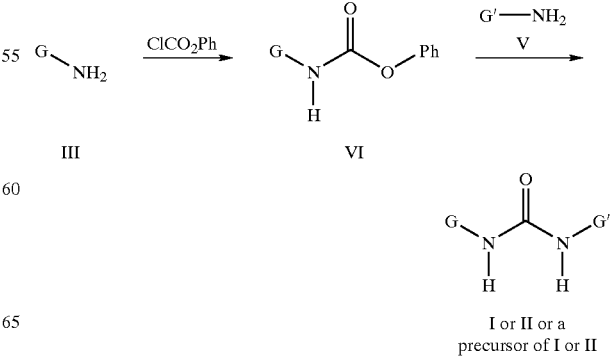

Method D

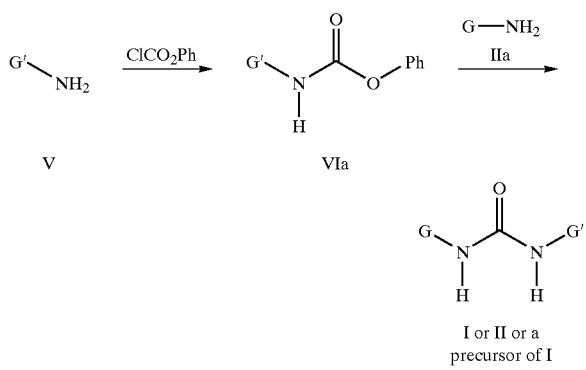

In Method A, a mixture of an arylamine of formula III and an arylisocyanate of formula IV is dissolved in a non-protic, anhydrous solvent such as THF, ether, toluene, dioxane or ethyl acetate. The preferred solvent is THF. The mixture is stirred at between 0–45° C., preferably at 25° C., for 2–24 h, and the volatiles are removed. Purification of the residue by recrystallization from an appropriate solvent such as ethyl acetate/hexanes, ethyl acetate/MeOH, THF/petroleum ether, EtOH/water or by silica gel chromatography, using for example, hexanes and ethyl acetate as eluents, provides the product of formula I or II or precursors thereof.

In Method B, an arylamine of formula III is dissolved in a halogenated solvent, such as methylene chloride, chloroform or dichloroethane. The preferred solvent is methylene chloride. The mixture is diluted with aqueous alkali, such as sodium bicarbonate or potassium carbonate, cooled in an ice bath and phosgene is added. The mixture is vigorously stirred for 5–30 min, with 10 min being preferable. The organic layer is dried, with agents such as $MgSO_4$ or $Na_2SO_4$, and the volatiles removed to provide the corresponding isocyanate. The isocyanate and arylamine IV are mixed in a non-protic, anhydrous solvent such as THF, ether, toluene, dioxane, methylene chloride or ethyl acetate. The preferred solvent is THF. The mixture is stirred at between 0–45° C., preferably at 25° C., for 2–24 h, and the volatiles are removed. Purification of the residue by recrystallization or by silica gel chromatography, as above, provides the product of formula I or II or precursors thereof.

The required isocyanate may also be prepared from the carboxylic acid $G-CO_2H$ by reaction with a chloroformate, such as ethyl chloroformate, in the presence of a suitable base, such as triethylamine, in a suitable solvent, such as THF at about 0° C. The resulting mixed anhydride is treated with an aqueous solution of sodium azide. Heating a solution of the resulting acyl azide in a suitable solvent, such as toluene, at about reflux, results in a Curtius rearrangement, providing the isocyanate G—N═C═O in situ.

In Method C, an arylamine of formula III is dissolved in a suitable solvent such as a halogenated solvent which includes methylene chloride, chloroform or dichloroethane. The preferred solvent is methylene chloride. A suitable base such as triethylamine may be added, followed by an alkyl or aryl chloroformate, such as t-butyl chloroformate or phenyl chloroformate (shown). The mixture is stirred at between 0–85° C., preferably at reflux temperature, for 2–24 h, and the volatiles are removed providing carbamate VI. The carbamate and arylamine V are mixed in a non-protic, anhydrous solvent such as DMSO, THF, ether, toluene, dioxane, methylene chloride or ethyl acetate. The mixture is stirred at between 0–110° C., preferably at between about 50° C. and reflux temperature, for 2–24 h, and the volatiles are removed. Purification of the residue as above provides the product of formula I or II or precursors thereof. This process can also be performed in the reverse sense as illustrated by Method D.

Arylamine intermediates of formula III are either commercially available or can be made by methods known to those skilled in the art. Further reference in this regard may be made to the U.S. applications cited in the first paragraph of this section. Methods by which intermediates IV and V may be prepared are also known to those skilled in the art. Some of these methods are exemplified below.

SYNTHETIC EXAMPLES

Example 1

Synthesis of 1-(4-aminonaphthalen-1-yl)pyrrolo[3,2-c]pyridine

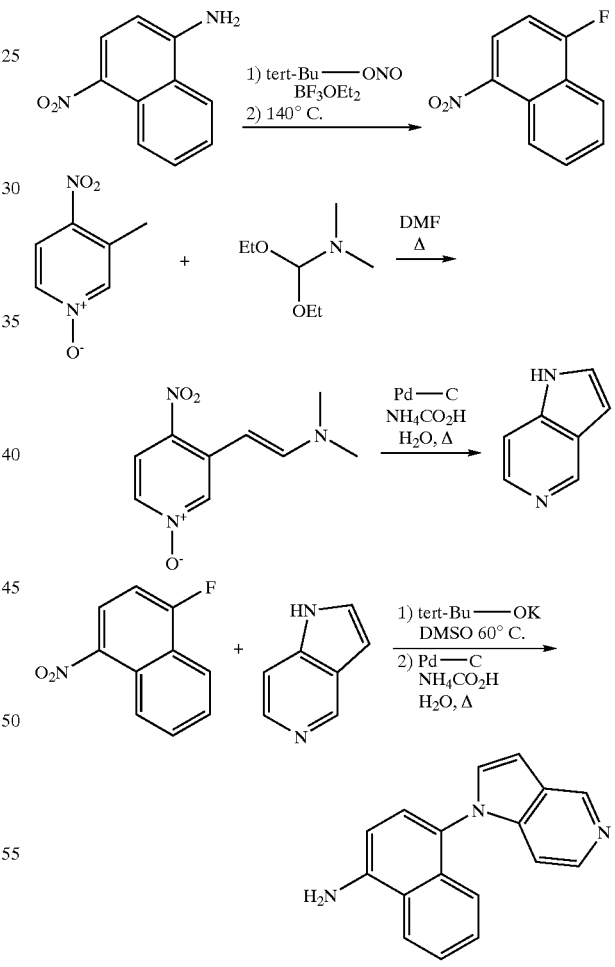

1

In a dry round-bottom flask under inert atmosphere and equipped with a magnetic stirrer bar was added boron trifluoride etherate (2.65 mL, 20.93 mmol, 1.5 equiv.). To this reagent cooled to 0° C. a solution on 4-nitro-1-naphthylamine (2.626 g, 13.95 mmol, 1 equiv.) in 39 mL anhydrous DME was slowly added via syringe. 15 min after the addition was complete, a solution of tert-butyl nitrite (2.00 mL, 16.74 mmol, 1.2 equiv.) in 15 mL anhydrous DME was added dropwise via syringe. The mixture was allowed to reach room temperature and stir 1 h. The reaction was then cooled to 0° C. without stirring. The precipitated green/gold diazonium tetrafluoroborate salt was collected by filtration (3.858 g, 13.44 mmol, 96%).

The nitronaphthalene diazonium tetrafluoroborate salt from above (3.448 g, 12.0 mmol, 1 equiv.) was suspended in 100 mL xylenes, heated to reflux for 1 h, then allowed to cool back to room temperature. Water was then added and the product extracted twice with ether. The combined extracts were dried (MgSO₄), filtered, and the solvents were removed in vacuo. The crude product was purified by column chromatography on SiO₂ using 10% EtOAc in hexanes as eluent, providing 1.95 g of 4-fluoro-1-nitronaphthalene (10.20 mmol, 85% yield).

3-Methyl-4-nitro-pyridine-N-oxide (5.34 g, 34.7 mmol, 1 equiv.) and N,N-dimethylformamide diethyl acetal (10.5 mL, 61.4 mmol, 1.8 equiv.) were combined in 50 mL anhydrous DMF and heated to 120° C. for 3 h. The reaction was allowed to cool back to room temperature and the DMF solvent was removed in vacuo. The residue was treated with ~80 mL toluene, which was then removed in vacuo as well. Finally the residue was mixed with benzene and filtered. The desired vinyl amine was obtained as a dark purple solid (6.74 g, 32.2 mmol, 93%), which was used as is in the next step.

The vinyl amine from above (3.37 g, 16.1 mmol, 1 equiv.) and 1.75 mL of water were mixed in 50 mL EtOH. Ammonium formate (4.56 g, 72.5 mmol) and 10% palladium-on-carbon (600 mg) were added and the mixture was heated to a gentle reflux for 1 h. TLC and MS (ES+) revealed no starting material but showed the presence of two major components, the desired 5-aza-indole and its N-oxide. The reaction was left stirring for a further 2 h after more ammonium formate and more palladium catalyst were added. Finally the reaction was cooled to room temperature, filtered and solvents removed in vacuo. 5% NaOH aqueous solution was added and the mixture was extracted with EtOAc. The combined organics were dried (MgSO₄), filtered, and the solvent was removed in vacuo, providing 0.555 g of desired 5-aza-indole (4.70 mmol, 29% yield).

The 5-aza-indole from above (425 mg, 3.60 mmol, 1 equiv.) was added to potassium tert-butoxide (404 mg, 3.60 mmol, 1 equiv.) in 7.0 mL anhydrous DMSO at room temperature. When all solids had completely dissolved (brown color present), 4-fluoro-1-nitro-naphthalene from above (688 mg, 3.60 mmol, 1 equiv.) was added and the mixture was heated to 60° C. for 15 min. The reaction was allowed to cool, quenched with saturated aqueous NaHCO₃ solution and extracted repeatedly with EtOAc. The combined extracts were washed twice with water and once with brine, then dried (MgSO₄), filtered and the solvent removed in vacuo. The desired product was purified by a short column of SiO₂, using 3% MeOH in dichloromethane as eluent providing 650 mg of the 4-indolo-1-nitronaphthalene derivative (2.25 mmol, 62%).

The 4-indolo-1-nitronaphthalene from above (167 mg, 0.58 mmol, 1 equiv.) was dissolved in 12 mL EtOH and 12 mL EtOAc. Ammonium formate (218 mg, 3.46 mmol, 6 equiv.) and 10% palladium-on-carbon (60 mg) were then added and the mixture was gently refluxed for 20 min. The reaction was allowed to cool, filtered, the catalyst washed with with EtOAc and solvents removed in vacuo providing a light tan foam (206 mg). This was taken up in dichloromethane and filtered through 0.45 um membrane to remove left over traces of ammonium formate. Concentration of the filtrate gave 142 mg (0.55 mmol, 94%) of the title compound.

Example 2

Synthesis of 1-(5-tert-butyl-2-p-tolyl-2H-pyrazol-3-yl)-3-(4-pyrrolo[3,2-c]pyridin-1-yl-naphthalen-1-yl)-urea

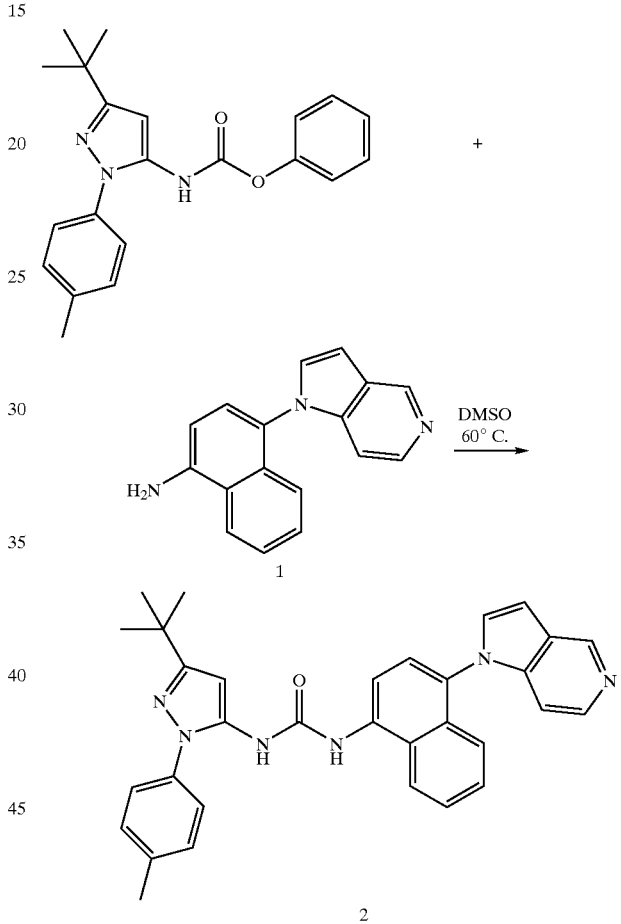

(5-tert-Butyl-2-p-tolyl-2H-pyrazol-3-yl)-carbamic acid phenyl ester (144 mg, 0.411 mmol, 1.1 equiv.) and 1-(4-aminonaphthalen-1-yl)pyrrolo[3,2-c]pyridine (Example 1) (97 mg, 0.374 mmol, 1 equiv.) were combined in 2 mL anhydrous DMSO. The mixture was stirred under inert atmosphere for 1.5 h, then heated to 60° C. for 0.5 h. The reaction was allowed to cool, quenched with 5% aqueous NaOH and extracted with EtOAc three times. The combined organic extracts were washed with water, then brine. They were then dried (MgSO₄), filtered, and the solvents were removed in vacuo. The residue was purified by column chromatography using 3–4% MeOH in dichloromethane providing 161 mg title compound (0.313 mmol, 84%) as a glassy solid.

Example 3

Synthesis of 1-(5-tert-butyl-2-methoxy-phenyl)-3-(4-pyrrolo[3,2-c]pyridin-1-yl-naphthalen-1-yl)-urea

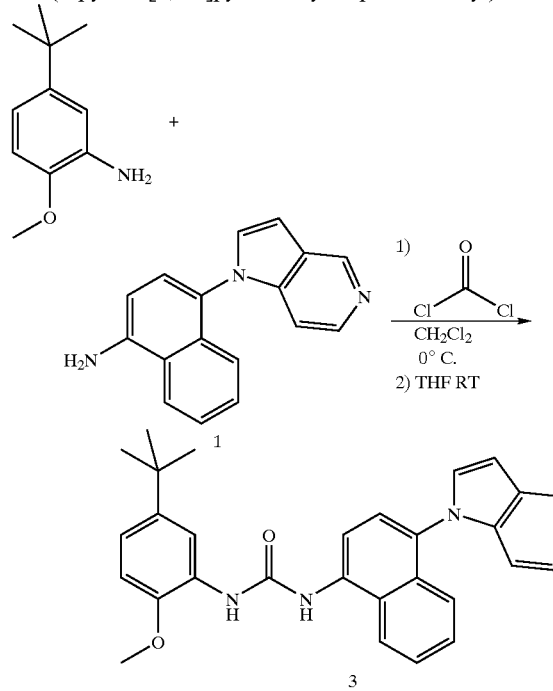

4-tert-Butyl-o-anisidine (54 mg, 0.301 mmol, 1 equiv.) was dissolved in 15 mL dichloromethane and 15 mL of saturated aqueous NaHCO₃ solution was added. The biphasic mixture was cooled to 0° C. and phosgene (~2 M solution in toluene, 0.75 mL) was added to the organic layer via syringe in one portion, without stirring. The mixture was then stirred vigorously for 10 min, then the layers were separated. The aqueous layer was extracted once with dichloromethane and the combined organics were dried (Na₂SO₄), filtered and most of the dichloromethane was removed in vacuo, leaving the toluene. To this isocyanate residue was then added 1-(4-aminonaphthalen-1-yl)pyrrolo[3,2-c]pyridine (Example 1) (77 mg, 0.297 mmol, 1 equiv.) dissolved in 5 mL anhydrous THF. The mixture was left to stir at room temperature for 2 h, then the solvents were removed in vacuo. The residue was purified by column chromatography on SiO₂ using dichloromethane/MeOH eluent mixtures. The isolated enriched fraction was further purified by reverse-phase preparative HPLC to provide 20 mg of the title compound as a white foam.

Example 4

Synthesis of N-{5-tert-butyl-2-methoxy-3-[3-(4-pyrrolo[3,2-c]pyridin-1-yl-naphthalen-1-yl)-ureido]-phenyl}-methanesulfonamide

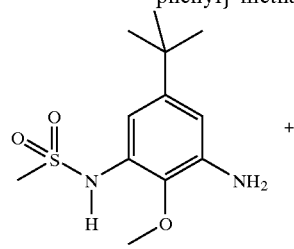

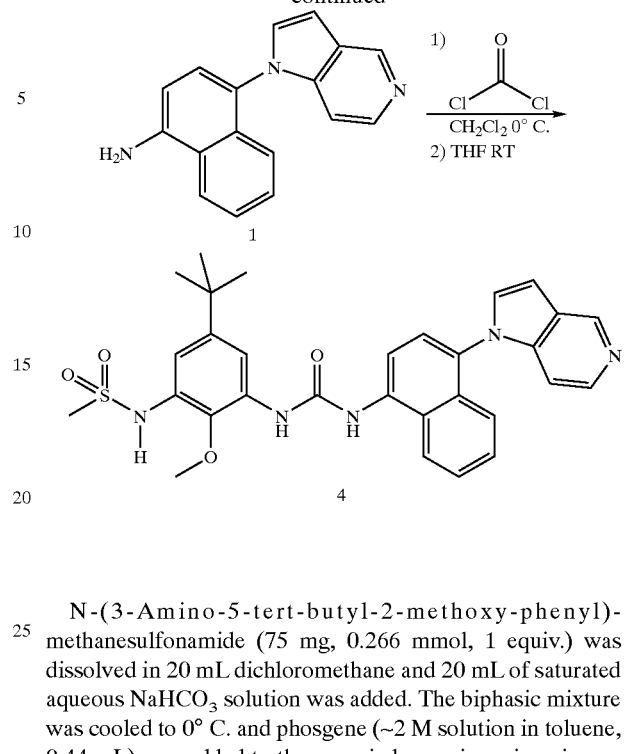

N-(3-Amino-5-tert-butyl-2-methoxy-phenyl)-methanesulfonamide (75 mg, 0.266 mmol, 1 equiv.) was dissolved in 20 mL dichloromethane and 20 mL of saturated aqueous NaHCO₃ solution was added. The biphasic mixture was cooled to 0° C. and phosgene (~2 M solution in toluene, 0.44 mL) was added to the organic layer via syringe in one portion without stirring. The mixture was then stirred vigorously for 10 min, then the layers were separated. The aqueous layer was extracted once with dichloromethane and the combined organics were dried (Na₂SO₄), filtered and most of the dichloromethane was removed in vacuo, leaving the toluene. To this isocyanate residue was then added 1-(4-aminonaphthalen-1-yl)pyrrolo[3,2-c]pyridine (Example 1) (46 mg, 0.177 mmol, 1 equiv.) dissolved in 5 mL anhydrous THF. The mixture was left to stir at room temperature overnight, then the solvents were removed in vacuo. The residue was purified by column chromatography on SiO₂ using dichloromethane/MeOH eluent mixtures. The title compound (34 mg) was isolated as a pink foam.

Example 5

Synthesis of 1-(4-aminonaphthalen-1-yl)-1H-imidazo[4,5-c]pyridine (5a) and 1-(4-aminonaphthalen-1-yl)-1H-imidazo[5,4-c]pyridine (5b)

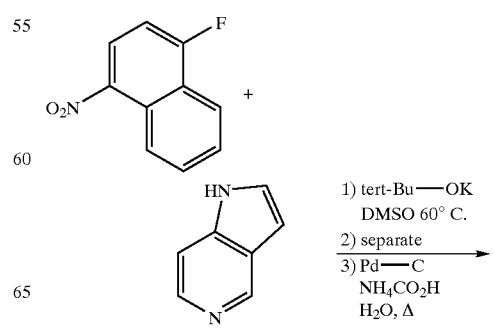

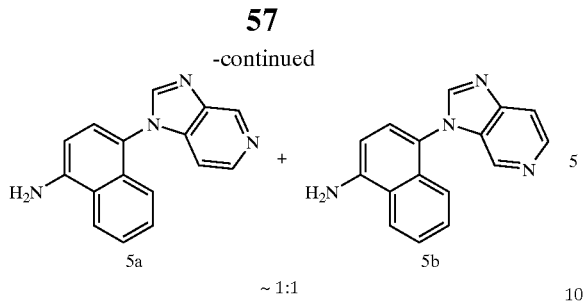

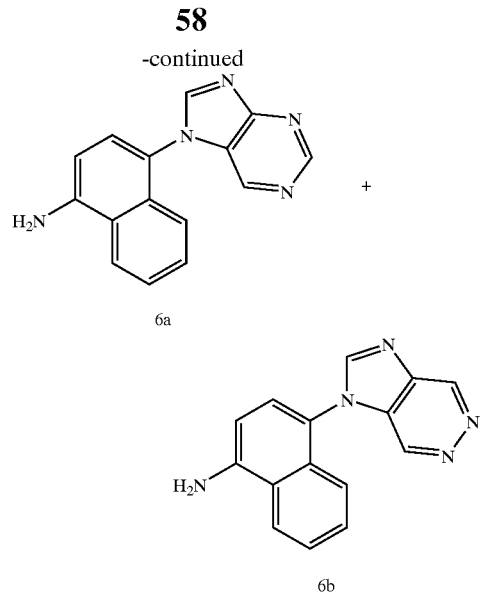

5-Aza-benzimidazole (312 mg, 2.62 mmol, 1 equiv.) in 5 mL anhydrous DMSO was treated with potassium tert-butoxide (294 mg, 2.62 mmol, 1.0 equiv.) at room temperature. When the mixture was completely homogeneous, 4-fluoro-1-nitro-naphthalene (500 mg, 2.62 mmol, 1 equiv.) was added in one portion and the mixture was heated to 60° C. for 0.5 h. The reaction was allowed to cool, then quenched with dilute aqueous NaHCO₃ solution. The product was extracted with a mixture of EtOAc, THF and acetone. The organic extracts were washed with water and brine, then dried (Na₂SO₄), filtered and the solvents removed in vacuo. ¹H NMR revealed a 1:1 ratio of regioisomers. The products were purified by column chromatography on SiO₂ using EtOAc/MeOH eluent mixtures. 1-(4-Nitro-naphthalen-1-yl)-1H-imidazo[5,4-c]pyridine was isolated at high Rf and 1-(4-nitro-naphthalen-1-yl)-1H-imidazo[4,5-c]pyridine at lower Rf, and overlapping fractions were in between. The overall yield was 357 mg (47%). Each nitro-naphthalene from above (~100 mg, 0.4 mmol) was separately dissolved in 10 mL EtOAc and 5 mL of MeOH. Ammonium formate was then added (100 mg, 1.6 mmol or 4 equiv.) and 10% palladium-on-carbon (~60 mg). The mixture was stirred for 0.5 h at 50° C., then allowed to cool, filtered through diatomaceous earth and the solvents were removed in vacuo to afford ~80 mg of each naphthylamine 5a and 5b, which could be coupled with anilines or pyrazolamines to form ureas by the procedures described in Examples 2–4 above.

Purine (137 mg, 1.14 mmol, 1 equiv.) in 2.0 mL anhydrous DMSO was treated with potassium tert-butoxide (128 mg, 1.14 mmol, 1 equiv.) at room temperature. When the solution was completely homogeneous, 4-fluoro-1-nitro-naphthalene (137 mg, 1.14 mmol, 1 equiv.) was added in one portion and the mixture was heated to 60° C. for 15 min. The reaction was allowed to cool, quenched with dilute aqueous NaHCO₃ solution (50 mL) and the product was collected by filtration to afford approximately a 4:1 ratio of regioisomers favoring 7-(4-nitro-naphthalen-1-yl)-7H-purine over 9-(4-nitro-naphthalen-1-yl)-9H-purine. These regioisomers were separated at this stage by column chromatography on SiO₂ using hexanes/EtOAc eluent mixtures, the major isomer eluting at lower Rf. Reductions to form 6a and 6b and couplings to form ureas were performed by procedures analogous to those described in Examples above.

Other substituted purines (for example 3-chloro-purine) can be reacted in an analogous fashion and functionalized further to introduce for example 3-thioalkyl, 3-alkoxy, 3-alkyl or aryl, 3-alkyl- or aryl-amino groups on the purine moiety.

Example 6

Synthesis of 7-(4-amino-naphthalen-1-yl)-7H-purine (6a) and 9-(4-amino-naphthalen-1-yl)-9H-purine (6b)

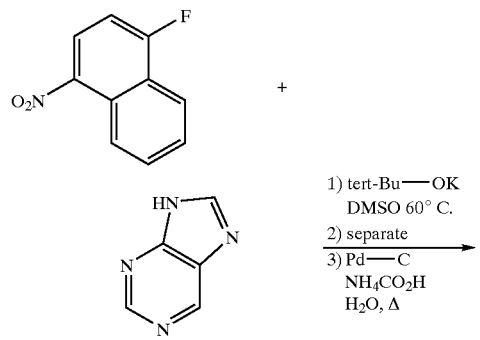

Example 7

Synthesis of 7-(4-amino-naphthalen-1-yl)-1H-pyrido[2,3-b][1,4]oxazin-2-one hydrochloride

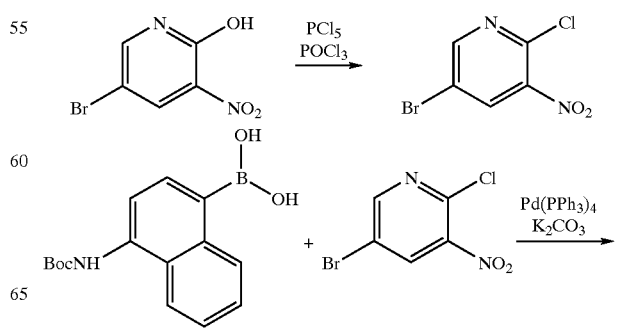

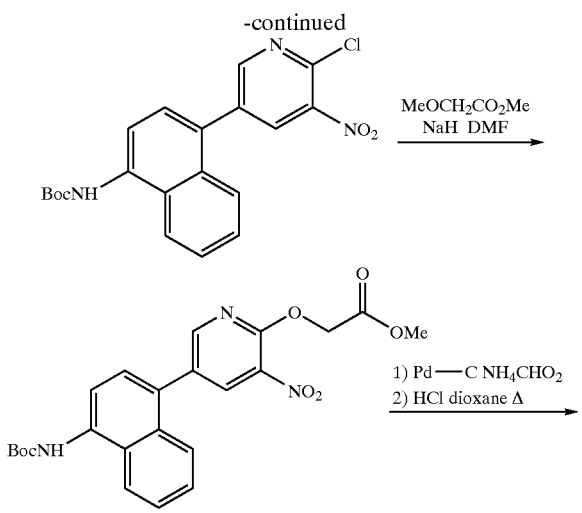

2-Hydroxy-3-nitro-5-bromopyridine (10 g) was combined with 25 mL of phosphorus oxychloride and 5 g of phosphorus pentachloride. The mixture was heated to 110° C. for 2 h, then cooled to room temperature and poured into ice-water and stirred 30 min. The mixture was extracted with CHCl₃, then the combined organics were dried (MgSO₄) and concentrated in vacuo. Purification by chromatography through a short plug of SiO₂, eluting with 4:1 hexanes:EtOAc afforded 6.72 g of 5-bromo-2-chloro-3-nitro-pyridine.

The 4-Boc-amino-naphth-1-yl boronic acid (0.271 g, 0.944 mmol) and the chloropyridine intermediate from above (0.213 g, 0.899 mmol) were combined in 3 mL of DME and 3 mL of 2M aqueous Na₂CO₃ solution was added. The biphasic mixture was purged with nitrogen for 10 min. Palladium tetrakis(triphenylphosphine) catalyst (0.104 g, 0.089 mmol) was then added and the mixture was heated at 65° C. for 4 h, then cooled to room temperature, diluted with EtOAc, washed with water and brine, and dried (MgSO₄). The coupled product was purified by flash chromatography on SiO₂ using 3:1 hexanes:EtOAc.

To sodium hydride (60% in oil, 104 mg, 2.61 mmol) suspended in 3 mL anhydrous DMF at 0–5° C., methl glycolate (0.19 mL, 2.51 mmol) was added dropwise. The mixture was stirred for 90 min, then a solution of the naphthyl-chloro-pyridine from above (0.334 g, 0.837 mmol) in 2 mL DMF was added. The mixture was stirred for 30 min, then quenched with 2 mL of AcOH and partitioned between water and Et₂O. The ether layer was washed with water, saturated aqueous NaHCO₃, brine, and dried (MgSO₄). The solvent was removed in vacuo, and the residue was purified by chromatography through a plug of SiO₂ with 2:1 hexanes:EtOAc eluent to provide 0.248 g (65%) of the desired ester.

A mixture of the above ester (0.234 g, 0.516 mmol), 10% palladium-on carbon (0.02 g) and ammonium formate (0.195 g, 3.10 mmol) in 8 mL EtOH was heated at 90° C. for 1 h, then cooled to room temperature. It was then diluted with EtOAc, filtered through diatomaceous earth, washed with water and brine, then dried (MgSO₄). After the solvent was removed in vacuo, the residue was taken up in 1,4-dioxane (5 mL) and treated with HCl in dioxane (4N, 3 mL). The mixture was heated at 70° C. for 3 h. MeOH (8 mL) was then added and the mixture was heated for another 45 min. Concentration in vacuo and trituration with Et₂O afforded the title compound (0.167 g, 99% yield).

Example 8

Synthesis of 1-(5-tert-butyl-2-methoxy-phenyl)-3-[4-(2-oxo-2,3-dihydro-1H-pyrido[2,3-b][1,4]oxazin-7-yl)-naphthalen-1-yl]-urea

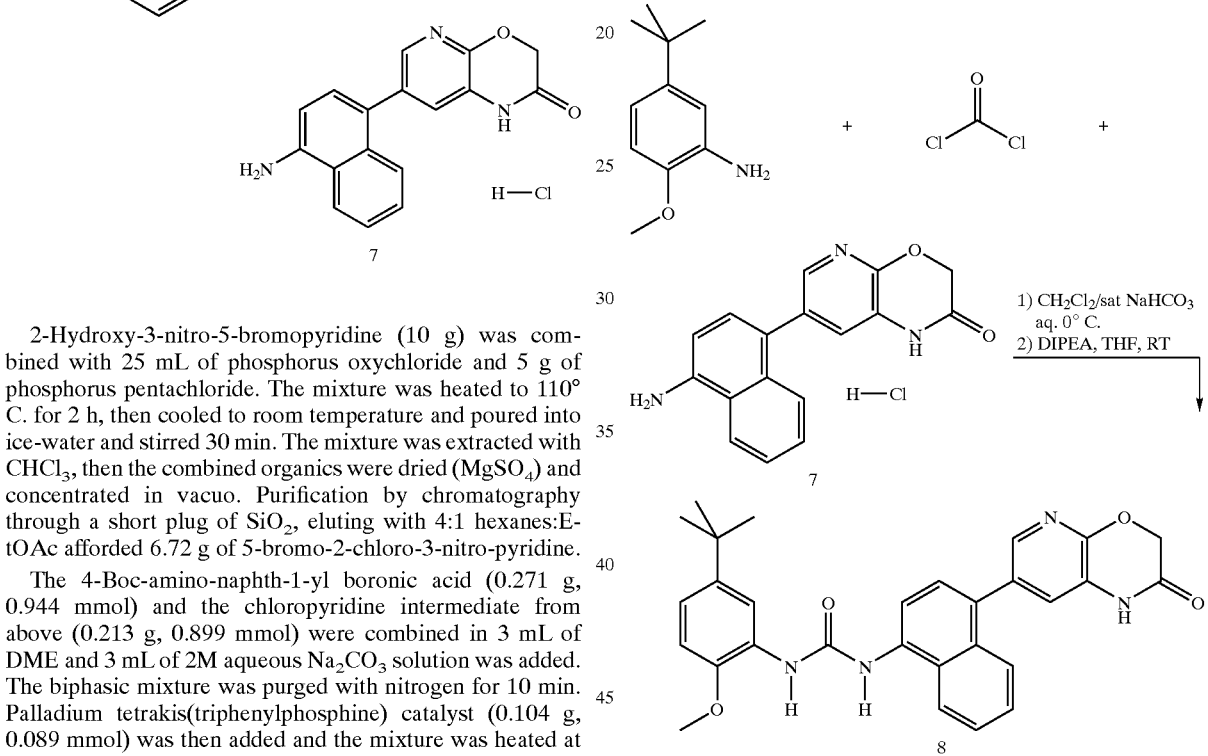

To 4-tert-butyl-o-anisidine (0.035 g, 0.198 mmol) in 2 mL dichloromethane and 2 mL saturated aqueous NaHCO₃ at 0° C., phosgene (~2 M in toluene, 0.21 mL, 0.40 mmol) was added via syringe to the organic layer in one portion, while not stirring. The resulting mixture was stirred vigorously for 10 min, then the organic layer was separated and dried (MgSO₄), filtered and concentrated in vacuo. To the resulting isocyanate solution was added a solution of 7-(4-amino-naphthalen-1-yl)-1H-pyrido[2,3-b][1,4]oxazin-2-one hydrochloride (Example 7) (72 mg, 0.220 mmol) and diisopropyl ethylamine (42 uL, 0.242 mmol) in 2 mL anhydrous THF. This mixture was stirred overnight, then diluted with EtOAc, washed with water and brine, dried (MgSO₄), filtered and the solvents removed in vacuo. The residue was purified by preparative HPLC to afford 12 mg of the title compound, m.p.>200° C.

Example 9

Synthesis of 1-(5-tert-butyl-2-p-tolyl-2H-pyrazol-3-yl)-3-[4-(2-oxo-2,3-dihydro-1H-pyrido[2,3-b][1,4]oxazin-7-yl)-naphthalen-1-yl)-urea

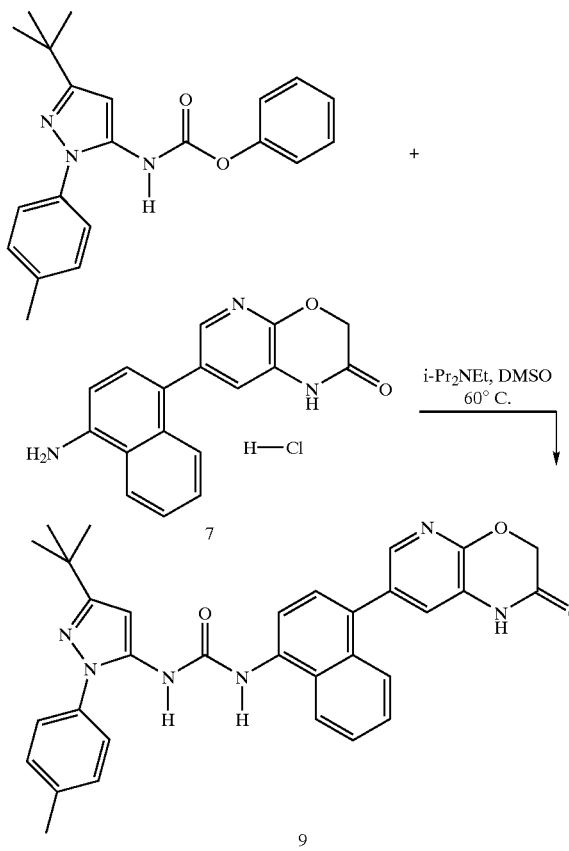

5-tert-Butyl-2-p-tolyl-2H-pyrazol-3-yl)-carbamic acid phenyl ester (0.035 g, 0.099 mmol), 7-(4-amino-naphthalen-1-yl)-1H-pyrido[2,3-b][1,4]oxazin-2-one hydrochloride (Example 7) (0.036 g, 0.11 mmol) and diisopropyl ethylamine (100 uL, 0.57 mmol) were combined in 1.5 mL anhydrous DMSO. The mixture was stirred at 60° C. under inert atmosphere for 5 h, then allowed to cool and quenched with water and extracted with EtOAc three times. The combined organic extracts were washed with brine, then dried (MgSO$_4$), filtered, and the solvents were removed in vacuo. The residue was purified by preparative HPLC providing 3 mg of the title compound, m.p.>200° C.

Example 10

Synthesis of 1-(5-tert-butyl-2-methoxy-phenyl)-3-[4-(2-oxo-1,2,3,4-tetrahydropyrido[2,3-b]pyrazin-7-yl)-naphthalen-1-yl]-urea

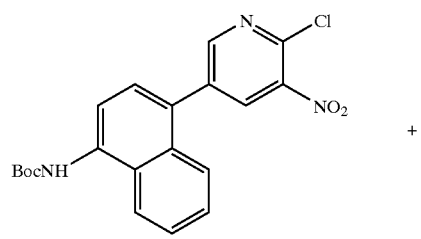

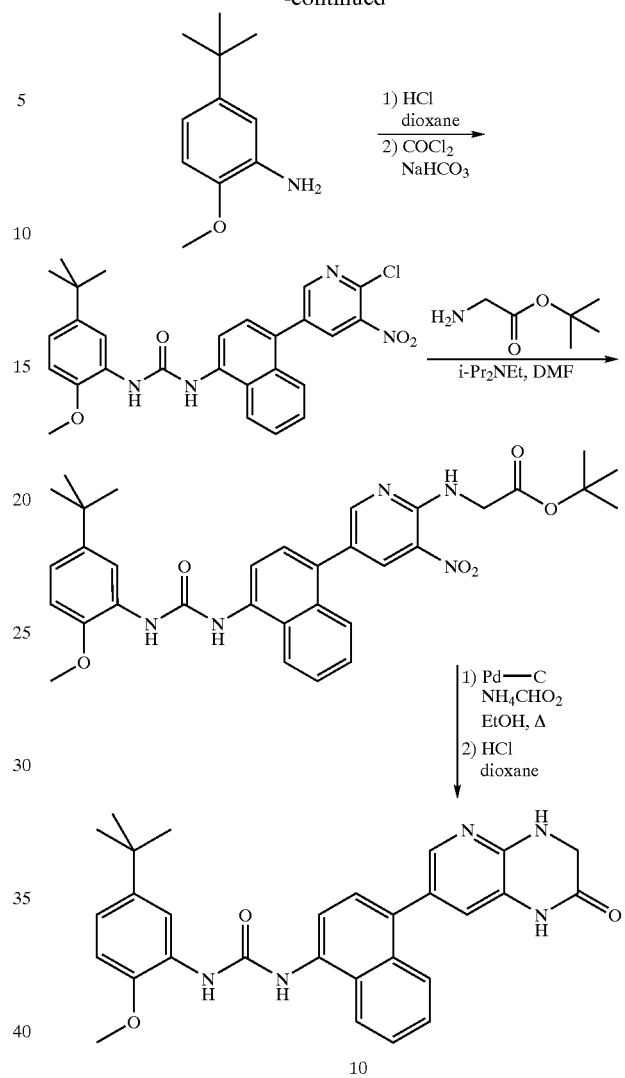

A mixture of 4-(2-chloro-3-nitropyridin-3-yl)-N-Boc-naphth-1-yl amine (0.62 g) and 4 mL of 4 N HCl in 1,4-dioxane in 10 mL dioxane was stirred at room temperature overnight. The reaction was diluted with ether and the resulting precipitate filtered and dried in vacuo. To this naphthylamine hydrochloride (0.201 g, 0.542 mmol) in 5 mL dichloromethane and 5 mL saturated aqueous NaHCO$_3$ solution at 0° C., phosgene (~2M in toluene, 0.71 mL, 1.35 mmol) was added via syringe to the organic layer in one portion, while not stirring. The resulting mixture was stirred vigorously for 15 min, then the organic layer was separated, dried (MgSO$_4$), filtered and concentrated in vacuo. To the resulting isocyanate solution was added a solution of the tert-butyl-o-anisidine (0.097 g, 0.542 mmol). This mixture was stirred 4 h at room temperature, then concentrated in vacuo and purified by flash chromatography using 35% EtOAc in hexanes as eluent to afford the desired urea.

Glycine tert-butyl ester hydrochloride (0.044 g, 0.263 mmol) and diisopropyl ethylamine (0.14 mL, 0.788 mmol) were mixed in 2 mL anhydrous DMF. To this mixture was added the urea from above (0.106 g, 0.210 mmol). The reaction was stirred at room temperature overnight, diluted with water and the resulting solid was filtered and dried in vacuo.

To the solid from above (0.108 g) and ammonium formate (68 mg) in 2 mL EtOH was added 10% palladium-on-carbon (15 mg). The mixture was heated at 60° C. for 15 min, cooled to room temperature, diluted with EtOAc and filtered. The organics were washed with water, then brine, then dried (MgSO₄). The residue was diluted with 3 mL EtOH and 2 mL 4 N HCl in 1,4-dioxane and heated at 75° C. for 90 min. The reaction was cooled to room temperature and concentrated in vacuo. The residue was diluted with EtOAc, washed with saturated aqueous NaHCO₃, brine, and dried (MgSO₄). The residue was diluted with acetonitrile and filtered to afford the title compound (28 mg), m.p.>230° C.

Example 11

Synthesis of 1-(5-tert-butyl-2-methoxy-phenyl)-3-[4-(4,4-dioxo-3,4-dihydro-2-oxo-1H-4λ⁶-pyrido[2,3-b][1,4]thiazin-7-yl)-naphthalen-1-yl]-urea

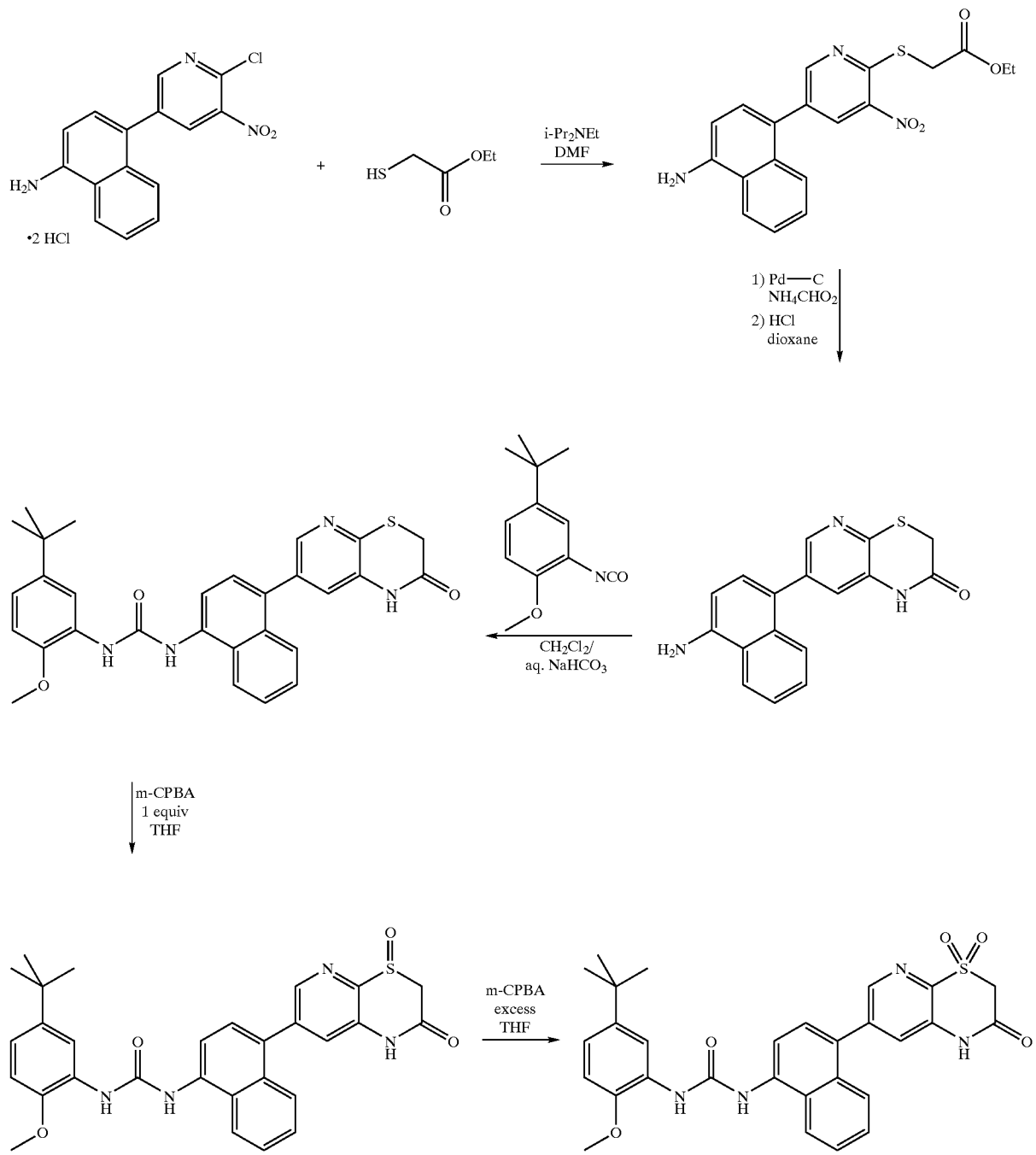

4-(2-chloro-3-nitropyridin-3-yl)-naphth-1-yl amine dihydrochloride (0.238 g, 0.642 mmol), ethyl thioglycolate (70 uL, 0.642 mmol) and diisopropyl ethylamine (0.45 mL, 2.57 mmol) were combined in 4 mL DMF and stirred at room temperature overnight. The reaction mixture was then diluted with water and the product extracted with $Et_2O$. The organic layer was washed with water and brine, then dried ($MgSO_4$) providing 0.23 g of the desired thioether.

The thioether from above (0.23 g, 0.601 mmol), ammonium formate (0.15 g, 2.40 mmol) and 10% palladium-on-carbon (200 mg) were combined in 5 mL EtOH and 1 mL EtOAc. The mixture was heated at 90° C. for 24 h, cooled to room temperature and filtered through diatomaceous earth. The filtrate was diluted with EtOAc, washed with water and brine, dried ($MgSO_4$), filtered, and the solvents were removed in vacuo, providing the desired pyrido-thioxazin-2-one (161 mg).

To 4-tert-butyl-o-anisidine (84.5 mg, 0.472 mmol) in 3 mL dichloromethane and 3 mL saturated aqueous $NaHCO_3$ at 0–5° C., phosgene (~2 M in toluene, 0.62 mL, 1.18 mmol) was added in one portion, to the organic layer, via syringe, while not stirring. The mixture was stirred vigorously for 15 min, then the organic layer was separated, dried ($MgSO_4$) and concentrated in vacuo. The residue was then diluted with 2 mL anhydrous THF, cooled to 0° C., and treated with the pyrido-thioxazin-2-one from above (0.145 g, 0.472 mmol) dissolved in 1 mL anhydrous THF. The mixture was allowed to reach room temperature and stir overnight. The solvent was then removed in vacuo, and the product was purified by flash chromatography on $SiO_2$ using 1:1 hexanes:EtOAc as eluent, providing 0.137 g of the desired urea which was further purified by reverse-phase preparative HPLC, providing the sulfoxide, m.p. 188–190° C.

The sulfoxide from above (0.044 g, 0.0859 mmol), dissolved in 2 mL THF, was treated with m-CPBA (60–65%, 0.022 g, 0.0859 mmol) and the mixture was stirred at room temperature overnight. It was then diluted with EtOAc, washed with aqueous $Na_2S_2O_5$, with saturated $NaHCO_3$, then with brine, then dried ($MgSO_4$) and concentrated in vacuo. The residue was purified by reverse-phase preparative HPLC providing the sulfoxide, m.p.>240° C.

The sulfoxide from above (0.052 g, 0.101 mmol) was dissolved in 2 mL THF and treated with m-CPBA (60–65%, 0.037 g, 0.213 mmol) at room temperature. The mixture was stirred for 2 days, then treated with another 30 mg of m-CPBA and stirred one day. The mixture was then diluted with EtOAc, washed with aqueous $Na_2S_2O_5$, with saturated $NaHCO_3$, then with brine, then dried ($MgSO_4$) and concentrated. The residue was purified by reverse-phase preparative HPLC providing the title compound, m.p.>209–211° C.

Example 12

Synthesis of N-(3-{3-[4-(3-Benzyl-2-oxo-2,3-dihydro-1H-pyrido[2,3-b][1,4]oxazin-7-yl)-naphthalen-1-yl]-ureido}-5-tert-butyl-2-methoxy-phenyl)-methanesulfonamide

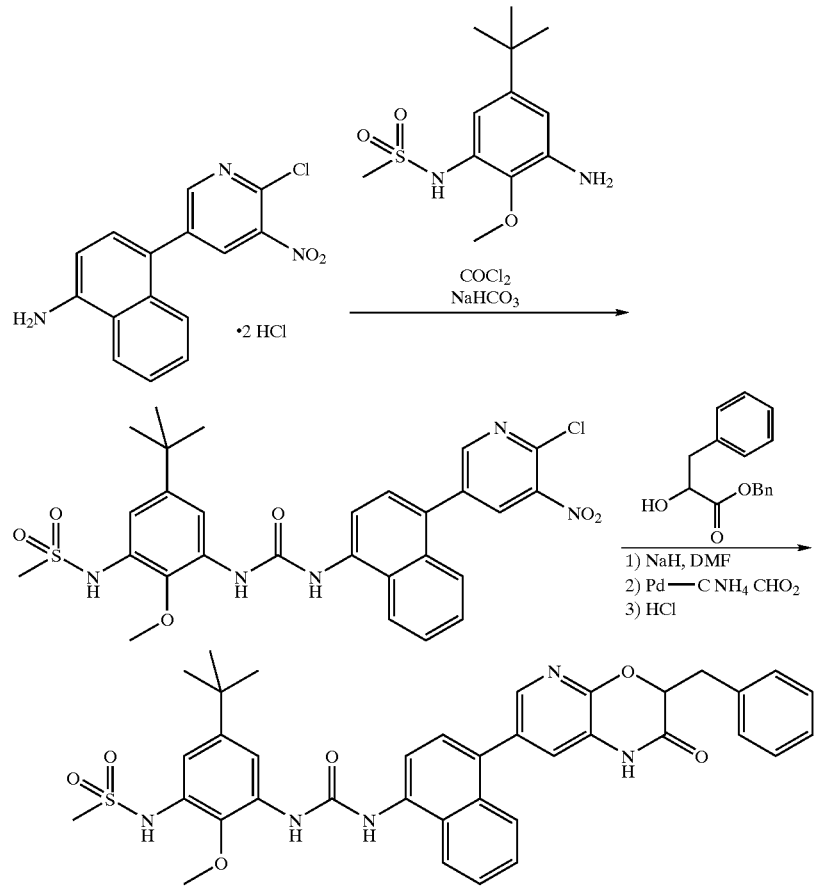

To 4-(2-chloro-3-nitropyridin-3-yl)-naphth-1-yl amine dihydrochloride (0.203 g, 0.544 mmol) in 5 mL dichloromethane and 5 mL saturated aqueous NaHCO$_3$ at 0–5° C., phosgene (2 M in toluene, 0.72 mL, 1.37 mmol) was added in one portion to the organic layer, via syringe, while not stirring. The mixture was stirred vigorously for 15 min, then the organic layer was separated and dried (MgSO$_4$) and concentrated in vacuo. The residue was then diluted with 2 mL anhydrous THF and treated with N-(3-amino-5-tert-butyl-2-methoxy-phenyl)-methanesulfonamide (0.148 g, 0.544 mmol) dissolved in 5 mL anhydrous THF. The mixture was allowed to reach room temperature and stir overnight. The solvent was then removed in vacuo, and the product was purified by flash chromatography on SiO$_2$ using 1:1 hexanes:EtOAc as eluent, providing 0.050 g of the desired urea product.

Racemic benzyl-2-hydroxy-3-phenyl-propionate (0.094 mL, 0.418 mmol) was added to NaH (60% in oil, 18 mg) in 2 mL anhydrous DMF at 0–5° C. After stirring for 1 h, the above urea was added (0.050 g, 0.0837 mmol). The mixture was stirred for 2.5 h at 0–5° C., then at room temperature for 1 h, then diluted with AcOH and ether. The organic layer was washed with water, aqueous NaHCO$_3$ and brine, dried (MgSO$_4$), filtered, and concentrated. The residue was purified by flash chromatography on SiO$_2$ using 1:1 hexanes:EtOAc as eluent providing 53 mg of desired the desired pyridyl-ether. This material was dissolved in 2 mL EtOH and 1 mL EtOAc, treated with ammonium formate (85 mg) and catalytic palladium-on-carbon (10%, 15 mg). The mixture was heated at 65° C. for 20 min, cooled to room temperature, filtered over diatomaceous earth, washed with water, brine and dried (MgSO$_4$). The solvent was removed in vacuo, then the residue was dissolved in 2 mL EtOH and 1 mL of 4 N HCl in 1,4-dioxane. The mixture was heated at 75° C. for 25 min, then concentrated in vacuo. The residue was taken up in EtOAc, and washed with saturated NaHCO$_3$, and brine, and dried (MgSO$_4$) and concentrated. The residue was purified by reverse-phase preparative HPLC providing 2 mg of the title compound.

Assessment of Biological Properties
Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP.1 cells (2×10$^6$ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min, 37° C., 5% CO$_2$ prior to stimulation with lipopolysaccharide (LPS; 1 μg/ml final; Siga L-2630, from *E.coli* serotype 0111.B4; stored as 1 mg/ml stock in endotoxin screened distilled H$_2$O at −80° C.). Blanks (unstimulated) received H$_2$O vehicle; final incubation volume was 250 μl. Overnight incubation (18–24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated IC50 value is the concentration of the test compound that caused a 50% decrease in the maximal TNFα production.

Preferred compounds including those from the synthetic examples above were evaluated and had IC$_{50}$<10 μM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1β, GM-CSF, IL-6 and IL-8 can be demonstrated (for example, see J. C. Lee et al., 1988, *Int. J. Immunopharmacol.*, 10, 835).

We claim:
1. A compound of the formula (I):

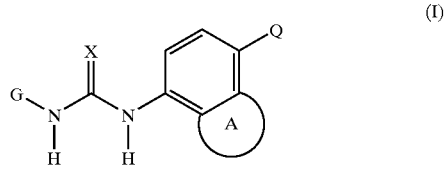

wherein:
ring A is:
fused saturated or unsaturated ring containing 3–5 carbon atoms wherein ring A or the phenyl ring to which it is fused is optionally substituted by one or more C$_{1-6}$ branched or unbranched alkyl, acetyl, benzoyl, naphthoyl, C$_{1-6}$ branched or unbranched alkoxy, halogen, methoxycarbonyl, phenylsulfonyl, hydroxy, amino, mono- or di-(C$_{1-4}$ alkyl)amino, mono- or di-(C$_{1-4}$ alkyl)amino-S(O)$_m$, cyano, nitro or H$_2$NSO$_2$;

G is a 5-membered heteroaryl ring;
wherein G is optionally substituted by one or more R$_1$, R$_2$ or R$_3$;

Q is
a carbocyclic ring chosen from naphthyl, benzocyclobutanyl, dihydronaphthyl, tetrahydronaphthyl, benzocycloheptanyl, benzocycloheptenyl, indanyl and indenyl;
a ring system chosen from benzoxazinyl, benzimidazolyl, benzothiazolyl, benzooxazolyl, benzofuranyl, benzopyranyl, benzodioxolyl, quinaldinyl, quinazolinyl, quinoxalinyl, isoquinolinyl, quinolinyl, indolyl, isoindolyl, indolinyl, purinyl, tetrahydroquinolinyl, indazolyl, imidazo-pyridinyl, pyrazolo-pyridinyl, pyrazolo-pyrimidinyl, pyrrolo-pyrimidinyl, pyrrolo-pyridinyl, pyrido-pyrazinyl, pyrido-pyrimidinyl, pyrido-oxazinyl, pyrido-thiazinyl, pyrido-oxazolyl, pyrido-thioxazolyl, pyrimido-pyrimidine, pteridinyl, cinnolinyl and naphthyridinyl;

wherein each Q is optionally substituted with one to three Y,
each Y is independently chosen from
L-NR$_5$R$_6$ wherein L is a bond, —(CH$_2$)$_{1-5}$— or >C(O),
hydrogen, oxo, C$_{1-5}$ alkyl branched or unbranched, C$_{1-3}$ alkyl(OH), C$_{2-5}$ alkenyl, C$_{1-3}$ acyl, heterocyclylC$_{0-3}$ alkyl wherein the heterocyclyl is chosen from morpholinyl, piperazinyl, piperidinyl, pyrrolidinyl, tetrahydropyranyl and tetrahydrofuryl, heteroaryl$C_{0-3}$ alkyl wherein the heteroaryl is chosen from pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl and indazolyl and phenyl$C_{0-3}$ alkyl or naphthyl$C_{0-3}$ alkyl, wherein each Y is optionally substituted by one to three hydroxy, oxo, $C_{1-4}$ alkyl, $C_{1-3}$ alkoxy, $C_{1-4}$ acyl, $C_{1-5}$ alkoxycarbonyl, —$NR_5R_6$ or $NR_5R_6$—C(O)—;

each $R_5$ or $R_6$ is independently:

hydrogen, phenyl$C_{0-3}$ alkyl, naphthyl$C_{0-3}$ alkyl, $C_{3-7}$ cycloalkyl$C_{0-3}$ alkyl, heterocyclyl$C_{0-3}$ alkyl or heterocyclylcarbonyl wherein the heterocyclyl is as hereinabove described for Y, heteroaryl$C_{0-3}$ alkyl or heteroarylcarbonyl wherein the heteroaryl is as hereinabove described for Y, $C_{1-3}$ acyl, benzoyl, naphthoyl or $C_{1-6}$ branched or unbranched alkyl, each $R_5$ or $R_6$ is optionally substituted by $C_{1-5}$ alkoxy, hydroxy, mono- or di-$C_{1-3}$alkylaminocarbonyl, mono or di$C_{1-3}$ alkyl amino, mono or di$C_{1-3}$ alkylsulfonylamino or $C_{1-3}$ alkylsulfonyl;

each $R_1$ is independently:

$C_{1-10}$ alkyl branched or unbranched, wherein one or more C atoms are optionally independently replaced by O, N or S(O)$_m$, and wherein said $C_{1-10}$ alkyl is optionally substituted with one to three $C_{3-10}$ cycloalkyl, hydroxy, oxo, phenyl, naphthyl or halogen;

or $R_1$ is cyclopropyloxy, cyclobutyloxy, cyclopentyloxy, cyclohexyloxy or cycloheptyloxy each optionally substituted with one to three $C_{1-3}$ alkyl groups, nitrile, hydroxy$C_{1-3}$alkyl, phenyl or naphthyl;

phenyloxy or benzyloxy each optionally substituted with one to three $C_{1-3}$ alkyl groups, nitrile, hydroxy$C_{1-3}$alkyl, phenyl or naphthyl;

cyclopropyl, cyclobutyl, cyclopentyl, cyclohexyl, cycloheptyl, bicyclopentanyl, bicyclohexanyl or bicycloheptanyl, each being optionally substituted with one to three $C_{1-3}$ alkyl, nitrile, hydroxy$C_{1-3}$alkyl, phenyl or naphthyl;

$C_{3-10}$ branched or unbranced alkenyl each being optionally substituted with one to three $C_{1-5}$ branched or unbranched alkyl, phenyl or naphthyl;

cyclopentenyl, cyclohexenyl, cyclohexadienyl, cycloheptenyl, cycloheptadienyl, bicyclohexenyl or bicycloheptenyl, wherein each optionally substituted with one to three $C_{1-3}$ alkyl groups;

oxo, nitrile, halogen; or $C_{3-6}$ alkynyl branched or unbranched carbon chain wherein one or more methylene groups are optionally replaced by O, N or S(O)$_m$ and wherein said alkynyl group is optionally independently substituted with one to two oxo groups, hydroxy, pyrrolidinyl, pyrrolyl, tetrahydropyranyl, $C_{1-4}$ alkyl optionally substituted by one or more halogen atoms, nitrile, morpholino, piperidinyl, piperazinyl, imidazolyl, phenyl, pyridinyl, tetrazolyl or mono- or di($C_{1-3}$alkyl)amino;

each $R_2$ is independently:

a $C_{1-6}$ branched or unbranched alkyl optionally halogenated, $C_{1-6}$acyl, benzoyl, naphthoyl, $C_{1-4}$ branched or unbranched alkoxy optionally halogenated, halogen, methoxycarbonyl, $C_{1-4}$ alkyl-S(O)$_m$ branched or unbranched or phenyl-S(O)$_m$;

each $R_3$ is independently $C_{1-6}$ branched or unbranched alkyl, phenyl$C_{0-6}$ alkyl, naphthyl$C_{0-6}$ alkyl, heteroaryl$C_{0-6}$ alkyl or heterocyclyl $C_{0-6}$ alkyl each optionally substituted with one to three $C_{1-3}$ alkyl groups, nitrile, hydroxy$C_{1-3}$alkyl or aryl;

each m is independently 0, 1 or 2;

and X is O or S;

or the pharmaceutically acceptable salts thereof;

with the proviso that the following compounds are excluded:

1-[5-tert-butyl-2-p-tolyl-2H-pyrazol-3-yl]-3-[4-(1-morpholin-4-yl-indan-5-yl)-naphthalen-1-yl]-urea and 1-[5-tert-butyl-2-p-tolyl-2H-pyrazol-3-yl]-3-[4-(3-benzyl-3H-imidazo[4,5-b]pyridin-6-yl)naphthalen-1-yl]-urea.

2. The compound according to claim 1 wherein:

ring A and the phenyl ring to which it is fused form:

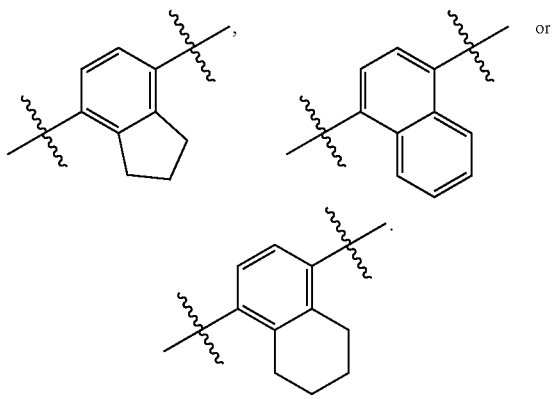

3. The compound according to claim 2 wherein:

G is pyrrolyl, imidazolyl, pyrazolyl, thienyl, furyl, thiazolyl or oxazolyl;

wherein G is optionally substituted by one to three $R_1$, $R_2$ or $R_3$;

ring A and the phenyl ring to which it is fused form:

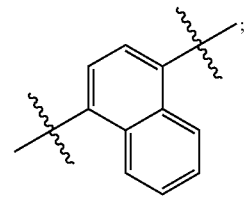

Q is a ring system chosen from benzimidazolyl, benzothiazolyl, benzooxazolyl, benzisoxazolyl, benzofuranyl, benzodioxolyl, indolyl, isoindolyl, imidazo[4,5-b]pyridinyl, imidazo[4,5-c]pyridinyl, purinyl, indazolyl, quinolinyl, isoquinolinyl, quinazolinyl, benzopyranyl, benzoxazinyl, pyrido[2,3-b]oxazinyl, pyrido[2,3-b]pyrazinyl, pyrido[2,3-b]thiazinyl, pyrrolo[3,2-c]pyridinyl and pyrazolo[3,4-d]pyrimidinyl; wherein each Q is optionally substituted with one to three Y, $R_1$ is $C_{1-10}$ alkyl, $C_{1-10}$ alkoxy each branched or unbranched and optionally substituted with one to three $C_{3-10}$ cycloalkyl, hydroxy, oxo, phenyl, naphthyl or halogen, or $R_1$ is cyclopropyl, cyclobutyl, cyclopentyl, cyclohexyl, cycloheptyl, bicyclopentanyl, bicyclohexanyl or bicycloheptanyl, each optionally substituted with one to three $C_{1-3}$ alkyl, nitrile, hydroxy$C_{1-3}$alkyl phenyl or naphthyl;

$R_3$ is $C_{1-6}$ branched or unbranched alkyl, phenyl, naphthyl, benzyl, phenethyl, heteroaryl$C_{0-6}$ alkyl wherein the heteroaryl is chosen from pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl and indazolyl or heterocyclyl$C_{0-6}$ alkyl wherein the heterocyclyl is chosen from morpholinyl, piperazinyl, piperidinyl, pyrrolidinyl and tetrahydrofuryl, each optionally substituted with one to three $C_{1-3}$ alkyl; and X is O.

4. The compound according to claim 3 wherein:

G is pyrrolyl, imidazolyl or pyrazolyl, wherein G is optionally substituted by one to three $R_1$, $R_2$ or $R_3$;

each Y is independently chosen from

L-NR$_5$R$_6$ wherein L is a bond, —(CH$_2$)$_{1-5}$— or >C(O), hydrogen, oxo, $C_{1-5}$ alkyl branched or unbranched, $C_{1-3}$ alkyl(OH), $C_{2-5}$ alkenyl, $C_{1-3}$ acyl, heterocyclyl$C_{0-3}$ alkyl wherein the heterocyclyl is chosen from morpholinyl, piperazinyl, and pyrrolidinyl, heteroaryl$C_{0-3}$ alkyl wherein the heteroaryl is chosen from pyridinyl, pyrimidinyl, pyrazinyl, pyridazinyl, pyrrolyl, imidazolyl, pyrazolyl, isoxazolyl, thiazolyl, and oxazolyl, phenyl, naphthyl, benzyl and phenethyl, wherein each Y is optionally substituted by one to three hydroxy, oxo, $C_{1-4}$ alkyl, $C_{1-3}$ alkoxy, $C_{1-4}$ acyl, $C_{1-5}$ alkoxycarbonyl or —NR$_5$R$_6$;

each $R_5$ or $R_6$ is independently:

hydrogen, phenyl, naphthyl, benzyl, phenethyl, $C_{3-7}$ cycloalkyl$C_{0-3}$ alkyl, heterocyclyl$C_{0-3}$ alkyl or heterocyclylcarbonyl wherein the heterocyclyl is chosen from morpholinyl, tetrahydrofuranyl, tetrahydropyranyl, heteroaryl$C_{0-3}$ alkyl or heteroarylcarbonyl wherein the heteroaryl is chosen from pyridinyl, pyrimidinyl, pyrazinyl and pyridazinyl, $C_{1-3}$ acyl, benzoyl, naphthoyl or $C_{1-6}$ branched or unbranched alkyl, each $R_5$ or $R_6$ is optionally substituted by $C_{1-5}$ alkoxy, mono or di$C_{1-3}$ alkyl amino, mono or di$C_{1-3}$ alkylsulfonylamino or $C_{1-3}$ alkylsulfonyl;

$R_1$ is $C_{1-10}$ alkyl, $C_{1-9}$ alkoxy each branched or unbranched and optionally substituted with one to three $C_{3-10}$ cycloalkyl, hydroxy, oxo, phenyl, naphthyl, fluoro, bromo or chloro; and $R_3$ is $C_{1-6}$ branched or unbranched alkyl, phenyl, naphthyl, benzyl, phenethyl, pyridinyl, morpholinyl, piperazinyl, piperidinyl or pyrrolidinyl each optionally substituted with one to three $C_{1-3}$ alkyl.

5. The compound according to claim 4 wherein:

G is pyrazolyl optionally substituted by one to three $R_1$, $R_2$ or $R_3$;

Q is chosen from imidazo[4,5-b]pyridinyl, imidazo[4,5-c]pyridinyl, pyrido[2,3-b]oxazinyl and pyrrolo[3,2-c]pyridinyl;

wherein each Q is optionally substituted with one to three Y;

each Y is independently chosen from

L-NR$_5$R$_6$ wherein L is a bond, —(CH$_2$)$_{1-5}$— or >C(O), hydrogen, oxo, $C_{1-5}$ alkyl branched or unbranched, heterocyclyl$C_{0-3}$ alkyl wherein the heterocyclyl is chosen from morpholinyl, piperazinyl, and pyrrolidinyl, pyridinyl$C_{0-3}$ alkyl or benzyl, wherein each Y is optionally substituted by one to three hydroxy, oxo, $C_{1-4}$ alkyl, $C_{1-3}$ alkoxy, $C_{1-4}$ acyl or —NR$_5$R$_6$; and each $R_5$ or $R_6$ is independently:

hydrogen, phenyl, benzyl, $C_{3-6}$ cycloalkyl$C_{0-3}$ alkyl, heterocyclyl$C_{0-3}$ alkyl or heterocylylcarbonyl wherein the heterocyclyl is chosen from morpholinyl, tetrahydrofuranyl, tetrahydropyranyl, pyridinyl$C_{0-3}$ alkyl, pyridinylcarbonyl, $C_{1-3}$ acyl, benzoyl or $C_{1-6}$ branched or unbranched alkyl, each $R_5$ or $R_6$ is optionally substituted by $C_{1-5}$ alkoxy, mono or di$C_{1-3}$ alkyl amino, mono or di$C_{1-3}$ alkylsulfonylamino or $C_{1-3}$ alkylsulfonyl.

6. The compound according to claim 5 wherein:

G is 2H-pyrazol-3-yl optionally substituted by one to three $R_1$, $R_2$ or $R_3$;

Q is chosen from:

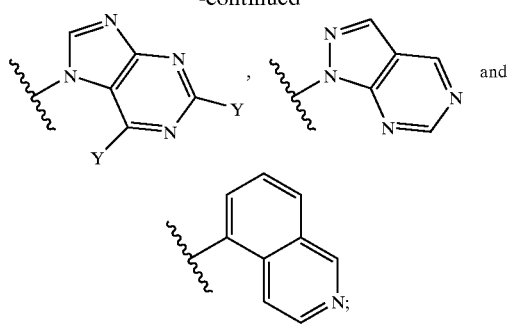

R₁ is

CF₃, OCF₃, —C(CH₃)₃, —C(CH₂F)₃ or —CH₂C(CH₃)₃; and

R₃ is phenyl or benzyl each optionally substituted with one to three $C_{1-3}$ alkyl.

7. The compound according to claim 6 wherein:

G is:

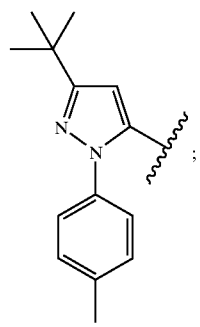

Q is chosen from

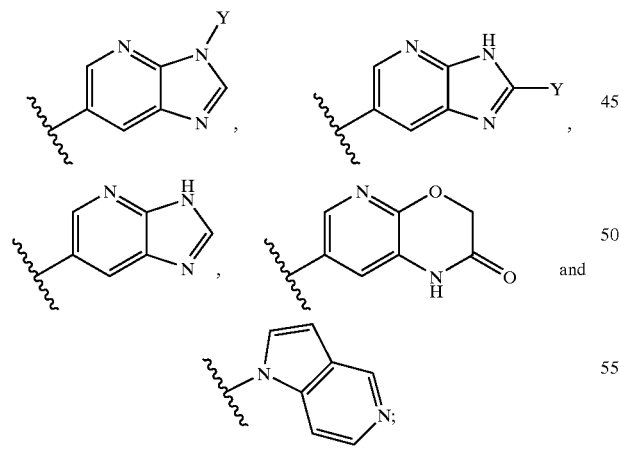

Y is independently chosen from

L-NR₅R₆ wherein L is a bond or —(CH₂)₁₋₃—, $C_{1-5}$ alkyl branched or unbranched, morpholinylC₀₋₃ alkyl or benzyl; and each R₅ or R₆ is independently:

hydrogen, phenyl, benzyl or $C_{3-6}$ cycloalkylC₀₋₃ alkyl.

8. A compound of the formula (II):

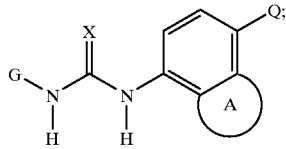

(II)

wherein:

ring A is:

fused saturated or unsaturated ring containing 3–5 carbon atoms wherein ring A or the phenyl ring to which it is fused is optionally substituted by one or more a $C_{1-6}$ branched or unbranched alkyl, acetyl, benzoyl, naphthoyl, $C_{1-6}$ branched or unbranched alkoxy, halogen, methoxycarbonyl, phenylsulfonyl, hydroxy, amino, mono- or di-($C_{1-4}$ alkyl)amino, mono- or di-($C_{1-4}$ alkyl)amino-S(O)$_m$, cyano, nitro or H₂NSO₂;

G is a 6-membered monocyclic heteroaryl ring chosen from pyridinyl, pyrimidinyl, pyrazinyl, and pyridazinyl;

a ring system chosen from benzoxazinyl, benzimidazolyl, benzothiazolyl, benzooxazolyl, benzofuranyl, benzopyranyl, benzodioxolyl, quinaldinyl, quinazolinyl, quinoxalinyl, isoquinolinyl, quinolinyl, indolyl, isoindolyl, indolinyl, purinyl, indazolyl, imidazo-pyridinyl, pyrazolo-pyridinyl, pyrazolo-pyrimidinyl, pyrrolo-pyrimidinyl, pyrrolo-pyridinyl, pyrido-pyrazinyl, pyrido-pyrimidinyl, pyrido-oxazinyl, pyrido-thiazinyl, pyrido-oxazolyl, pyrido-thioxazolyl, pyrimido-pyrimidine, pteridinyl, cinnolinyl and naphthyridinyl;

a 3–7 membered carbocyclic ring aromatic or nonaromatic;

wherein G is optionally substituted by one or more R₁, R₂ or R₃;

Q is a carbocyclic ring chosen from naphthyl, benzocyclobutanyl, dihydronaphthyl, tetrahydronaphthyl, benzocycloheptanyl, benzocycloheptenyl, indanyl and indenyl;

a ring system chosen from benzoxazinyl, benzimidazolyl, benzothiazolyl, benzooxazolyl, benzofuranyl, benzopyranyl, benzodioxolyl, quinaldinyl, quinazolinyl, quinoxalinyl, isoquinolinyl, quinolinyl, indolyl, isoindolyl, indolinyl, purinyl, tetrahydroquinolinyl, indazolyl, imidazo-pyridinyl, pyrazolo-pyridinyl, pyrazolo-pyrimidinyl, pyrrolo-pyrimidinyl, pyrrolo-pyridinyl, pyrido-pyrazinyl, pyrido-pyrimidinyl, pyrido-oxazinyl, pyrido-thiazinyl, pyrido-oxazolyl, pyrido-thioxazolyl, pyrimido-pyrimidine, pteridinyl, cinnolinyl and naphthyridinyl;

wherein each Q is optionally substituted with one to three Y, each Y is independently chosen from L-NR₅R₆ wherein L is a bond, —(CH₂)₁₋₅— or >C(O), hydrogen, oxo, $C_{1-5}$ alkyl branched or unbranched, $C_{1-3}$ alkyl(OH), $C_{2-5}$ alkenyl, $C_{1-3}$ acyl, heterocyclylC₀₋₃ alkyl wherein the heterocyclyl is chosen from morpholinyl, piperazinyl, piperidinyl, pyrrolidinyl and tetrahydrofuryl, heteroarylC₀₋₃ alkyl wherein the heteroaryl is chosen from pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl and indazolyl phenylC$_{0-3}$ alkyl and naphthylC$_{0-3}$ alkyl, wherein each Y is optionally substituted by one to three hydroxy, oxo, C$_{1-4}$ alkyl, C$_{1-3}$ alkoxy, C$_{1-4}$ acyl, C$_{1-5}$ alkoxycarbonyl, —NR$_5$R$_6$ or NR$_5$R$_6$—C(O)—;

each R$_5$ or R$_6$ is independently:

hydrogen, phenylC$_{0-3}$ alkyl, naphthylC$_{0-3}$ alkyl, C$_{3-7}$ cycloalkylC$_{0-3}$ alkyl, heterocyclylC$_{0-3}$ alkyl or heterocyclylcarbonyl wherein the heterocyclyl is as hereinabove described for Y, heteroarylC$_{0-3}$ alkyl or heteroarylcarbonyl wherein the heteroaryl is as hereinabove described for Y, C$_{1-3}$ acyl, benzoyl, naphthoyl or C$_{1-6}$ branched or unbranched alkyl, each R$_5$ or R$_6$ is optionally substituted by C$_{1-5}$ alkoxy, hydroxy, mono- or di-C$_{1-3}$alkylaminocarbonyl, mono or diC$_{1-3}$ alkylamino, mono or diC$_{1-3}$ alkylsulfonylamino or C$_{1-3}$ alkylsulfonyl;

each R$_1$ is independently:

C$_{1-10}$ alkyl branched or unbranched, wherein one or more C atoms are optionally independently replaced by O, N or S(O)$_m$, and wherein said C$_{1-10}$ alkyl is optionally substituted with one to three C$_{3-10}$ cycloalkyl, hydroxy, oxo, phenyl, naphthyl or halogen, or R$_1$ is phenyl, cyclopropyloxy, cyclobutyloxy, cyclopentyloxy, cyclohexyloxy or cycloheptyloxy each optionally substituted with one to three C$_{1-3}$ alkyl groups, nitrile, hydroxyC$_{1-3}$alkyl phenyl or naphthyl;

phenyloxy or benzyloxy each optionally substituted with one to three C$_{1-3}$ alkyl groups, nitrile, hydroxyC$_{1-3}$alkyl phenyl or naphthyl;

cyclopropyl, cyclobutyl, cyclopentyl, cyclohexyl, cycloheptyl, bicyclopentanyl, bicyclohexanyl or bicycloheptanyl, each being optionally substituted with one to three C$_{1-3}$ alkyl, nitrile, hydroxyC$_{1-3}$alkyl phenyl or naphthyl;

C$_{3-10}$ branched or unbranced alkenyl each being optionally substituted with one to three C$_{1-5}$ branched or unbranched alkyl, phenyl or naphthyl, cyclopentenyl, cyclohexenyl, cyclohexadienyl, cycloheptenyl, cycloheptadienyl, bicyclohexenyl or bicycloheptenyl, each optionally substituted with one to three C$_{1-3}$ alkyl groups;

morpholinyl, piperazinyl, piperidinyl, pyrrolidinyl, tetrahydropyranyl or tetrahydrofuryl, oxo, nitrile, halogen; or C$_{3-6}$ alkynyl branched or unbranched carbon chain wherein one or more methylene groups are optionally replaced by O, N or S(O)$_m$ and wherein said alkynyl group is optionally independently substituted with one to two oxo groups, hydroxy, pyrrolidinyl, pyrrolyl, tetrahydropyranyl, one or more C$_{1-4}$ alkyl optionally substituted by one or more halogen atoms, nitrile, morpholino, piperidinyl, piperazinyl, imidazolyl, phenyl, pyridinyl, tetrazolyl or mono- or di(C$_{1-3}$alkyl)amino;

each R$_2$ is independently:

a C$_{1-6}$ branched or unbranched alkyl optionally halogenated, C$_{1-6}$acyl, benzoyl, naphthoyl, C$_{1-4}$ branched or unbranched alkoxy optionally halogenated, halogen, methoxycarbonyl, C$_{1-4}$ alkyl-S(O)$_m$ branched or unbranched or phenyl-S(O)$_m$;

each R$_3$ is independently

C$_{1-6}$ branched or unbranched alkyl, phenylC$_{0-6}$ alkyl, naphthylC$_{0-6}$ alkyl, heteroarylC$_{0-6}$ alkyl, heterocyclyl C$_{0-6}$ alkyl each optionally substituted with one to three C$_{1-3}$ alkyl groups, nitrile, hydroxyC$_{1-3}$alkyl phenyl or naphthyl;

amino wherein the nitrogen atom is optionally mono- or di-substituted by C$_{1-6}$ branched or unbranched alkyl, phenylC$_{0-6}$ alkyl, naphthylC$_{0-6}$ alkyl, heteroarylC$_{0-6}$ alkyl and heterocyclyl C$_{0-6}$ alkyl;

J-S(O)$_m$—NR$_7$— wherein the nitrogen atom is covalently attached to G;

or R$_3$ is J-NR$_7$—C(O)—, wherein

R$_7$ is hydrogen or C$_{1-3}$ alkyl;

J is chosen from C$_{1-6}$ branched or unbranched alkyl optionally substituted with 1 to 3 halogen atoms, phenylC$_{0-6}$ alkyl, naphthylC$_{0-6}$ alkyl, heteroarylC$_{0-6}$ alkyl and heterocyclyl C$_{0-6}$ alkyl;

each m is independently 0, 1 or 2;

and X is O or S;

or the pharmaceutically acceptable salts.

9. The compound according to claim 8 and wherein ring A and the phenyl ring to which it is fused form:

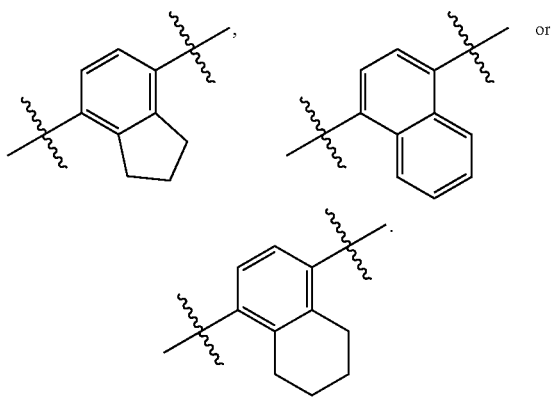

10. The compound according to claim 9 and wherein

G is a 6-membered monocyclic heteroaryl ring chosen from pyridinyl, pyrimidinyl, pyrazinyl and pyridazinyl;

phenyl, naphthyl, indanyl, indenyl or C$_{3-7}$ cycloalkyl;

wherein G is optionally substituted by one to three R$_1$, R$_2$ or R$_3$;

ring A and the phenyl ring to which it is fused form:

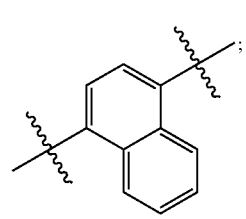

Q is a ring system chosen from benzimidazolyl, benzothiazolyl, benzooxazolyl, benzisoxazolyl, benzofuranyl, benzofuranyl, benzodioxolyl, indolyl, isoindolyl, imidazo[4,5-b]pyridinyl, imidazo[4,5-c]pyridinyl, purinyl, indazolyl, quinolinyl, isoquinolinyl, quinazolinyl, benzopyranyl, benzoxazinyl, pyrido[2,3-b]oxazinyl, pyrido[2,3-b]pyrazinyl, pyrido[2,3-b]thiazinyl, pyrrolo[3,2-c]pyridinyl and pyrazolo[3,4-d]pyrimidinyl;

wherein each Q is optionally substituted with one to three Y, $R_1$ is $C_{1-10}$ alkyl, $C_{1-9}$ alkoxy each branched or unbranched and optionally substituted with one to three $C_{3-10}$ cycloalkyl, hydroxy, oxo, phenyl, naphthyl or halogen, morpholinyl, piperazinyl, piperidinyl, or $R_1$ is phenyl, cyclopropyl, cyclobutyl, cyclopentyl, cyclohexyl, cycloheptyl, bicyclopentanyl, bicyclohexanyl or bicycloheptanyl, each being optionally substituted with one to three $C_{1-3}$ alkyl, nitrile, hydroxy$C_{1-3}$alkyl phenyl or naphthyl;

$R_2$ is halogen, $C_{1-6}$ branched or unbranched alkyl or $C_{1-4}$ branched or unbranched alkoxy each optionally halogenated;

$R_3$ is J-S(O)$_m$—NR$_7$— wherein the nitrogen atom is covalently attached to G and wherein J is chosen from a $C_{1-6}$ branched or unbranched alkyl optionally substituted with 1 to 3 halogen atoms, phenyl$C_{0-6}$ alkyl, naphthyl$C_{0-6}$ alkyl, heteroaryl$C_{0-6}$ alkyl and heterocyclyl $C_{0-6}$ alkyl; and X is O.

11. The compound according to claim 10 and wherein

G is pyridinyl, phenyl, naphthyl, indanyl, indenyl or $C_{3-7}$ cycloalkyl;

wherein G is optionally substituted by one to three $R_1$, $R_2$ or $R_3$;

wherein each Y is independently chosen from

L-NR$_5$R$_6$ wherein L is a bond or —(CH$_2$)$_{1-5}$—;

hydrogen, oxo, $C_{1-5}$ alkyl branched or unbranched, $C_{1-3}$ acyl, heterocyclyl$C_{0-3}$ alkyl wherein the heterocyclyl is chosen from morpholinyl, piperazinyl, and pyrrolidinyl, heteroaryl$C_{0-3}$ alkyl wherein the heteroaryl is chosen from pyridinyl, pyrimidinyl, pyrazinyl, pyridazinyl, pyrrolyl, imidazolyl, pyrazolyl, isoxazolyl, thiazolyl and oxazolyl, phenyl, naphthyl, benzyl and phenethyl, wherein each Y is optionally substituted by one to three hydroxy, oxo, $C_{1-4}$ alkyl, $C_{1-3}$ alkoxy, $C_{1-4}$ acyl, $C_{1-5}$ alkoxycarbonyl or —NR$_5$R$_6$;

each R$_5$ or R$_6$ is independently:

hydrogen, phenyl, naphthyl, benzyl, phenethyl, $C_{3-7}$ cycloalkyl$C_{0-3}$ alkyl, heterocyclyl$C_{0-3}$ alkyl or heterocyclylcarbonyl wherein the heterocyclyl is chosen from morpholinyl, tetrahydrofuranyl and tetrahydropyranyl, heteroaryl$C_{0-3}$ alkyl or heteroarylcarbonyl wherein the heteroaryl is chosen from pyridinyl, pyridinyl, pyrimidinyl, pyrazinyl and pyridazinyl, $C_{1-3}$ acyl, benzoyl, naphthoyl or $C_{1-6}$ branched or unbranched alkyl, each R$_5$ or R$_6$ is optionally substituted by $C_{1-5}$ alkoxy, mono or di$C_{1-3}$ alkyl amino, mono or di$C_{1-3}$ alkylsulfonylamino or $C_{1-3}$ alkylsulfonyl;

$R_1$ is $C_{1-10}$ alkyl, $C_{1-9}$ alkoxy each branched or unbranched and optionally substituted with one to three $C_{3-10}$ cycloalkyl, hydroxy, oxo, phenyl, naphthyl, fluoro, bromo or chloro or $R_1$ is morpholinyl or phenyl; and $R_3$ is J-S(O)$_m$—NR$_7$— wherein the nitrogen atom is covalently attached to G and wherein J is chosen from a $C_{1-6}$ branched or unbranched alkyl optionally substituted with 1 to 3 halogen atoms phenyl$C_{0-6}$ alkyl, and naphthyl$C_{0-6}$ alkyl.

12. The compound according to claim 11 and wherein

G is pyridinyl, phenyl, cyclopropyl or naphthyl each optionally substituted by one to three $R_1$, $R_2$ or $R_3$;

Q is chosen from imidazo[4,5-b]pyridinyl, imidazo[4,5-c]pyridinyl, pyrido[2,3-b]oxazinyl, pyrido[2,3-b]pyrazinyl, pyrido[2,3-b]thiazinyl, pyrazolo[3,4-d]pyrimidinyl, isoquinolinyl, purinyl and pyrrolo[3,2-c]pyridinyl;

wherein each Q is optionally substituted with one to three Y, wherein each Y is independently chosen from L-NR$_5$R$_6$ wherein L is a bond or —(CH$_2$)$_{1-5}$—, hydrogen, oxo, $C_{1-5}$ alkyl branched or unbranched, heterocyclyl$C_{0-3}$ alkyl wherein the heterocyclyl is chosen from morpholinyl, piperazinyl, and pyrrolidinyl, pyridinyl$C_{0-3}$ alkyl or benzyl, wherein each Y is optionally substituted by one to three hydroxy, oxo, $C_{1-4}$ alkyl, $C_{1-3}$ alkoxy, $C_{1-4}$ acyl or —NR$_5$R$_6$;

each R$_5$ or R$_6$ is independently:

hydrogen, phenyl, benzyl, $C_{3-6}$ cycloalkyl$C_{0-3}$ alkyl, heterocyclyl$C_{0-3}$ alkyl or heterocyclylcarbonyl wherein the heterocyclyl is chosen from morpholinyl, tetrahydrofuranyl and tetrahydropyranyl, pyridinyl$C_{0-3}$ alkyl, pyridinylcarbonyl, $C_{1-3}$ acyl, benzoyl or $C_{1-6}$ branched or unbranched alkyl optionally substituted by $C_{1-5}$ alkoxy, mono or di$C_{1-3}$ alkyl amino, mono or di$C_{1-3}$ alkylsulfonylamino or $C_{1-3}$ alkylsulfonyl;

$R_7$ is hydrogen; and

J is $C_{1-6}$ branched or unbranched alkyl optionally substituted with 1 to 3 halogen atoms.

13. The compound according to claim 12 and wherein

Q is chosen from:

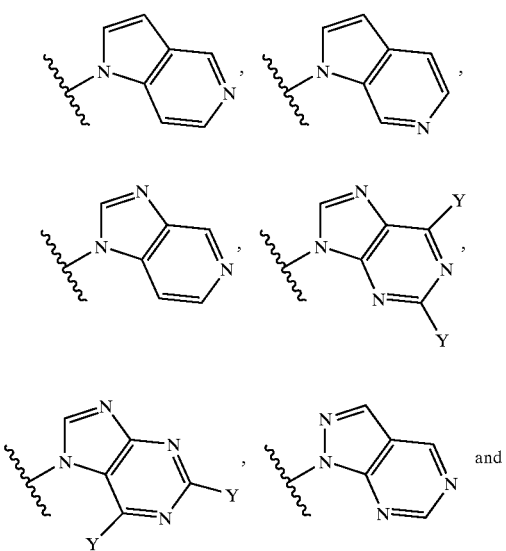

R₁ is morpholinyl, phenyl, CF₃, OCF₃, —C(CH₃)₃, —C(CH₂F)₃ or —CH₂C(CH₃)₃;

R₂ is chloro, bromo, fluoro, $C_{1-4}$ branched or unbranched alkoxy, CF₃ or OCF₃; and J is $C_{1-3}$ alkyl optionally substituted with 1 to 3 halogen atoms.

14. The compound according to claim 13 and wherein G is:

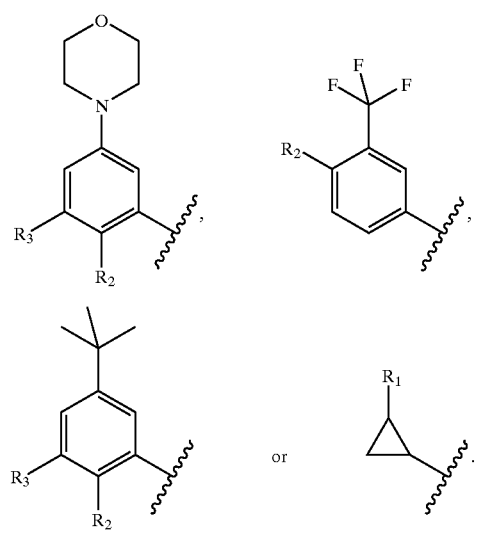

15. The compound according to claim 14 and wherein G is:

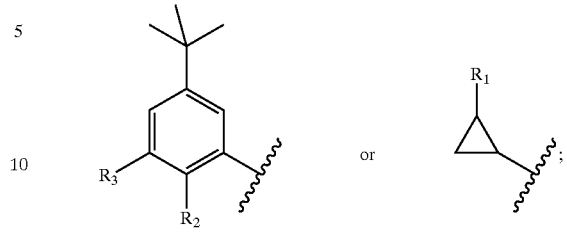

Y is independently chosen from

L-NR₅R₆ wherein L is a bond or —(CH₂)$_{1-3}$—, $C_{1-5}$ alkyl branched or unbranched, morpholinylC$_{0-3}$ alkyl or benzyl; and each R₅ or R₆ is independently:

hydrogen, phenyl, benzyl or $C_{3-6}$ cycloalkylC$_{0-3}$ alkyl.

16. A compound chosen from:

1-[4-(3-Benzyl-3H-imidazo[4,5-b]pyridin-6-yl)-naphthalen-1-yl]-3-(5-tert-butyl-2-p-tolyl-2H-pyrazol-3-yl)-urea;
1-(5-tert-Butyl-2-p-tolyl-2H-pyrazol-3-yl)-3-[4-(3H-imidazo[4,5-b]pyridin-6-yl)-naphthalen-1-yl]-urea;
1-(5-tert-Butyl-2-p-tolyl-2H-pyrazol-3-yl)-3-[4-(2-oxo-2,3-dihydro-1H-pyrido[2,3-b][1,4]oxazin-7-yl)-naphthalen-1-yl]-urea;
1-(5-tert-Butyl-2-p-tolyl-2H-pyrazol-3-yl)-3-(4-pyrrolo[3,2-c]pyridin-1-yl-naphthalen-1-yl)-urea;
1-(5-tert-Butyl-2-methoxy-phenyl)-3-[4-(3H-imidazol[4,5-b]pyridin-6-yl)-naphthalen-1-yl]-urea;
1-(5-tert-Butyl-2-methoxy-phenyl)-3-[4-(2-morpholin-4-ylmethyl-3H-imidazo[4,5-b]pyridin-6-yl)-naphthalen-1-yl]-urea;
1-(5-tert-Butyl-2-methoxy-phenyl)-3-[4-(2-oxo-2,3-dihydro-1H-pyrido[2,3-b][1,4]oxazin-7-yl)-naphthalen-1-yl]-urea;
1-(5-tert-Butyl-2-methoxy-phenyl)-3-[4-(2-oxo-1,2,3,4-tetrahydro-pyrido[2,3-b]pyrazin-7-yl)-naphthalen-1-yl]-urea;
1-(5-tert-Butyl-2-methoxy-phenyl)-3-[4-(2-oxo-2,3-dihydro-1H-pyrido[2,3-b][1,4]thiazin-7-yl)-naphthalen-1-yl]-urea;
1-(5-tert-Butyl-2-methoxy-phenyl)-3-[4-(2,4-dioxo-1,2,3,4-tetrahydro-4-lambda-4-pyrido[2,3-b][1,4]thiazin-7-yl)-naphthalen-1-yl]-urea;
1-(5-tert-Butyl-2-methoxy-phenyl)-3-[4-(2,4,4-trioxo-1,2,3,4-tetrahydro-4-lambda-6-pyrido[2,3-b][1,4]thiazin-7-yl)-naphthalen-1-yl]-urea;
N-(5-tert-Butyl-2-methoxy-3-{3-[4-(2-oxo-2,3-dihydro-1H-pyrido[2,3-b][1,4]oxazin-7-yl)-naphthalen-1-yl]-ureido}-phenyl)-methanesulfonamide;
N-(5-tert-Butyl-2-methoxy-3-{3-[4-(3-methyl-2-oxo-2,3-dihydro-1H-pyrido[2,3-b][1,4]oxazin-7-yl)-naphthalen-1-yl]-ureido}-phenyl)-methanesulfonamide;
N-(3-{3-[4-(3-Benzyl-2-oxo-2,3-dihydro-1H-pyrido[2,3-b][1,4]oxazin-7-yl)-naphthalen-1-yl]-ureido}-5-tert-butyl-2-methoxy-phenyl)-methanesulfonamide;
N-{5-tert-Butyl-2-methoxy-3-[3-(4-pyrrolo[3,2-c]pyridin-1-yl-naphthalen-1-yl)-ureido]-phenyl}-methanesulfonamide;
1-(5-tert-Butyl-2-methoxy-phenyl)-3-(4-pyrrolo[3,2-c]pyridin-1-yl-naphthalen-1-yl)-urea;
N-{5-tert-Butyl-3-[3-(4-imidazo[4,5-c]pyridin-3-yl-naphthalen-1-yl)-ureido]-2-methoxy-phenyl}-methanesulfonamide;
N-{5-tert-Butyl-3-[3-(4-imidazo[4,5-c]pyridin-1-yl-naphthalen-1-yl)-ureido]-2-methoxy-phenyl}-methanesulfonamide
1-(5-tert-Butyl-2-methoxy-phenyl)-3-{4-[3-(2-morpholin-4-yl-ethyl)-3H-imidazo[4,5-b]pyridin-6-yl]-naphthalen-1-yl}-urea;
1-(5-tert-Butyl-2-methoxy-phenyl)-3-{4-[3-(2-dimethylamino-ethyl)-3H-imidazo[4,5-b]pyridin-6-yl]-naphthalen-1-yl}-urea;
1-(5-tert-Butyl-2-methoxy-phenyl)-3-[4-(3-pyridin-2-ylmethyl-3H-imidazo[4,5-b]pyridin-6-yl)-naphthalen-1-yl]-urea;
1-[4-(1-Benzyl-1H-imidazo[4,5-b]pyridin-6-yl)-naphthalen-1-yl]-3-(5-tert-butyl-2-methoxy-phenyl)-urea;
1-[4-(2-Amino-3H-imidazo[4,5-b]pyridin-6-yl)-naphthalen-1-yl]-3-(5-tert-butyl-2-methoxy-phenyl)-urea;
N-(6-{4-[3-(5-tert-Butyl-2-methoxy-phenyl)-ureido]-naphthalen-1-yl}-3H-imidazo[4,5-b]pyridin-2-yl)-acetamide;
N-(6-{4-[3-(5-tert-Butyl-2-methoxy-phenyl)-ureido]-naphthalen-1-yl}-3H-

-continued imidazo[4,5-b]pyridin-2-yl)-benzamide;
N-(6-{4-[3-(5-tert-Butyl-2-methoxy-phenyl)-ureido]-naphthalen-1-yl}-3H-imidazo[4,5-b]pyridin-2-yl)-nicotinamide;
N-(6-{4-[3-(5-tert-Butyl-2-methoxy-phenyl)-ureido]-naphthalen-1-yl}-3H-imidazo[4,5-b]pyridin-2-yl)-methanesulfonamide;
1-(5-tert-Butyl-2-methoxy-phenyl)-3-[4-(3-methanesulfonyl-3H-imidazo[4,5-b]pyridin-6-yl)-naphthalen-1-yl]-urea;
1-(5-tert-Butyl-2-methoxy-phenyl)-3-[4-(2-diethylaminomethyl-3H-imidazo[4,5-b]pyridin-6-yl)-naphthalen-1-yl]-urea;
1-(5-tert-Butyl-2-methoxy-phenyl)-3-[4-(2-pyrrolidin-1-ylmethyl-3H-imidazo[4,5-b]pyridin-6-yl)-naphthalen-1-yl]-urea;
1-(5-tert-Butyl-2-methoxy-phenyl)-3-{4-[2-(4-methyl-piperazin-1-ylmethyl)-3H-imidazo[4,5-b]pyridin-6-yl]-naphthalen-1-yl}-urea;
1-(5-tert-Butyl-2-methoxy-phenyl)-3-[4-(2-oxo-2,3-dihydro-1H-imidazo[4,5-b]pyridin-6-yl)-naphthalen-1-yl]-urea;
1-(5-tert-Butyl-2-methoxy-phenyl)-3-[4-(2,3-dioxo-1,2,3,4-tetrahydro-pyrido[2,3-b]pyrazin-7-yl)-naphthalen-1-yl]-urea;
1-[4-(3-Benzyl-2-oxo-2,3-dihydro-1H-pyrido[2,3-b][1,4]oxazin-7-yl)-naphthalen-1-yl]-3-(5-tert-butyl-2-methoxy-phenyl)-urea;
1-(5-tert-Butyl-2-methoxy-phenyl)-3-[4-(1-methyl-2-oxo-2,3-dihydro-1H-pyrido[2,3-b][1,4]oxazin-7-yl)-naphthalen-1-yl]-urea;
1-(5-tert-Butyl-2-methoxy-phenyl)-3-[4-(3-methyl-2-oxo-2,3-dihydro-1H-pyrido[2,3-b][1,4]oxazin-7-yl)-naphthalen-1-yl]-urea;
1-(5-tert-Butyl-2-methoxy-phenyl)-3-[4-(2-oxo-3-pyridin-2-ylmethyl-2,3-dihydro-1H-pyrido[2,3-b][1,4]oxazin-7-yl)-naphthalen-1-yl]-urea;
1-(5-tert-Butyl-2-methoxy-phenyl)-3-{4-[3-(3,4-dimethoxy-benzyl)-2-oxo-2,3-dihydro-1H-pyrido[2,3-b][1,4]oxazin-7-yl]-naphthalen-1-yl}-urea;
1-(5-tert-Butyl-2-methoxy-phenyl)-3-{4-[3-(2-dimethylamino-ethyl)-2-oxo-2,3-dihydro-1H-pyrido[2,3-b][1,4]oxazin-7-yl]-naphthalen-1-yl}-urea;
1-(5-tert-Butyl-2-methoxy-phenyl)-3-(4-isoquinolin-5-yl-naphthalen-1-yl)-urea;
1-(5-tert-Butyl-2-methoxy-phenyl)-3-(4-purin-9-yl-naphthalen-1-yl)-urea;
1-(5-tert-Butyl-2-methoxy-phenyl)-3-(4-purin-7-yl-naphthalen-1-yl)-urea;
1-[4-(6-Amino-purin-9-yl)-naphthalen-1-yl]-3-(5-tert-butyl-2-methoxy-phenyl)-urea;
1-(5-tert-Butyl-2-methoxy-phenyl)-3-[4-(6-methylamino-purin-9-yl)-naphthalen-1-yl]-urea;
1-(5-tert-Butyl-2-methoxy-phenyl)-3-[4-(6-dimethylamino-purin-9-yl)-naphthalen-1-yl]-urea;
1-(5-tert-Butyl-2-methoxy-phenyl)-3-[4-(6-cyclopropylamino-purin-9-yl)-naphthalen-1-yl]-urea;
1-(5-tert-Butyl-2-methoxy-phenyl)-3-{4-[6-(cyclopropylmethyl-amino)-purin-9-yl]-naphthalen-1-yl}-urea;
1-(5-tert-Butyl-2-methoxy-phenyl)-3-{4-[6-(2-methoxy-ethylamino)-purin-9-yl]-naphthalen-1-yl}-urea;
1-(5-tert-Butyl-2-methoxy-phenyl)-3-{4-[6-(2-dimethylamino-ethylamino)-purin-9-yl]-naphthalen-1-yl}-urea;
1-[4-(6-Benzylamino-purin-9-yl)-naphthalen-1-yl]-3-(5-tert-butyl-2-methoxy-phenyl)-urea;
1-(5-tert-Butyl-2-methoxy-phenyl)-3-(4-{6-[(pyridin-2-ylmethyl)-amino]-purin-9-yl}-naphthalen-1-yl)-urea;
1-(5-tert-Butyl-2-methoxy-phenyl)-3-{4-[6-(2-methoxy-1-methyl-ethylamino)-purin-9-yl]-naphthalen-1-yl}-urea;
1-(5-tert-Butyl-2-methoxy-phenyl)-3-{4-[6-(1-phenyl-ethylamino)-purin-9-yl]-naphthalen-1-yl}-urea;
1-(5-tert-Butyl-2-methoxy-phenyl)-3-[4-(6-cyclopentylamino-purin-9-yl)-naphthalen-1-yl]-urea;
1-(5-tert-Butyl-2-methoxy-phenyl)-3-[4-(6-isopropylamino-purin-9-yl)-naphthalen-1-yl]-urea;
1-(5-tert-Butyl-2-methoxy-phenyl)-3-[4-(6-cyclohexylamino-purin-9-yl)-naphthalen-1-yl]-urea;
1-(5-tert-Butyl-2-methoxy-phenyl)-3-{4-[6-(tetrahydro-pyran-4-ylamino)-purin-9-yl]-naphthalen-1-yl}-urea;
1-(5-tert-Butyl-2-methoxy-phenyl)-3-{4-[6-(tetrahydro-furan-3-ylamino)-purin-9-yl]-naphthalen-1-yl}-urea;
1-(5-tert-Butyl-2-methoxy-phenyl)-3-[4-(6-pyrrolidin-1-yl-purin-9-yl)-naphthalen-1-yl]-urea;
1-(5-tert-Butyl-2-methoxy-phenyl)-3-[4-(6-morpholin-4-yl-purin-9-yl)-naphthalen-1-yl]-urea;
1-(5-tert-Butyl-2-methoxy-phenyl)-3-{4-[6-(4-methyl-piperazin-1-yl)-purin-9-yl]-naphthalen-1-yl}-urea;
1-(5-tert-Butyl-2-methoxy-phenyl)-3-(4-{6-[(2-dimethylamino-ethyl)-methyl-amino]-purin-9-yl}-naphthalen-1-yl)-urea;
1-(5-tert-Butyl-2-methoxy-phenyl)-3-{4-[6-(2-morpholin-4-yl-ethylamino)-purin-9-yl]-naphthalen-1-yl}-urea;
1-(5-tert-Butyl-2-methoxy-phenyl)-3-[4-(6-ethylamino-2-methyl-purin-9-yl)-naphthalen-1-yl]-urea;
1-(5-tert-Butyl-2-methoxy-phenyl)-3-{4-[2-methyl-6-(2-morpholin-4-yl-ethylamino)-purin-9-yl]-naphthalen-1-yl}-urea;

-continued 1-(5-tert-Butyl-2-methoxy-phenyl)-3-[4-(6-cyclopropylamino-2-methyl-purin-9-yl)-naphthalen-1-yl]-urea;
1-(5-tert-Butyl-2-methoxy-phenyl)-3-[4-(2,6-dioxo-1,2,3,6-tetrahydro-purin-7-yl)-naphthalen-1-yl]-urea;
1-(5-tert-Butyl-2-methoxy-phenyl)-3-[4-(2,6-dioxo-1,2,3,6-tetrahydro-purin-9-yl)-naphthalen-1-yl]-urea and
1-(5-tert-Butyl-2-methoxy-phenyl)-3-(4-pyrazolo[3,4-d]pyrimidin-1-yl-naphthalen-1-yl)-urea
or the pharmaceutically acceptable salts.

17. A pharmaceutical composition comprising a pharmaceutically effective amount of a compound according to claims 1, 8 or 16 and one or more pharmaceutically acceptable carriers.

18. A process of making a compound according to claim 1:

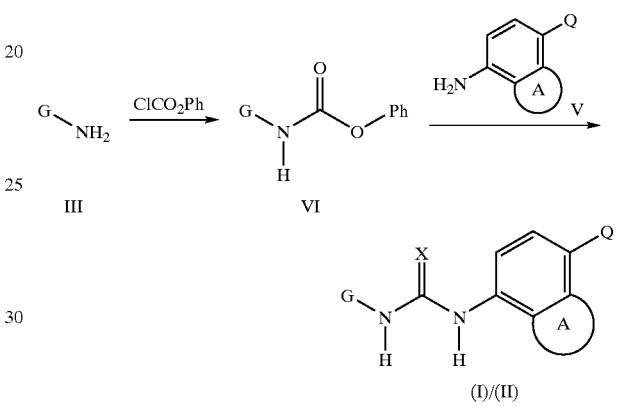

wherein G, X, A and Q of the formula I or II are described in claim 1, comprising:
  reacting an arylamine of formula III with an alkyl or aryl chloroformate, in a suitable solvent, optionally in the presence of a suitable base, at a temperature between 0–85° C. for 2–24 h providing carbamate VI;
  reacting the carbamate and arylamine V in a non-protic, anhydrous solvent between 0–110° C. for 2–24 h, providing the product of formula I or II; wherein each aryl moiety recited hereinabove is phenyl or naphthyl.

19. A method of treating a disease or condition selected from Behcet's disease, ankylosing spondylitis, rheumatoid arthritis, inflammatory bowel disease, septic shock, osteoarthritis, Crohn's disease, ulcerative colitis, multiple sclerosis, Guillain-Barre syndrome, psoriasis, graft versus host disease, systemic lupus erythematosus, restenosis following percutaneous transluminal coronary angioplasty, diabetes, toxic shock syndrome, Alzheimer's disease, acute and chronic pain, contact dermatitis, atherosclerosis, glomerulonephritis, reperfusion injury, sepsis, bone resorption diseases, chronic obstructive pulmonary disease, asthma, stroke, myocardial infarction, thermal injury, adult respiratory distress syndrome (ARDS), multiple organ injury secondary to trauma, dermatoses with acute inflammatory components, acute purulent meningitis, necrotizing enterocolitis comprising administering to a patient a pharmaceutically effective amount of a compound according to claims 1, 8 or 16.

20. The method according to claim 19 wherein the disease is selected from rheumatoid arthritis, osteoarthritis, Crohn's disease, psoriasis, ulcerative colitis, osteoporosis, chronic obstructive pulmonary disease and restenosis following percutaneous transluminal coronary angioplasty.

* * * * *